United States Patent
Wu et al.

(10) Patent No.: US 11,213,560 B2
(45) Date of Patent: Jan. 4, 2022

(54) METHOD OF PROMOTING WOUND HEALING WITH SINETIRUCALLOL

(71) Applicant: NATIONAL DONG HWA UNIVERSITY, Hualien (TW)

(72) Inventors: Maw-Kuen Wu, Taipei (TW); Ching-Feng Weng, Taipei (TW); Huei Wun Sie, Tainan (TW); Hung Yuan Shih, Taipei (TW)

(73) Assignee: NATIONAL DONG HWA UNIVERSITY, Hualien (TW)

( * ) Notice: Subject to any disclaimer, the term of this patent is extended or adjusted under 35 U.S.C. 154(b) by 0 days.

(21) Appl. No.: 16/885,876

(22) Filed: May 28, 2020

(65) Prior Publication Data

US 2020/0289602 A1 Sep. 17, 2020

Related U.S. Application Data

(60) Division of application No. 15/655,530, filed on Jul. 20, 2017, now abandoned, which is a continuation of application No. PCT/US2015/048192, filed on Sep. 2, 2015.

(60) Provisional application No. 62/106,177, filed on Jan. 21, 2015.

(30) Foreign Application Priority Data

Mar. 6, 2015 (TW) .................. 104107161

(51) Int. Cl.
| *A61K 36/898* | (2006.01) |
| *A23L 33/105* | (2016.01) |
| *A23L 2/52* | (2006.01) |
| *A61K 9/00* | (2006.01) |
| *A61K 31/575* | (2006.01) |

(52) U.S. Cl.
CPC .............. *A61K 36/898* (2013.01); *A23L 2/52* (2013.01); *A23L 33/105* (2016.08); *A61K 9/0014* (2013.01); *A61K 31/575* (2013.01); *A23V 2002/00* (2013.01)

(58) Field of Classification Search
None
See application file for complete search history.

(56) References Cited

U.S. PATENT DOCUMENTS 9,750,783 B2 * 9/2017 Wu ...................... A61K 36/898

FOREIGN PATENT DOCUMENTS

| CN | 1255350 | A | 6/2000 |
| CN | 101253915 | A | 9/2008 |
| CN | 101279051 | A | 10/2008 |
| CN | 101347581 | A | 1/2009 |
| CN | 102579915 | * | 7/2012 |
| CN | 102579915 | A | 7/2012 |
| CN | 102671024 | A | 9/2012 |
| CN | 103041175 | A | 4/2013 |
| CN | 103212000 | * | 7/2013 |
| CN | 103423398 | A | 12/2013 |
| PT | 104 265 | A1 | 5/2010 |

OTHER PUBLICATIONS

Lin, Y. et al. Homocyclotirucallane and Two Dihydrophenanthrenes from Spiranthes sinensis. Chem Pharm Bull 49(9)1098-1101, 2001. (Year: 2001).*
Sarma, C. et al. Medicinally Important Orchids of North East India. Indian J of Environment and Ecoplanning 14(1-2)91-100, 2007. Abstact provided, full article on order. (Year: 2007).*
Sarrma, C. et al. Medicinally Important Orchids of North East Asia. Indian J of Environment & Ecoplanning 14(1-2)91-100, 2007. (Year: 2007).*
Liu, Jing, et al., "Chemical constituents from *Spiranthes sinensis*," *Biochemical Systematics and Ecology*, vol. 47, pp. 108-110 (2013).
Lin, Yun-Lian, et al., "Homocyclotirucallane and Two Dihydrophenanthrenes from *Spiranthes sinensis*," *Chem. Pharm. Bull*, vol. 49, No. 9, pp. 1098-1101 (2001).
Xiuzhen Zhongyao Yingyong Sucha Shouce, Hu et al., p. 760 (Jul. 2012).
Sarma, C.M., et al., "Medicinally important orchids of North East India," *CAPLUS Abstract, Indian Journal of Environment and Ecoplanning*, DN 148:1278806, vol. 14(1-2), 91-100 (2007).
Yin, Yong-Qin, et al., "Study on Chemical Constituents from *Spiranthes sinensis*," *Chinese Journal of Experimental Traditional Medical Formulae*, vol. 19, No. 19, pp. 76-78 (Oct. 2013).
Chiou, Wen-Fei, et al., "Effects of Six Anti-Inflammatory Chinese Herbs on LPS/IFN-γ-Induced Nitric Oxide Production in RAW264.7 Macrophages," *J. Chin. Med.*, vol. 11, No. 2, pp. 87-94 (2000).
Lin, Regina, et al., "Biological Evaluation of Subglutinol A as a Novel Immunosuppressive Agent for Inflammation Intervention," *ACS Med. Chem. Lett.*, vol. 5(5), pp. 485-490 (2014).
Fandiño-Vaquero, Rubén, et al., "Orosomucoid secretion levels by epicardial adipose tissue as possible indicator of endothelial dysfunction in diabetes mellitus or inflammation in coronary artery disease," *Atherosclerosis*, vol. 235, pp. 281-288 (2014).
Fink, Mitchell P., "Reactive oxygen species as mediators of organ dysfunction caused by sepsis, acute respiratory distress syndrome, or hemorrhagic shock: potential benefits of resuscitation with Ringer's ethyl pyruvate solution," *Current Opinion in Clinical Nutrition and Metabolic Care*, vol. 5, pp. 167-174 (2002).

(Continued)

*Primary Examiner* — Ralph J Gitomer
(74) *Attorney, Agent, or Firm* — Christensen, Fonder, Dardi & Herbert PLLC

(57) ABSTRACT

The present disclosure provides compositions and dosage forms comprising sinetirucallol, and methods of using such compositions, such as to treat an inflammation-associated disease, liver fibrosis, wound healing, and/or an autoimmune disease. In some embodiments, the composition comprises a *Spiranthes sinensis* extract.

6 Claims, 30 Drawing Sheets
Specification includes a Sequence Listing.

(56) References Cited

OTHER PUBLICATIONS

Dröge, Wulf, "Free Radicals in the Physiological Control of Cell Function," *Physiol. Rev.*, vol. 82, pp. 47-95 (2002).

Pantano, Cristen, et al., "Forum Review: Redox-Sensitive Kinases of the Nuclear Factor-κB Signaling Pathway," *Antioxidants & Redox Signaling*, vol. 8, Nos. 9&10, pp. 1791-1807 (2006).

Gloire, Geoffrey, et al., "NF-κB activation by reactive oxygen species: Fifteen years later," *Biochemical Pharmacology*, vol. 72, pp. 1493-1505 (2006).

Liu, Hongjun, et al., "Redox-Dependent Transcriptional Regulation," *Cir Res.*, vol. 97, pp. 967-974 (2005).

Lin, Shing-Jong, et al., "Superoxide Dismutase Inhibits the Expression of Vascular Cell Adhesion Molecule-1 and Intracellular Cell Adhesion Molecule-1 Induced by Tumor Necrosis Factor-α in Human Endothelial Cells Through the JNK/p38 Pathways," *Arterioscler Thromb. Vasc. Biol.*, vol. 25, pp. 334-340 (2005).

Nagai, Hiroaki, et al., "Pathophysiological Roles of ASK1-MAP Kinase Signaling Pathways," *Journal of Biochemistry and Molecular Biology*, vol. 40, No. pp. 1-6 (Jan. 2007).

Guzik, T.J., et al., "Nitric Oxide and Superoxide in Inflammation and Immune Regulation," *Journal of Physiology and Pharmacology*, vol. 54, No. 4, pp. 469-487 (2003).

\* cited by examiner

FIG. 12A
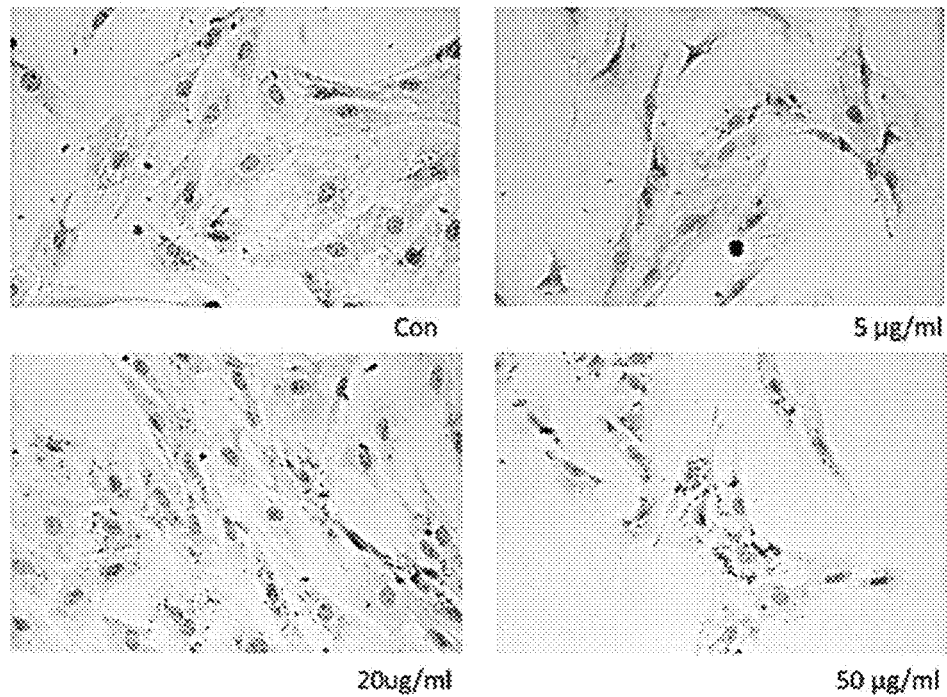
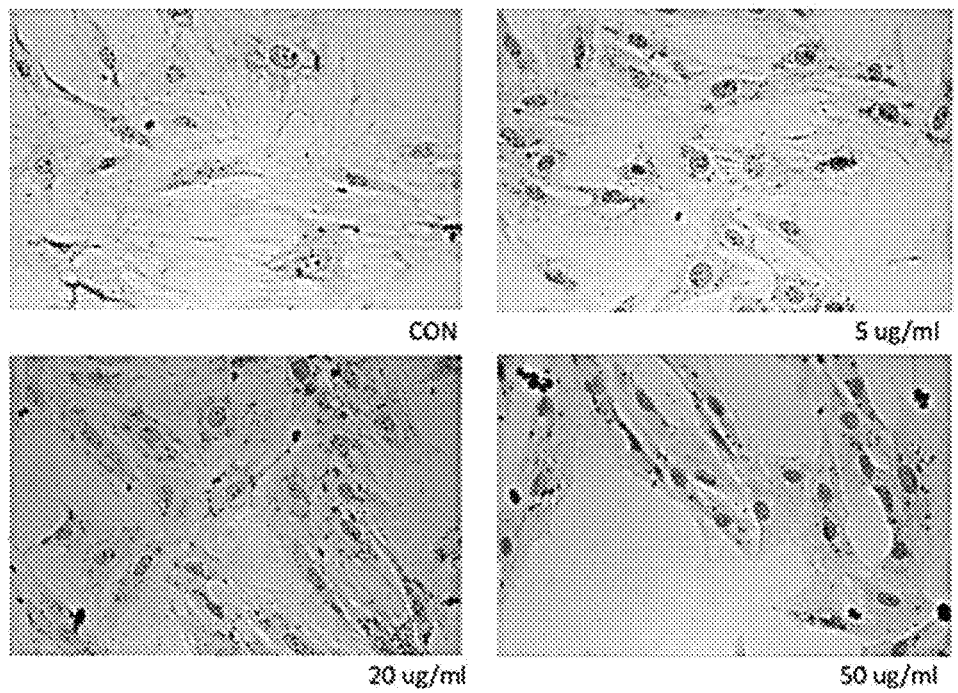
FIG. 12B

FIG. 15A
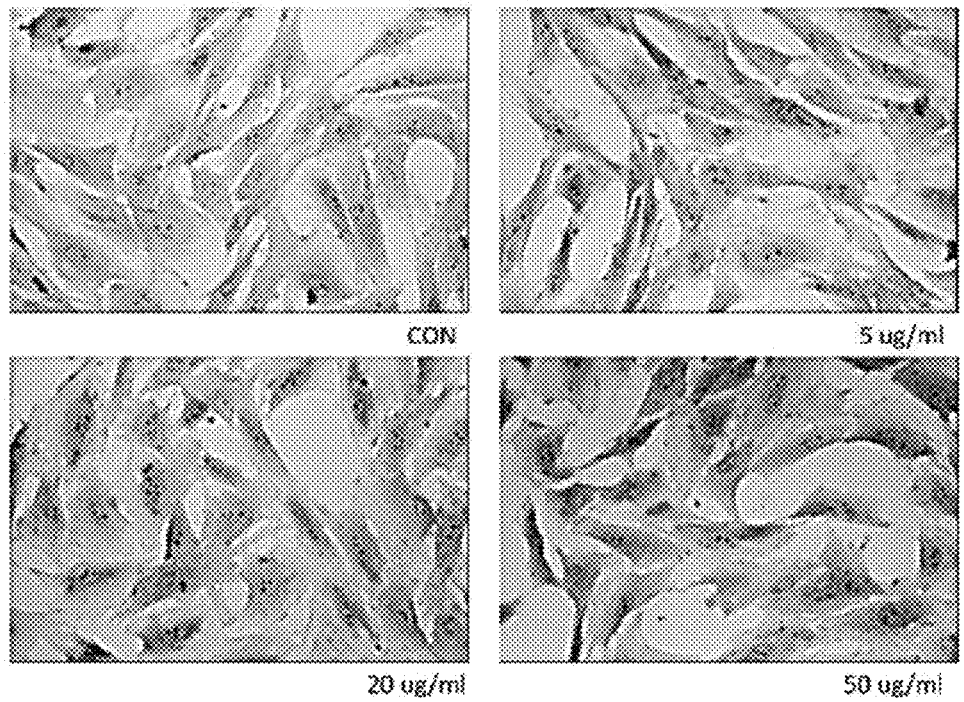
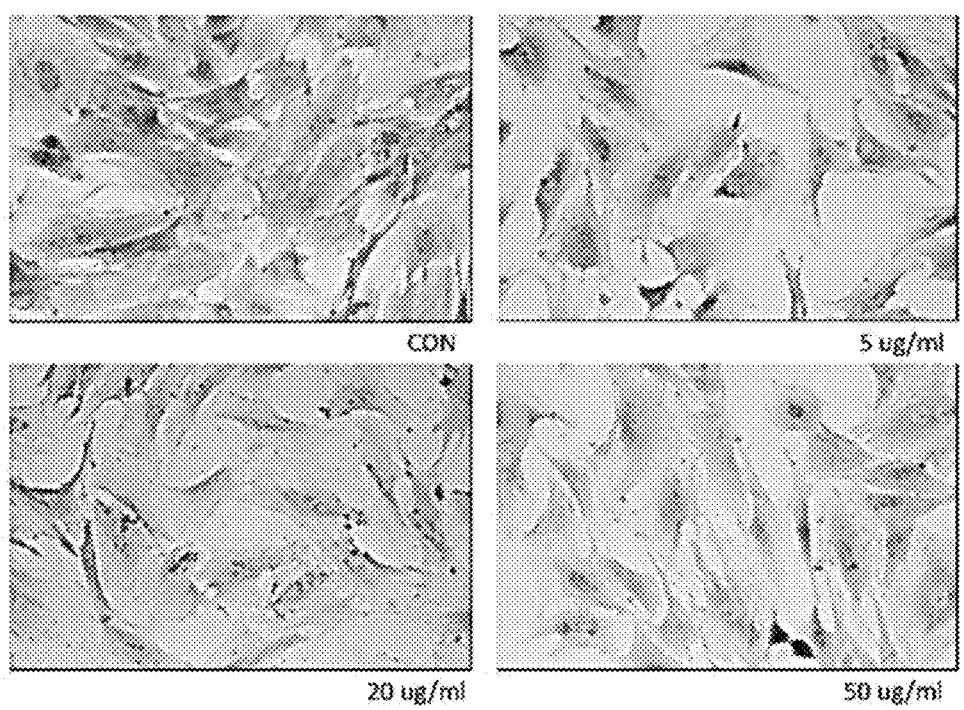
FIG. 15B

FIG. 16A (NHSC)
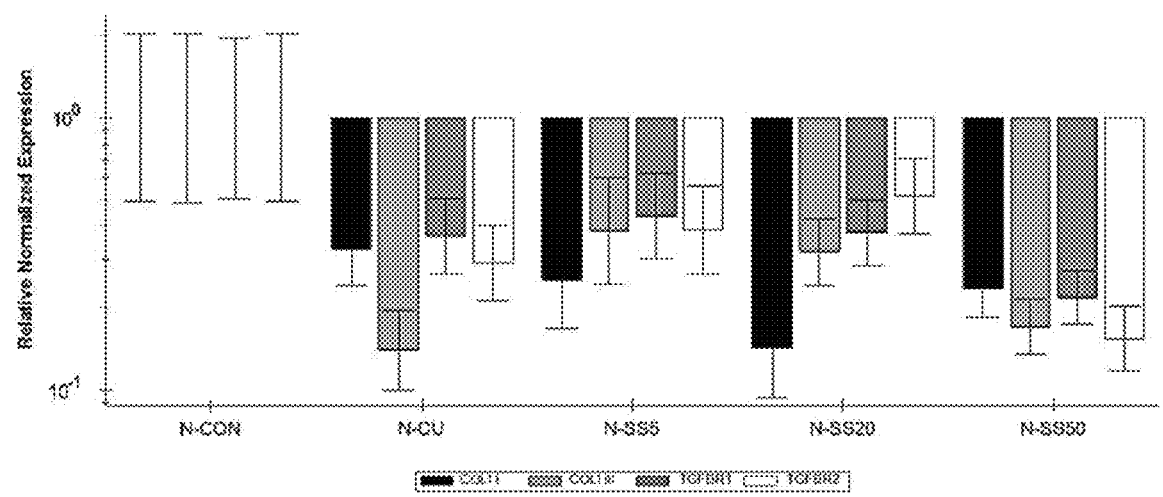
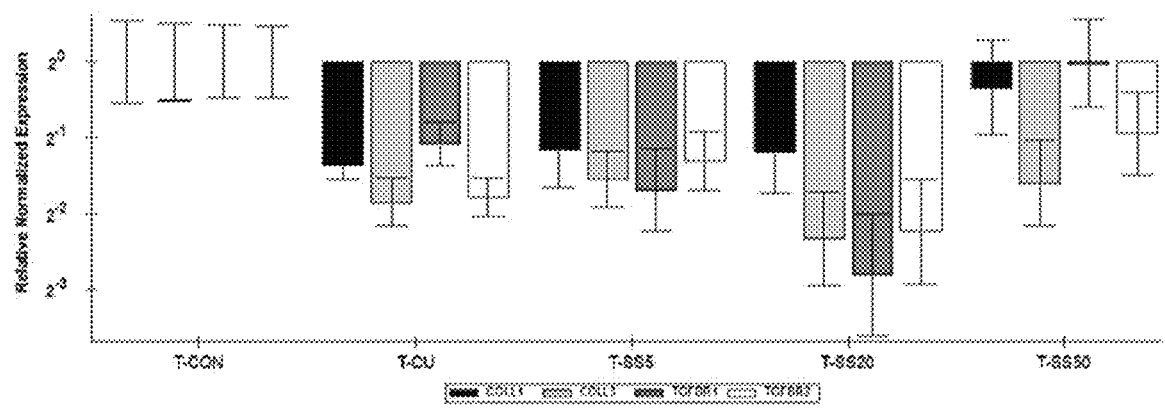
FIG. 16B (THSC)

FIG. 17A
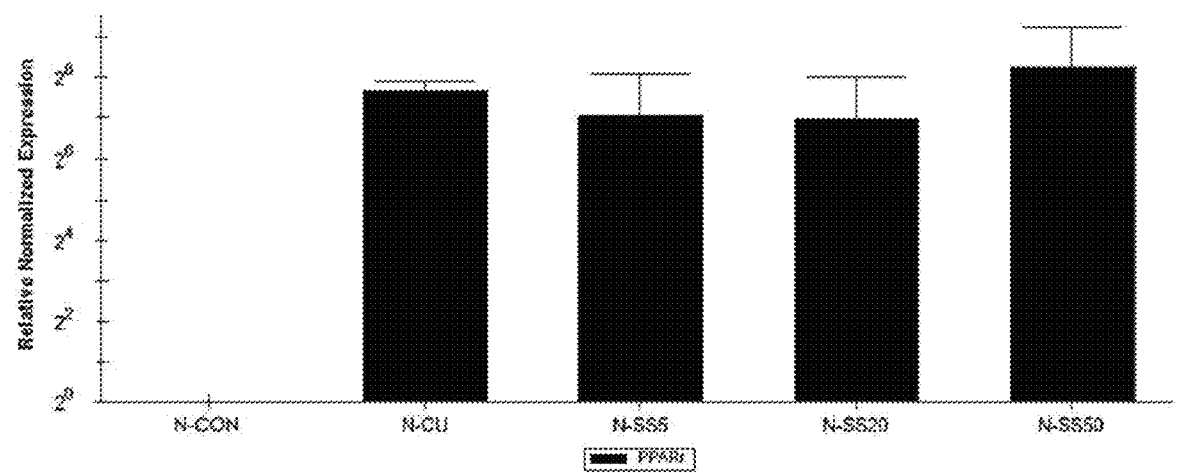
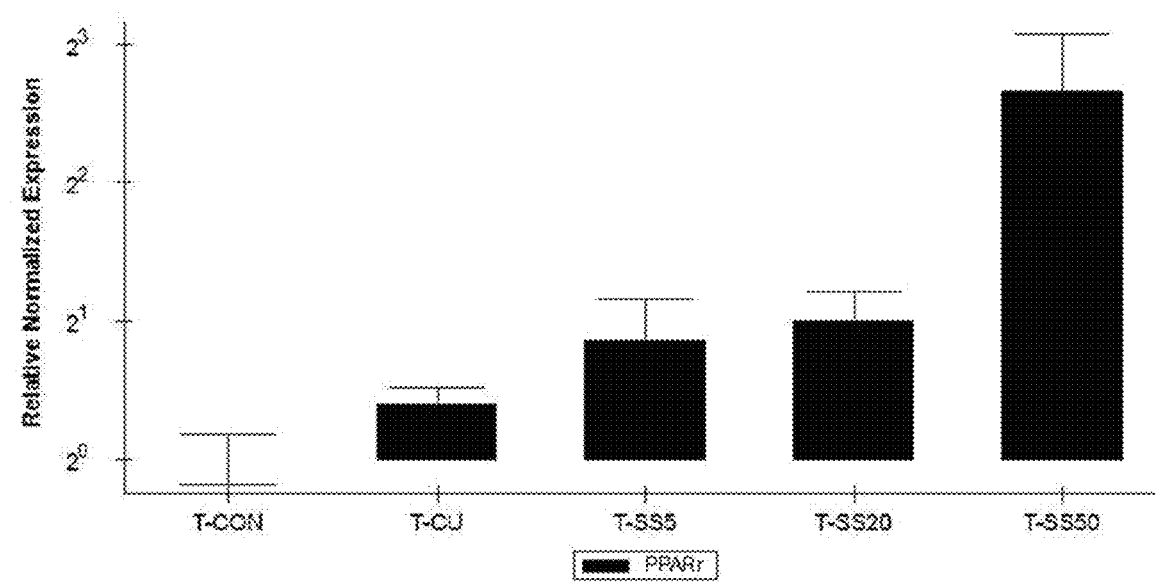
FIG. 17B

FIG. 18A
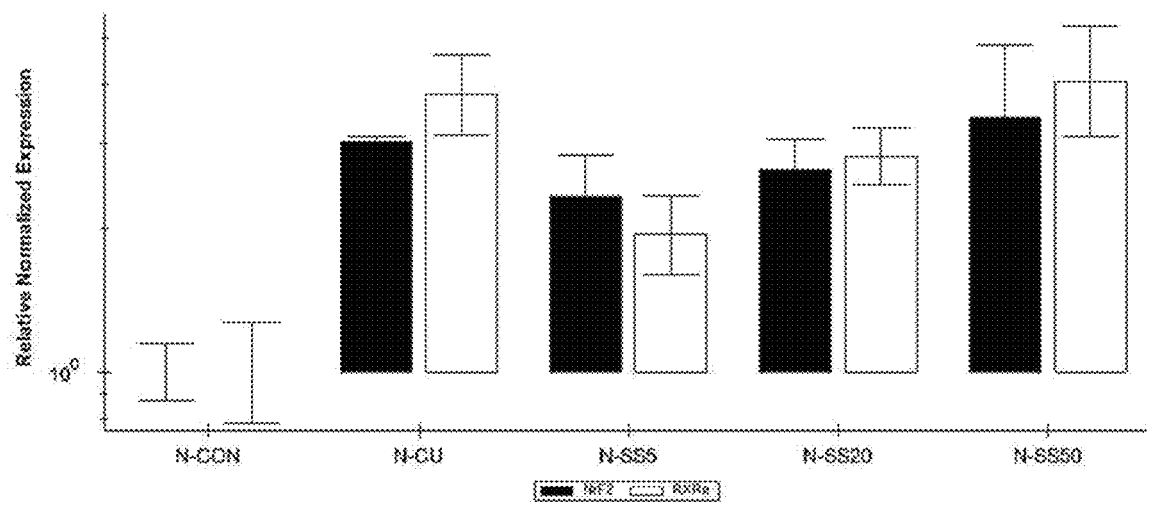
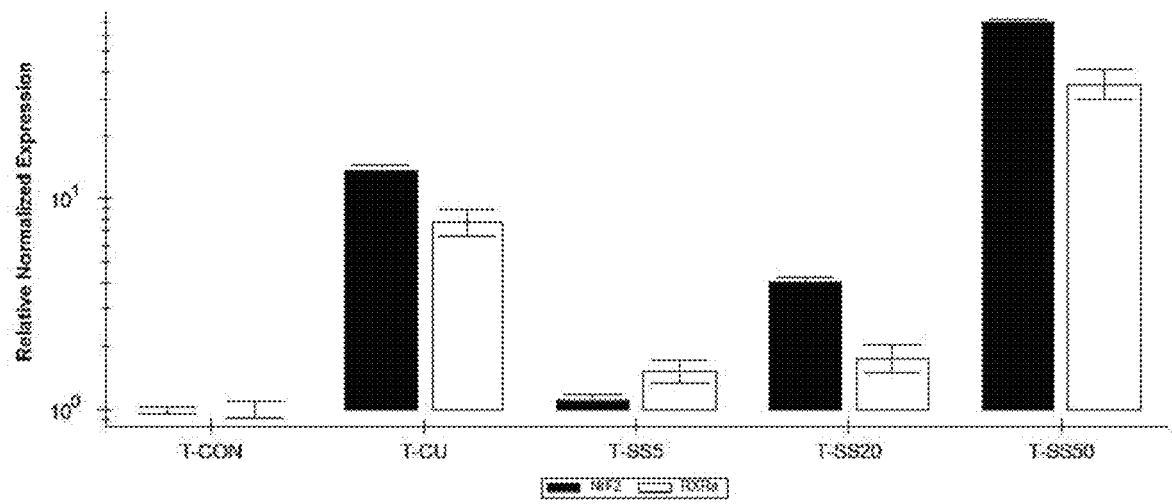
FIG. 18B

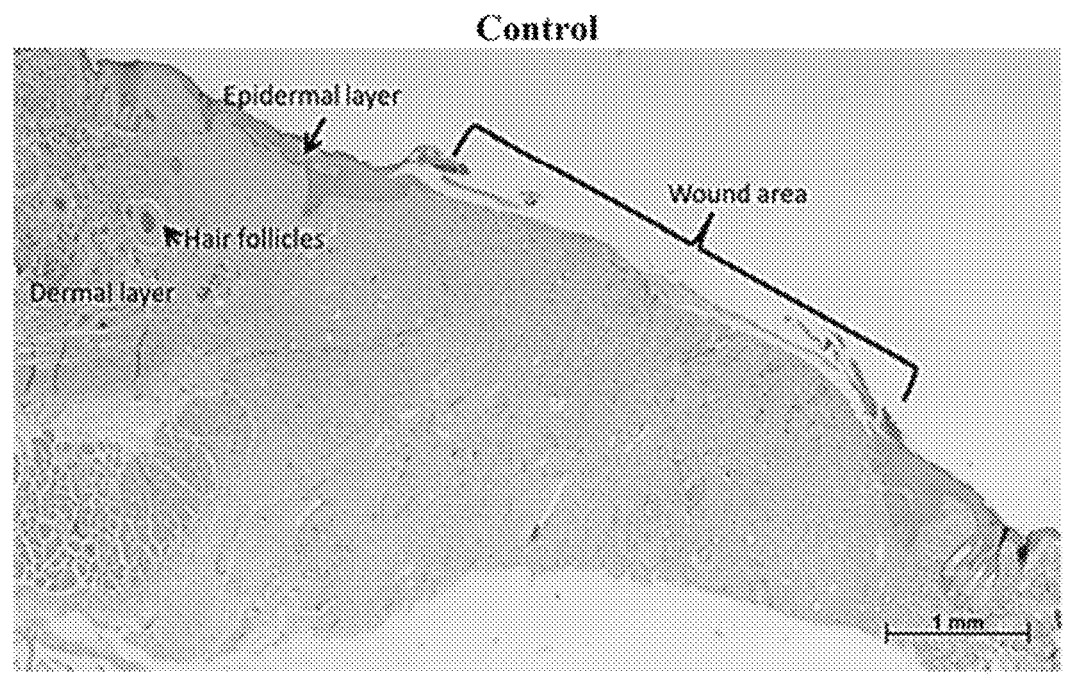
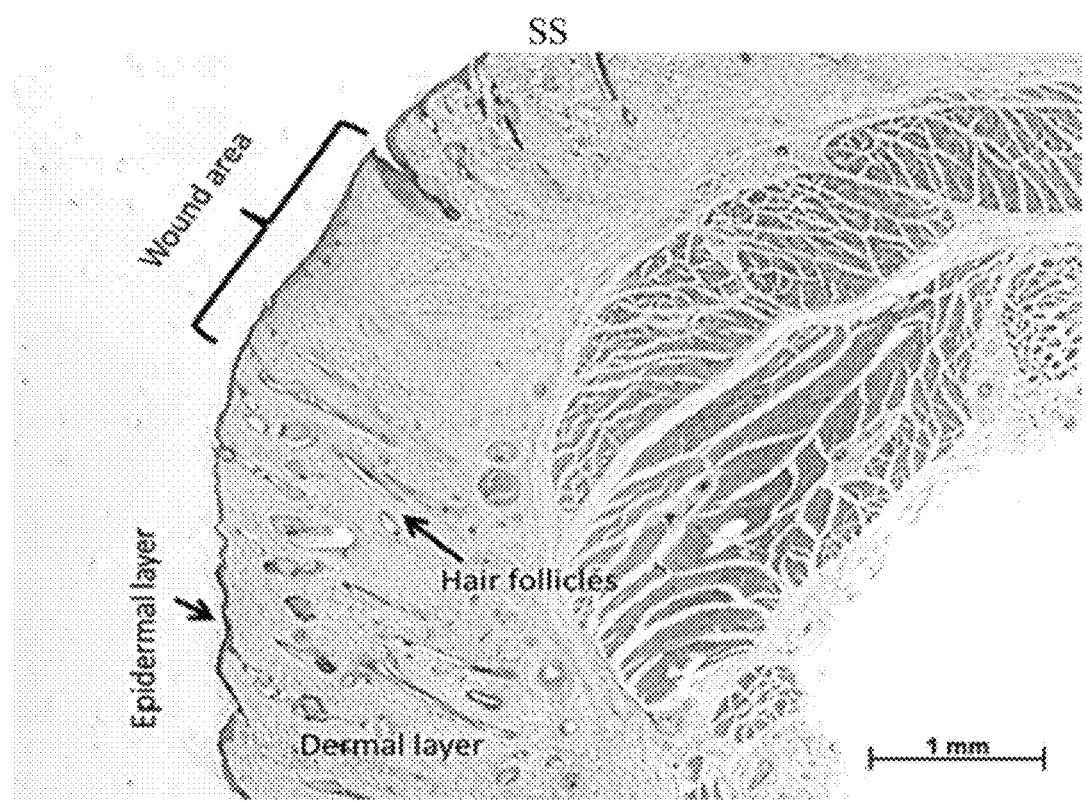
FIG. 22A

SEQUENCE LISTING

<160> NUMBER OF SEQ ID NOS: 28

<210> SEQ ID NO 1
<211> LENGTH: 22
<212> TYPE: DNA
<213> ORGANISM: Artificial Sequence
<220> FEATURE:

<223> OTHER INFORMATION: beta-actin Forward

<400> SEQUENCE: 1
agtggtacga ccagaggcat ac                                        22

<210> SEQ ID NO 2
<211> LENGTH: 22
<212> TYPE: DNA
<213> ORGANISM: Artificial Sequence
<220> FEATURE:
<223> OTHER INFORMATION: beta-actin Reverse

<400> SEQUENCE: 2
atgggtcaga aggactccta cg                                        22

<210> SEQ ID NO 3
<211> LENGTH: 18
<212> TYPE: DNA
<213> ORGANISM: Artificial Sequence
<220> FEATURE:
<223> OTHER INFORMATION: iNOs Forward

<400> SEQUENCE: 3
tcctacacca caccaaac                                             18

<210> SEQ ID NO 4
<211> LENGTH: 19
<212> TYPE: DNA
<213> ORGANISM: Artificial Sequence
<220> FEATURE:
<223> OTHER INFORMATION: iNOs Reverse

<400> SEQUENCE: 4
ctccaatctc tgcctatcc                                            19

<210> SEQ ID NO 5
<211> LENGTH: 18
<212> TYPE: DNA
<213> ORGANISM: Artificial Sequence
<220> FEATURE:
<223> OTHER INFORMATION: TNF alpha Forward

<400> SEQUENCE: 5
aaccctctgg cccaagga                                             18

<210> SEQ ID NO 6
<211> LENGTH: 18
<212> TYPE: DNA
<213> ORGANISM: Artificial Sequence
<220> FEATURE:
<223> OTHER INFORMATION: TNF alpha Reverse

<400> SEQUENCE: 6
ggcgacgggc ttatctga                                             18

<210> SEQ ID NO 7
<211> LENGTH: 21
<212> TYPE: DNA
<213> ORGANISM: Artificial Sequence
<220> FEATURE:
<223> OTHER INFORMATION: Interleukins IL-6 Forward

<400> SEQUENCE: 7
atgaactccc tctccacaag c                                         21

```
<210> SEQ ID NO 8
<211> LENGTH: 21
<212> TYPE: DNA
<213> ORGANISM: Artificial Sequence
<220> FEATURE:
<223> OTHER INFORMATION: Interleukins IL-6 Reverse

<400> SEQUENCE: 8
tggctttgtc tggattcttt c                                              21

<210> SEQ ID NO 9
<211> LENGTH: 19
<212> TYPE: DNA
<213> ORGANISM: Artificial Sequence
<220> FEATURE:
<223> OTHER INFORMATION: Interleukins IL-1 beta Forward

<400> SEQUENCE: 9 aaagggact tgaagagag                                                  19

<210> SEQ ID NO 10
<211> LENGTH: 21
<212> TYPE: DNA
<213> ORGANISM: Artificial Sequence
<220> FEATURE:
<223> OTHER INFORMATION: Interleukins IL-1 beta Reverse

<400> SEQUENCE: 10
ctgcttgaga ggtgctgatg t                                              21

<210> SEQ ID NO 11
<211> LENGTH: 21
<212> TYPE: DNA
<213> ORGANISM: Artificial Sequence
<220> FEATURE:
<223> OTHER INFORMATION: NLRP3 Forward

<400> SEQUENCE: 11
gcgtttgttg aggctcacac t                                              21

<210> SEQ ID NO 12
<211> LENGTH: 28
<212> TYPE: DNA
<213> ORGANISM: Artificial Sequence
<220> FEATURE:
<223> OTHER INFORMATION: NLRP3 Reverse

<400> SEQUENCE: 12
tgaagaagat taccgtaaga agtacaga                                       28

<210> SEQ ID NO 13
<211> LENGTH: 21
<212> TYPE: DNA
<213> ORGANISM: Artificial Sequence
<220> FEATURE:
<223> OTHER INFORMATION: Interleukins IL-33 Forward

<400> SEQUENCE: 13
gatgggaaga agctgatggt g                                              21

<210> SEQ ID NO 14
<211> LENGTH: 20
<212> TYPE: DNA
<213> ORGANISM: Artificial Sequence
<220> FEATURE:
<223> OTHER INFORMATION: Interleukins IL-33 Reverse
```

<400> SEQUENCE: 14
ttgtgaagga cgaagaaggc                                          20

<210> SEQ ID NO 15
<211> LENGTH: 20
<212> TYPE: DNA
<213> ORGANISM: Artificial Sequence
<220> FEATURE:
<223> OTHER INFORMATION: 18S Forward

<400> SEQUENCE: 15
acggaccaga gcgaaagcat                                          20

<210> SEQ ID NO 16
<211> LENGTH: 20
<212> TYPE: DNA
<213> ORGANISM: Artificial Sequence
<220> FEATURE:
<223> OTHER INFORMATION: 18S Reverse

<400> SEQUENCE: 16
tgtcaatcct gtccgtgtcc                                          20

<210> SEQ ID NO 17
<211> LENGTH: 22
<212> TYPE: DNA
<213> ORGANISM: Artificial Sequence
<220> FEATURE:
<223> OTHER INFORMATION: PPAR gamma Forward

<400> SEQUENCE: 17
agcatggtgc cttcgctgat gc                                       22

<210> SEQ ID NO 18
<211> LENGTH: 22
<212> TYPE: DNA
<213> ORGANISM: Artificial Sequence
<220> FEATURE:
<223> OTHER INFORMATION: PPAR gamma Reverse

<400> SEQUENCE: 18
aagttggtgg gccagaatgg ca                                       22

<210> SEQ ID NO 19
<211> LENGTH: 21
<212> TYPE: DNA
<213> ORGANISM: Artificial Sequence
<220> FEATURE:
<223> OTHER INFORMATION: Collagen alpha 1 type III Forward

<400> SEQUENCE: 19
gaaaaaaccc tgctcggaat t                                        21

<210> SEQ ID NO 20
<211> LENGTH: 25
<212> TYPE: DNA
<213> ORGANISM: Artificial Sequence
<220> FEATURE:
<223> OTHER INFORMATION: Collagen alpha 1 type III Reverse

<400> SEQUENCE: 20
ggatcaaccc agtattctcc actct                                    25

<210> SEQ ID NO 21
<211> LENGTH: 19

```
<212> TYPE: DNA
<213> ORGANISM: Artificial Sequence
<220> FEATURE:
<223> OTHER INFORMATION: TGF-beta Receptor 1 Forward

<400> SEQUENCE: 21
catcggcaaa ggtcggttt                                                  19

<210> SEQ ID NO 22
<211> LENGTH: 25
<212> TYPE: DNA
<213> ORGANISM: Artificial Sequence
<220> FEATURE:
<223> OTHER INFORMATION: TGF-beta Receptor 1 Reverse

<400> SEQUENCE: 22
aatatcttca cggcaacttc ttctc                                           25

<210> SEQ ID NO 23
<211> LENGTH: 22
<212> TYPE: DNA
<213> ORGANISM: Artificial Sequence
<220> FEATURE:
<223> OTHER INFORMATION: GF-beta Receptor 2 Forward

<400> SEQUENCE: 23
tcacctacca cggcttcact ct                                              22

<210> SEQ ID NO 24
<211> LENGTH: 20
<212> TYPE: DNA
<213> ORGANISM: Artificial Sequence
<220> FEATURE:
<223> OTHER INFORMATION: TGF-beta Receptor 2 Reverse

<400> SEQUENCE: 24 cgccctttc ttttccttca                                                  20

<210> SEQ ID NO 25
<211> LENGTH: 18
<212> TYPE: DNA
<213> ORGANISM: Artificial Sequence
<220> FEATURE:
<223> OTHER INFORMATION: RXR alpha Forward

<400> SEQUENCE: 25
gccggcctct gactgtga                                                   18

<210> SEQ ID NO 26
<211> LENGTH: 20
<212> TYPE: DNA
<213> ORGANISM: Artificial Sequence
<220> FEATURE:
<223> OTHER INFORMATION: RXR alpha Reverse

<400> SEQUENCE: 26
gcaccacaat gtcccagtga                                                 20

<210> SEQ ID NO 27
<211> LENGTH: 25
<212> TYPE: DNA
<213> ORGANISM: Artificial Sequence
<220> FEATURE:
<223> OTHER INFORMATION: NrF2 Forward

<400> SEQUENCE: 27
```

```
gacaaacatt caagccgatt agagg                                          25
```

<210> SEQ ID NO 28
<211> LENGTH: 24
<212> TYPE: DNA
<213> ORGANISM: Artificial Sequence
<220> FEATURE:
<223> OTHER INFORMATION: NrF2 Reverse

<400> SEQUENCE: 28

```
actttattct tccctctcct gcgt                                           24
```

METHOD OF PROMOTING WOUND HEALING WITH SINETIRUCALLOL

CROSS-REFERENCE

This application is a divisional of U.S. patent application Ser. No. 15/655,530, filed Jul. 20, 2017, which is a continuation application of International Patent Application No. PCT/US2015/048192, filed Sep. 2, 2015, which application claims the benefit of U.S. Provisional Application No. 62/106,177, filed Jan. 21, 2015; and also claims the benefit of Taiwan Application No. TW104107161, filed Mar. 6, 2015; which applications are incorporated herein by reference.

BACKGROUND

Inflammation is a complex biological response of vascular tissues to harmful stimuli, such as pathogens, damaged cells, or irritants. The classical signs of acute inflammation are pain, heat, redness, swelling, and loss of function (Lin et al., Biological evaluation of subglutinol a as a novel immunosuppressive agent for inflammation intervention." ACS Med Chem Lett 5(5), 485-490, 2014). Inflammation is a protective attempt by the organism to remove the injurious stimuli and to initiate the healing process (Fandino-Vaquero et al., "Orosomucoid secretion levels by epicardial adipose tissue as possible indicator of endothelial dysfunction in diabetes mellitus or inflammation in coronary artery disease." Atherosclerosis 235(2): 281-288, 2014). However, it is also noted that inflammation may also be harmful to a subject if it is out of control, for example, in an allergy response. Moreover, overly (exuberant) wound healing usually happens from the recovery of severe and out-of-control inflammation, which may result in fibrosis in tissues and then lead to carcinogenesis.

Liver fibrosis is a typical example of exuberant wound healing. Liver fibrosis occurs during inflammation of liver tissue and is recognized to be involved in cirrhosis and liver cancer. Although inflammation is parts of the defense mechanism of immune system, it is important to appropriately reduce the degree of inflammation in necessary. Liver fibrosis is scarring process, on behalf of the liver damage response. Liver fibrosis is overly (exuberant) wound healing in which excessive connective tissue builds up in the liver. The extracellular matrix (ECM) is overproduced, degraded deficiently, or both. Over time this process can lead to the cirrhosis of liver and severe complications might occur including portal hypertension, liver failure, and liver cancer.

Attempts to treat inflammation and autoimmune disorders have met with limited success. This is due, in part, to the fact that the etiology of inflammation and autoimmune disorders is a complex response based in part on the various inflammation-inducing molecules and the multitude of inflammation-mediating and -sensitizing molecules that appear to elicit inflammation via redundant mechanisms. Therefore, compounds, compositions, and methods that can treat inflammation, neurodegenerative disease, or an autoimmune disorder would be highly desirable.

SUMMARY

In view of the foregoing, there exists a need for improved compounds for treating inflammation, neurodegenerative diseases, and autoimmune disorders. This disclosure provides compounds, compositions, and methods that address this need, and provide other advantages as well.

In one aspect, the disclosure provides a composition formulated for administration to a subject. In some embodiments, the composition comprises sinetirucallol in an amount effective in reducing an inflammatory response. In some embodiments, the composition comprises at least 4.4 µg of sinetirucallol, such as between 4.4 µg and 44 µg of sinetirucallol. In some embodiments, the composition comprises a *Spiranthes sinensis* extract. In some embodiments, reducing an inflammatory response is evidenced by a reduction in expression or activity of one or more biological markers selected from the group consisting of: inducible nitric oxide synthase (iNOS), cyclooxygenase-2 (COX-2), tumor necrosis factor-alpha (TNF-α), prostaglandin E2 (PGE2), interleukin-6 (IL-6), interleukin-1β (IL-1β), interleukin 33 (IL-33), NLRP3, phosphorylated ERK (pERK), NFκB, matrix metalloproteinase-2 (MMP2), and matrix metalloproteinase-9 (MMP9). In some embodiments, reducing an inflammatory response is evidenced by a decrease in a level of one or more free radicals in an inflammatory response, such as one or more free radicals selected from the group consisting of: superoxide radical anion ($O_2^-\cdot$), hydrogen peroxide ($H_2O_2$), hydroxyl radical (.OH), singlet oxygen ($^1O_2$), peroxynitrite ($ONOO^-$), nitric oxide (NO), nitrosonium cation ($NO^+$), and nitroxyl anion ($NO^-$). In some embodiments, reducing an inflammatory response is evidenced by a reduction in tissue swelling, such as in a tissue selected from the group consisting of skin, epithelia, synovial tissue, tendons, cartilage, ligaments, bone, muscle, organs, dura, blood vessels, bone marrow, and extracellular matrix.

In one aspect, the disclosure provides a dosage form comprising sinetirucallol formulated for administration to a subject. In some embodiments, the dosage form is formulated for intravenous, intraarterial, oral, parenteral, buccal, topical, transdermal, rectal, intramuscular, subcutaneous, intraosseous, transmucosal, or intraperitoneal administration. In some embodiments, the dosage form is formulated for topical administration. In some embodiments, the dosage form is formulated as a unit dosage in liquid, gel, semi-liquid, semi-solid, or solid form. In some embodiments, the dosage form comprises at least 4.4 µg of sinetirucallol, such as between 4.4 µg and 44 µg of sinetirucallol. In some embodiments, the dosage form comprises a *Spiranthes sinensis* extract. In some embodiments, the dosage form is formulated as a unit dosage, such as a unit dosage formulated as a food, a beverage, or a dietary supplement.

In one aspect, the disclosure provides a pharmaceutical composition. In some embodiments, the pharmaceutical composition comprises (a) an amount of a *Spiranthes sinensis* extract (SSE) present in an amount that is effective in reducing an inflammatory response and (b) a pharmaceutically acceptable carrier. In some embodiments, reducing an inflammatory response is evidenced by a reduction in expression or activity of one or more biological markers selected from the group consisting of: iNOS, COX-2, TNF-α, PGE2, IL-6, IL-1β, IL-33, NLRP3, pERK, NFκB, MMP2, and MMP9. In some embodiments, reducing an inflammatory response is evidenced by a decrease in a level of one or more free radicals in an inflammatory response, such as one or more free radicals selected from the group consisting of: superoxide radical anion ($O_2^-\cdot$), hydrogen peroxide ($H_2O_2$), hydroxyl radical (.OH), singlet oxygen ($^1O_2$), peroxynitrite ($ONOO^-$), nitric oxide (NO), nitrosonium cation ($NO^+$), and nitroxyl anion ($NO^-$). In some embodiments, reducing an inflammatory response is evidenced by a reduction in tissue swelling, such as in a tissue selected from the group consisting of skin, epithelia, synovial tissue, tendons, cartilage, ligaments, bone, muscle, organs, dura, blood vessels, bone marrow, and extracellular matrix. In some embodiments, the *Spiranthes sinensis* extract comprises at least 0.1% sinetirucallol by weight. In some embodiments, 150 g of the *Spiranthes sinensis* extract comprises at least 250 mg of sinetirucallol. In some embodiments, the pharmaceutical composition is formulated for topical administration. In some embodiments, the carrier is compatible with intravenous, intraarterial, oral, parenteral, buccal, topical, transdermal, rectal, intramuscular, subcutaneous, intraosseous, transmucosal, or intraperitoneal administration. In some embodiments, the pharmaceutical composition is formulated as a unit dosage in liquid, gel, semi-liquid, semi-solid, or solid form. In some embodiments, the pharmaceutical composition is formulated as a topical cream.

In one aspect, the disclosure provides a food composition comprising a food carrier and an amount of sinetirucallol, such as at least 44 μg of sinetirucallol. In some compositions, the food composition comprises a *Spiranthes sinensis* extract. In some embodiments, the food composition is packaged as a beverage, a solid food, or a semi-solid food. In some embodiments, the food composition is packaged as a food product selected from the group consisting of a snack bar, cereal product, bakery product, and a dairy product.

In one aspect, the disclosure provides a method of inducing anti-oxidant production. In some embodiments, the method comprises administering to a subject in need thereof a dosage form comprising sinetirucallol, wherein the dosage form is formulated for administration to a subject. In some embodiments, the dosage form is a pharmaceutical composition comprising a pharmaceutically acceptable carrier. In some embodiments, the dosage form comprises a *Spiranthes sinensis* extract.

In one aspect, the disclosure provides a method of reducing an inflammatory response. In some embodiments, the method comprises administering to a subject in need thereof a dosage form comprising sinetirucallol, wherein the dosage form is formulated for administration to a subject. In some embodiments, the dosage form is a pharmaceutical composition comprising a pharmaceutically acceptable carrier. In some embodiments, the dosage form comprises a *Spiranthes sinensis* extract.

In one aspect, the disclosure provides a method of promoting wound healing. In some embodiments, the method comprises administering to a subject in need thereof a dosage form comprising sinetirucallol, wherein the dosage form is formulated for administration to a subject. In some embodiments, the dosage form is a pharmaceutical composition comprising a pharmaceutically acceptable carrier. In some embodiments, the dosage form comprises a *Spiranthes sinensis* extract.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

(FIG. 2A) The change of the swelling index of foot (n=5). The swelling index was calculated by the formula described herein and presented as a ratio based on the swelling index before injection (Day 0). (FIG. 2B) In the area under curve (AUC) was calculated and presented in the bar diagram of 4 days and the swelling index. (FIG. 2C) The paw photo of mice present at Day 2. The values are represent the means±S.E. of three independent experiments. ***$P<0.001$ compared with the CFA alone treated group.

(FIG. 3A) The change of the change in the swelling index of foot (n=5). The swelling index was calculated by the formula described herein and presented as a ratio based on the swelling index before injection (Day 0). Curves, from top to bottom, correspond to the groups indicated in the legend, from top to bottom, respectively. (FIG. 3B) In the area under curve (AUC) was calculated and presented in the bar diagram of 4 days and the swelling index. (FIG. 3C) The paw photo of mice present at Day 2. The values are represent the means±S.E. of three independent experiments. $P<0.01$; *$P<0.001$ compared with the CFA alone treated group.

(FIG. 4A) Gelatin-substrate zymography of blood from CFA-induced inflammation mice. (FIG. 4B) Quant MMP2 and MMP9 from the three cohorts of mice. The blood was collected from CFA-induced mice at Day 4 and serum was applied MMP assay by gelatin-substrate zymography. The values represent the means±S.E. of three independent experiments. $P<0.01$; *$P<0.001$ as compared with CFA group.

(FIG. 7A) Photo of blot, Quantitation of the expression of (FIG. 7B) COX-2, (FIG. 7C) NFκB, and (FIG. 7D) p-ERK, respectively. The values represent the means±S.E. of three independent experiments. *P<0.05; P<0.01; *P<0.001 as compared with 1 μg/mL of LPS group.

(FIG. 8A) Photo of blot, Quantitation of the expression of (FIG. 8B) COX-2, (FIG. 8C) NFκB, and (FIG. 8D) p-ERK, respectively. The values represent the means±S.E. of three independent experiments. *P<0.05; P<0.01; *P<0.001 as compared with 1 μg/mL of LPS group.

FIG. 12A-12B show the results of the Oil Red O staining assay under 240× magnification. (FIG. 12A) NHSCs, untreated, or treated with 5, 20, and 50 μg/mL of *Spiranthes sinensis* extract. (FIG. 12B) THSCs, untreated, or treated with 5, 20, and 50 μg/mL of *Spiranthes sinensis* extract.

FIGS. 15A-15B show the results of the Sirius Red stain in Example 10 under 240× magnification. (FIG. 15A) NHSCs, untreated, or treated with 5, 20, and 50 μg/mL of *Spiranthes sinensis* extract. (FIG. 15B) THSCs, untreated, or treated with 5, 20 and 50 μg/mL of *Spiranthes sinensis* extract. The concentration is based on the volume of the culture medium.

FIGS. 16A-16B show the expression of COL1 I, COL1 III, TGF-β R1, and TGF-β R2 (from left to right in each group of four bars) in both (FIG. 16A) NHSCs and (FIG. 16B) THSCs. 18S is a reference gene in this examination. N-CU25: NHSCs treated with 25 μM of curcumin; N-CON: untreated NHSCs; N-SS5: NHSCs treated with 5 μg/mL of *Spiranthes sinensis* extract; N-SS20: NHSCs treated with 20 μg/mL of *Spiranthes sinensis* extract; N-SS50: NHSCs treated with 50 μg/mL of *Spiranthes sinensis* extract. T-CU25: THSCs treated with 25 μM of curcumin; T-CON: untreated THSCs; T-SS5: THSCs treated with 5 μg/mL of *Spiranthes sinensis* extract; T-SS20: THSCs treated with 20 μg/mL of *Spiranthes sinensis* extract; T-SS50: THSCs treated with 50 μg/mL of *Spiranthes sinensis* extract. The concentration is based on the volume of the culture medium. Data represent the mean±SEM from three separate experiments.

FIGS. 17A-17B show the expression of PPARγ in both (FIG. 17A) NHSCs and (FIG. 17B) THSCs. N-Control: untreated NHSCs; N-SS5: NHSCs treated with 5 μg/mL of *Spiranthes sinensis* extract; N-SS20: NHSCs treated with 20 μg/mL of *Spiranthes sinensis* extract; N-SS50: NHSCs treated with 50 μg/mL of *Spiranthes sinensis* extract. N-CU25: NHSCs treated with 25 μM of curcumin. T-Control: untreated THSCs; T-SS5: THSCs treated with 5 μg/mL of *Spiranthes sinensis* extract; T-SS20: THSCs treated with 20 μg/mL of *Spiranthes sinensis* extract; T-SS50: THSCs treated with 50 μg/mL of *Spiranthes sinensis* extract. THSCs treated with 25 μM of curcumin. The gene expression was normalized by the expression of 18S. The concentration is based on the volume of the culture medium. Data represent the mean±S.E. from three separate experiments.

FIGS. 18A-18B show the expression of RXRα, NrF2 in both (FIG. 18A) NHSCs and (FIG. 18B) THSCs. N-Control: untreated NHSCs; N-SS5: NHSCs treated with 5 μg/mL of *Spiranthes sinensis* extract; N-SS20: NHSCs treated with 20 μg/mL of *Spiranthes sinensis* extract; N-SS50: NHSCs treated with 50 μg/mL of *Spiranthes sinensis* extract. N-CU25: NHSCs treated with 25 μM of curcumin. T-Control: untreated THSCs; T-SS5: THSCs treated with 5 μg/mL of *Spiranthes sinensis* extract; T-SS20: THSCs treated with 20 μg/mL of *Spiranthes sinensis* extract; T-SS50: THSCs treated with 50 μg/mL of *Spiranthes sinensis* extract. THSCs treated with 25 μM of curcumin. The gene expression was normalized by the expression of 18S. The concentration is based on the volume of the culture medium. Data represent the mean±S.E. from three separate experiments.

FIGS. 22A-22B depict the tissue sections of wound areas in control group and SS group rats. (FIG. 22A) Healing of epidermal and dermal layers of skin in the wound area of control group animals. (FIG. 22B) Healing of epidermal and dermal layers of skin in the wound area of SS group animals. Images are shown at 16× magnification.

FIG. 27A-27D illustrate the results of assays for MMP2 activity, showing the inhibitory effect of *Spiranthes sinensis* extract.

DETAILED DESCRIPTION

Figure 1A:
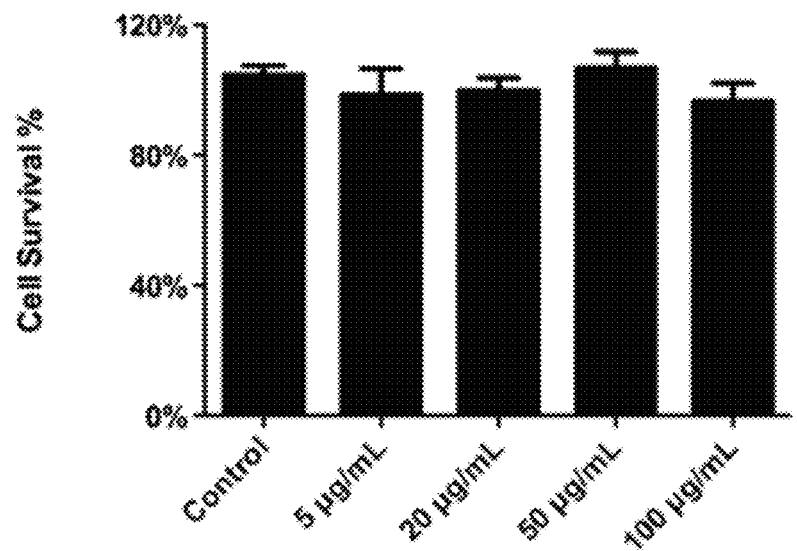
FIGS. 1A-1B depict the lack of cell toxicity of *Spiranthes sinensis* extract. The RAW264.7 cells were treated with various concentrations of (FIG. 1A) *Spiranthes sinensis* extract and (FIG. 1B) SI for 24 h. The cell viability was measured by MTT assay.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the appended claims define the scope of the disclosure and that methods and structures within the scope of these claims and their equivalents be covered thereby.

Unless defined otherwise, all technical and scientific terms used herein have the same meaning as is commonly understood by one of skill in the art to which this disclosure belongs. All patents and publications referred to herein are incorporated by reference.

As used in the specification and claims, the singular form "a", "an" and "the: include plural references unless the context clearly dictates otherwise.

The term "effective amount" or "therapeutically effective amount" refers herein to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reducing an inflammatory response by reducing expression or activity of one or more biological markers such as interleukin-6 (IL-6), NFκB, or phosphorylated ERK (pERK). The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" and "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the composition may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with, "and their grammatical equivalents, as used herein, encompasses administration of two or more agents to an animal so that both agents and/or their metabolites are present in the animal at the same time. Co-administration includes simultaneous administration in separate composition, administration at different times in separate composition, or administration in a composition in which both agents are present.

The term "pharmaceutically acceptable salt" refers herein to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As used herein, "agent" or "biologically active agent" refers herein to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present disclosure.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

As used herein, the term "inhibition" as referred to a biologically active agent refers to the agent's ability to reduce the target signaling activity as compared to off-target signaling activity, via direct or indirect interaction with the target.

As used herein, "subject" refers to an animal, such as a mammal, for example a human. The methods described herein can be useful in both human therapeutics and veterinary applications. In some embodiments, the patient is a mammal, and in some embodiments, the patient is human.

As used herein the term "aberrant immune responses" refers to increased, undesirable, excessive, or inappropriate immune responses in which the immune response to antigens, such as self antigens, is increased such that inflammation and/or autoimmune disease or neurodegenerative disease is seen. Aberrant immune responses, as used herein, are characterized by an immune cascade resulting in destruction of the body's tissue. Typically, an aberrant immune result is not seen in a normal response to infection but can be triggered by infection. Non-limiting examples of aberrant immune responses include auto-immune disorders, immunodeficiency and allergies.

As described herein the term "inflammation", "inflammatory response" or "immune response" is meant the reaction of living tissues to injury, infection or irritation characterized by redness, warmth, swelling, pain, and loss of function, produced as the result of increased blood flow and an influx of immune cells and secretions.

The term "scar tissue" is meant the fibrous (fibrotic) connective tissue that forms at the site of injury or disease in any tissue of the body, caused by the overproduction of disorganized collagen and other connective tissue proteins, which acts to patch the break in the tissue.

The term "regeneration" is meant the renewal, re-growth, or restoration of a body or a bodily part, tissue, or substance after injury or as a normal bodily process.

As used herein a "stem cell" is an undifferentiated cell found among differentiated cells in a tissue or organ, or introduced from an external source for e.g., embryonic stem cells, Adult Bone Marrow stem cells, that can renew itself and differentiate to yield one or more different cell types.

As used herein the terms "free radical" and "free radical derivatives" encompass molecules that are considered to be reactive oxygen species (ROS) and/or reactive nitrogen species (RNS). ROS include both radical and nonradical species formed as a result of the partial reduction of molecular oxygen (dioxygen; $O_2$). Non-limiting examples of ROS include superoxide radical anion ($O_2^-$.), hydrogen peroxide ($H_2O_2$), hydroxyl radical (.OH), singlet oxygen ($^1O_2$), and peroxynitrite ($ONOO^-$). RNS include both radical and non-radical species formed as a result of the oxidation of L-arginine. Non-limiting examples of RNS include nitric oxide (.NO), nitrosonium cation ($NO^+$), nitroxyl anion ($NO^-$), and peroxynitrite ($ONOO^-$).

As described herein a biological marker, or a biomarker, generally refers to a measurable indicator of some biological state or condition. Biological markers are often measured and evaluated to examine normal biological processes, pathogenic processes, or pharmacologic responses to a therapeutic intervention.

An "extract" is a substance made by extracting a part a part of a raw material, often by using a solvent such as ethanol or water. An extract can be in liquid, solid, semi-solid, gel or powder form.

As described herein "beverages" are liquids specifically prepared for human consumption. A beverage typically has some form of water in them. Examples of beverages include water, milk, tea, coffee, juice and juice drinks, soft drinks, and carbonated drinks.

A "dietary supplement" is intended to provide nutrients that may otherwise not be consumed in sufficient quantities. Supplements as generally understood include vitamins, minerals, fiber, fatty acids, or amino acids, among other substances. U.S. authorities define dietary supplements as foods, while elsewhere they may be classified as drugs or other products.

In various aspects, the present disclosure relates to compounds, composition, and methods for treating an individual suffering from diseases associated with aberrant immune responses, such as autoimmune disorders including medication conditions associated with acute and/or chronic inflammation disorders, liver fibrosis, and neurodegenerative disorders. In some embodiments, this is accomplished by administering a therapeutically effective amount of sinetirucallol or composition comprising extract of *Spiranthes sinensis* to an individual suffering from the diseases. In some embodiments, the effective amount of sinetirucallol and/or extract of *Spiranthes sinensis* have anti-inflammatory, anti-liver fibrosis, and anti-oxidation activities.

Composition

In one aspect, the disclosure provides pharmaceutical composition formulated for administering to a subject in need thereof the composition comprising sinetirucallol (SI) in an amount effective to reduce an inflammatory response. In some embodiments, the pharmaceutical composition comprises sinetirucallol, wherein the sinetirucallol has the following chemical structure:

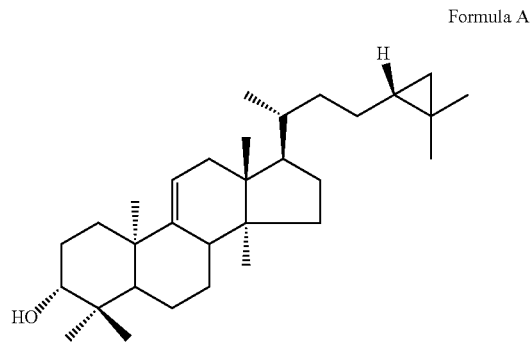

Formula A

Figure 23:
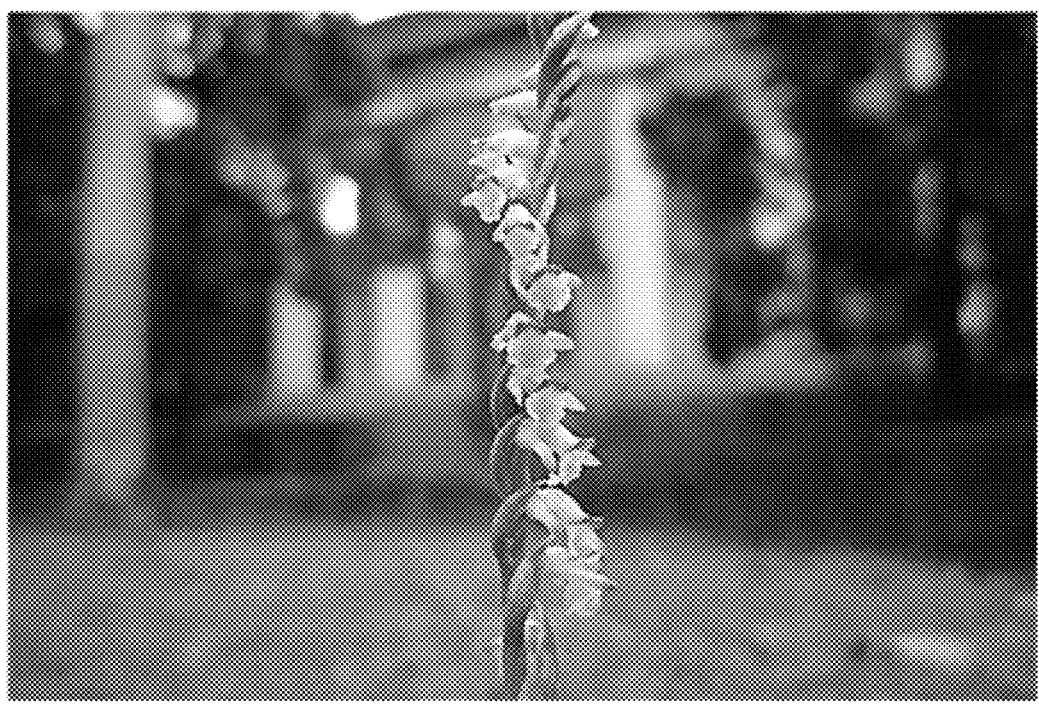
FIG. 23 depicts a *Spiranthes sinensis* plant.

In some embodiments, the disclosed composition comprises a *Spiranthes sinensis* extract (SSE) from the plant *Spiranthes sinensis*. A *Spiranthes sinensis* plant is depicted in FIG. 23.

Extract

In some embodiments, the subject composition comprises sinetirucallol separated from an extract of the plant *Spiranthes sinensis*. In some embodiments, an extract of *Spiranthes sinensis* is provided. In some embodiments, said extract is an ester extract prepared as a method comprising the following steps: (a) obtaining a plant of *Spiranthes sinensis*; (b) mixing said plant with a solvent to obtain a fluid (e.g. a liquid or supercritical fluid); and (c) drying said fluid to obtain said ester extract of *Spiranthes sinensis*.

The plant *Spiranthes sinensis* may be the whole plant or any part of the organism *Spiranthes sinensis* including, but not limited to, the fresh or dried leaves, roots, seeds, bark, fruit, peel, flowers, and/or stem of said plant. In some embodiments, the plant of *Spiranthes sinensis* is dried before being proceed to the extraction steps. In some embodiments, the plant of *Spiranthes sinensis* is dried and ground into proper size to increase the effectiveness of the interaction between said plant and a solvent.

In some embodiments, the *Spiranthes sinensis* extract is prepared by obtaining a plant of *Spiranthes sinensis* and mixing said plant with a solvent to obtain a mixture, followed by drying said mixture to obtain an extract. In some cases, a solvent is ethyl acetate, acetone, and/or n-hexane. In some embodiments, the solvent is ethyl acetate. In some cases, the ethyl acetate is at a concentration of a range between about 1% to 100% (v/v), 5% to 100% (v/v), 15% to 100% (v/v), 20% to 100% (v/v), 25% to 100% (v/v), 30% to 100% (v/v), 40% to 100% (v/v), 50% to 100% (v/v), 60% to 100% (v/v), 70% to 100% (v/v), 80% to 100% (v/v), 90% to 100% (v/v), 10% to 90% (v/v), 20% to 80% (v/v), 30% to 70% (v/v), 40% to 60% (v/v), or 25% to 75% (v/v), wherein said concentration is based on the total volume of ethyl acetate. In some cases, the solvent is ethyl acetate at a concentration of between about 5% to 100% (v/v). In some cases, the ethyl acetate is at a concentration of between about 10% to 100% (v/v).

In some embodiments, the composition is prepared by mixing extract of *Spiranthes sinensis* with a solvent at the temperature between about 15° C. to 30° C., 20° C. to 30° C., 25° C. to 30° C., 18° C. to 28° C., 20° C. to 28° C., 25° C. to 28° C., 15° C. to 37° C., 18° C. to 37° C., 20° C. to 37° C., or 25° C. to 37° C. In some cases, the mixing is conducted at 20° C. to 28° C. In some cases, the mixing is conducted for approximately 1 day, 2 days, 3 days, 5 days, 6 days, 7 days or more. In some cases, the mixing is conducted for approximately 1 to 2 days.

Preparations may further include drying the mixture of *Spiranthes sinensis* extract with a solvent. Numerous methods for drying are available, for example, drying of the mixture can be achieved by vacuum drying, freeze-drying, lyophilization, or combinations thereof. In some embodiments, the extract is in the form of powder after said drying.

The amounts of sinetirucallol and *Spiranthes sinensis* extract are typically correlated with the dry weight of *Spiranthes sinensis*. For example, the amounts of *Spiranthes sinensis* extract: sinetirucallol: *Spiranthes sinensis* can be at the ratio of about 0.3:0.1:1 (w/w/w), about 3:1:10 (w/w/w), about 0.5:0.3:2 (w/w/w), or about 5:3:20 (w/w/w). As a non-unlimited example, approximately 250 mg of sinetirucallol can be separated from approximately 150 g of *Spiranthes sinensis* extract extracted from approximately 1000 g dry weight of *Spiranthes sinensis*. In some embodiments, the amount of sinetirucallol is at least about 250 mg. In some embodiments, the amount of *Spiranthes sinensis* extract is at least about 150 g.

In some embodiments, the composition comprises an amount of *Spiranthes sinensis* extract between about 0.0001 to 1000, 0.001 to 100, 0.01 to 100, 0.1 to 100, 1 to 100, 1.2 to 100, 1.5 to 100, 1.8 to 100, 2 to 100, 3 to 100, 4 to 100, 5 to 100, 6 to 100, 7 to 100, 8 to 100, 9 to 100, 10 to 100, 30 to 1000, 50 to 1000, 80 to 1000 μg/mL, based on the total volume of said pharmaceutical composition. In some embodiments, the pharmaceutical composition comprises an amount of *Spiranthes sinensis* extract at the amount of about or at least about 0.0001, 0.001, 0.01, 0.1, 1, 1.2, 1.5, 1.8, 2, 3, 4, 5, 6, 7, 8, 9, 10, 30, 50, 100, 150, 200, 250, 500 μg/mL or more, based on the total volume of said pharmaceutical composition.

In some embodiments, the amount of sinetirucallol or *Spiranthes sinensis* extract in the composition of the present disclosure is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the amount of sinetirucallol or *Spiranthes sinensis* extract is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the amount of sinetirucallol and/or *Spiranthes sinensis* is in the range of 0.0001-1000 g, 0.001-10 g, 0.005-100 g, 0.0005-9 g, 0.001-8 g, 0.005-7 g, 0.01-6 g, 0.05-5 g, 0.1-4 g, 0.5-4 g, or 1-3 g. In some embodiments, the amount of sinetirucallol and/or *Spiranthes sinensis* is at least about 0.0001, 0.001, 0.005, 0.01, 0.05, 0.1, 1, 3, 4, 5, 6, 7, 8, 9, 10, 100, 1000 g or more.

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending medical profession.

In some embodiments, the present disclosure comprises administering an effective amount of a *Spiranthes sinensis* extract to a subject at the range of between about 1 to about 100 mg per kg body weight per day. An effective dosage can be in the range of about 0.1 to 80, 0.5 to 80, 1 to 80, 10 to 80, 20 to 80, 50 to 80, 0.1 to 10, 0.5 to 10, 1 to 100, 10 to 100, 20 to 100, or 50 to 100 mg per kg body weight per day. As non-limiting examples, an effective dosage can be about 0.01 to 1.0 mg per kg per body weight per day, or 0.06 to 5 mg per kg body weight per day. As another non-limited example, an effective dosage can be about 0.6-5 mg/60 kg/day, in single or divided doses. In some cases, the amount of a *Spiranthes sinensis* extract administered to an subject is between about 0.6-5 mg/60 kg body weight/day.

Formulation

In some embodiments, the composition is formulated for administering to a subject in need thereof wherein the composition comprises sinetirucallol in an amount effective to reduce an inflammatory response. The composition is formulated in dosage form. In some embodiments, the composition is formulated in dosage form comprising sinetirucallol. In some embodiments, the composition is formulated in dosage form comprising an extract of *Spiranthes sinensis*.

In some embodiments, the composition comprises between about 0.001 to 1000 mg, 0.01 to 100 mg, 0.1 to 200 mg, 3 to 200 mg, 5 to 500 mg, 10 to 100 mg, 10 to 1000 mg, 50 to 200 mg, or 100 to 1000 mg of sinetirucallol. In some embodiments, the pharmaceutical composition comprises about or more than about 0.001 μg, 0.01 μg, 0.1, 0.5 μg, 1 μg, 2 μg, 3 μg, 4 μg, 5 μg, 6 μg, 7 μg, 8 μg, 9 μg, 10 μg, 15 μg, 20 μg, 25 μg, 50 μg, 75 μg, 100 μg, 200 μg, 500 μg, 1000 μg, or more of sinetirucallol. In some embodiments, the pharmaceutical composition comprises at least about 4.4 μg of sinetirucallol. In some embodiments, the pharmaceutical composition comprises an amount between about 4.4-44 μg of sinetirucallol.

In some embodiments, the composition is formulated to provide a therapeutically effective amount of a compound of the present disclosure as the active ingredient, or a pharmaceutically acceptable salt, ester, prodrug, solvate, hydrate or derivative thereof. Where desired, the pharmaceutical composition contains a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject composition disclosed herein can be formulated for administration via oral, intravenous injection, and/or topical. In some embodiments, the disclosed pharmaceutical composition is formulated for topical administration.

In some embodiments, the composition further comprises a carrier compatible with intravenous, intraarterial, oral, parenteral, buccal, topical, transdermal, rectal, intramuscular, subcutaneous, intraosseous, transmucosal, inhalation, or intraperitoneal administration.

In some embodiments, the composition is formulated as a unit dosage in liquid, gel, semi-liquid, semi-solid, and/or solid form.

In some embodiments, the composition is formulated as a topical cream.

In some embodiments, the composition is formulated in a food. In some embodiments, the composition is formulated in a beverage. In some embodiments, the composition is formulated in a dietary supplement.

Dosage Unit

In one aspect, the disclosure provides a dosage form comprising sinetirucallol formulated for administration to a subject. In some embodiments, the dosage form is formulated as a unit dosage form. In some embodiments, the composition is formulated in a unit dosage form in liquid, gel, semi-liquid, semi-solid, or solid form. In some embodiments, the unit dosage form can be formulated as a food, a beverage, a semi-solid food, a semi-liquid food, and/or a dietary supplement. In some aspects, the dosage form comprises an amount of a *Spiranthes sinensis* extract (SSE) or sinetirucallol present in an amount that is effective in reducing an inflammatory response. In some embodiments, the pharmaceutical composition further comprises a pharmaceutically acceptable carrier.

In some embodiments, the dosage form comprises sinetirucallol extracted in an amount of between about 0.1 to 1000 µg, 0.1 to 5 µg, 0.1 to 10 µg, 0.1 to 20 µg, 0.1 to 30 µg, 0.1 to 40 µg, 0.1 to 50 µg, 0.1 to 100 µg, 0.5 to 100 µg, 1 to 100 µg, 5 to 100 µg, 10 to 100 µg, 20 to 100 µg, or 50 to 100 µg. In some embodiments, the dosage form comprises at least about or more than about 0.1 µg, 5 µg, 10 µg, 20 µg, 30 µg, 40 µg, 50 µg, 100 µg, 1000 µg, or more of sinetirucallol. In some embodiments, the dosage amount of sinetirucallol is between about 4.4 µg to 44 µg. In some embodiments, the amount of sinetirucallol is at least about 4.4 µg. In some embodiments, the unit dosage comprises a *Spiranthes sinensis* extract. In some embodiments, the amount of *Spiranthes sinensis* extract is least about 44 µg.

In some embodiments µg/mL, the unit dosage form comprises *Spiranthes sinensis* extract in an amount of between about 0.1 to 1000 µg/mL, 0.1 to 100 µg/mL, 0.5 to 100 µg/mL, 1 to 100 µg/mL, 2 to 100 µg/mL, 5 to 100 µg/mL, 10 to 100 µg/mL, 20 to 100 µg/mL, 50 to 100 µg/mL, 0.1 µg to 150 µg/mL, 0.5 to 150 µg/mL, 1 to 150 µg/mL, 2 to 150 µg/mL, 5 to 150 µg/mL, 10 to 150 µg/mL, 20 to 150 µg/mL, 50 to 150 µg/mL, 0.1 to 200 µg/mL, 0.5 to 200 µg/mL, 1 to 200 µg/mL, 2 to 200 µg/mL, 5 to 200 µg/mL, 10 to 200 µg/mL, 20 to 200 µg/mL, or 50 to 1000 µg/mL, based on the total volume of said pharmaceutical composition. In some embodiments, the unit dosage amount of *Spiranthes sinensis* extract is at least about or more than about 0.1 µg/mL, 1 µg/mL, 2 µg/mL, 5 µg/mL, 10 µg/mL, 20 µg/mL, 50 µg/mL, 100 µg/mL, 150 µg/mL, 200 µg/mL, 500 µg/mL, 1000 µg/mL or more. In some embodiments, the disclosed composition comprises between about 5 to 100 µg/mL of *Spiranthes sinensis* extract.

The amount of the compound administered will be dependent on the mammal being treated, the severity of the disorder or condition, the rate of administration, the disposition of the compound and the discretion of the prescribing medical profession. In some embodiments, a compound of the disclosure is administered in a single dose. A single dose of a compound of the disclosure may also be used for treatment of an acute condition. In some embodiments, a compound of the disclosure is administered in multiple doses. Dosing may be about once, twice, three times, four times, five times, six times, or more than six times per day. Dosing may be about once a month, once every two weeks, once a week, or once every other day. In another embodiment a compound of the disclosure and another agent are administered together about once per day to about 6 times per day. In another embodiment the administration of a compound of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the disclosure may continue as long as necessary. In some embodiments, an agent of the disclosure is administered for more than 1, 2, 3, 4, 5, 6, 7, 14, 28 days or more. In some embodiments, an agent of the disclosure is administered for less than 28, 14, 7, 6, 5, 4, 3, 2, or 1 day. In some embodiments, an agent of the disclosure is administered chronically on an ongoing basis, e.g., for the treatment of chronic effects.

An effective amount of a compound of the disclosure may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

When a compound of the disclosure is administered in a composition that comprises one or more agents, and the agent has a shorter half-life than the compound of the disclosure unit dose forms of the agent and the compound of the disclosure may be adjusted accordingly.

For treatment of autoimmune diseases, the subject compounds or pharmaceutical composition can be used in combination with commonly prescribed drugs including but not limited to Enbrel®, Remicade®, Humira®, Avonex®, and Rebif®. For treatment of respiratory diseases, the subject compounds or pharmaceutical composition can be administered in combination with commonly prescribed drugs including but not limited to Xolair®, Advair®, Singulair®, and Spiriva®.

The compounds of the disclosure may be formulated or administered in conjunction with other agents that act to relieve the symptoms of inflammatory conditions such as encephalomyelitis, asthma, and the other diseases described herein. These agents include nonsteroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

The compounds describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein for use in combination with composition comprising sinetirucallol may include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include may drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants may be contemplated by the methods herein. In addition, therapeutic agents acting on the blood and the blood-forming organs, hematopoietic agents, growth factors, minerals, and vitamins, anticoagulant, thrombolytic, and antiplatelet drugs may be contemplated by the methods herein.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein, including sinetirucallol and *Spiranthes sinensis* extract, can be used in combination with one or more other agents, depending on the condition being treated. Hence, in some embodiments the compounds of the disclosure will be co-administered with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present disclosure and any of the agents described above can be simultaneously administered, wherein both the agents are present in separate formulations. In another alternative, a compound of the present disclosure can be administered just followed by and any of the agents described above, or vice versa. In the separate administration protocol, a compound of the present disclosure and any of the agents described above may be administered a few minutes apart, or a few hours apart, or a few days apart.

The amount of the compound administered will be dependent on the mammal being treated, the severity of the disorder or condition, the rate of administration, the disposition of the compound and the discretion of the prescribing physician. However, an effective dosage can be in the range of about 1 to about 100 mg per kg body weight per day. An effective dosage can be in the range of about 0.1 to 80, 0.5 to 80, 1 to 80, 10 to 80, 20 to 80, 50 to 80, 0.1 to 10, 0.5 to 10, 1 to 100, 10 to 100, 20 to 100, or 50 to 100 mg per kg body weight per day. As a non-limited example, an effective dosage can be about 0.01 kg per body weight to 1.0 kg per body weight per day. As another non-limited example, an effective dosage can be about 0.6-5 mg/60 kg/day, in single or divided doses. For a 120 kg human, this would amount to about 1.2 to 10 mg/day.

Administration of the compounds of the present disclosure can be effected by any method that enables delivery of the compounds to the site of action. An effective amount of a compound of the disclosure may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer. Administration In some embodiments, a composition of the present disclosure, including dosage forms describe herein, is formulated for one or more of the administration routes via intravenous, intraarterial, oral, parenteral, buccal, topical, transdermal, rectal, intramuscular, subcutaneous, intraosseous, transmucosal, inhalation, and/or intraperitoneal administration. In some embodiments, the subject composition is administered via oral administration. In some embodiments, the subject composition is administered via intravenous injection. In some embodiments, the subject composition is administered via a combination of oral administration and intravenous injection. In some embodiments, the subject composition is formulated for topical administration.

The subject composition can be administered alone or in combination with one or more other agents, which are also typically administered in the form of pharmaceutical composition. Where desired, the subject compounds and other agent(s) may be mixed into a preparation or both components may be formulated into separate preparations to use them in combination separately or at the same time.

Administration of the compounds or pharmaceutical composition of the present disclosure can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The composition of the disclosure may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the disclosure may slow or inhibit the migration and proliferation of smooth muscle cells in the arterial wall which contribute to restenosis. A compound of the disclosure may be administered, for example, by local delivery from the struts of a stent, from a stent graft, from grafts, or from the cover or sheath of a stent. In some embodiments, a compound of the disclosure is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (etherester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the disclosure may be applied to the surface of the stent by various methods such as dip/spin coating, spray coating, dip-coating, and/or brush-coating. The compounds may be applied in a solvent and the solvent may be allowed to evaporate, and may form a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the disclosure in a suitable solvent, followed by evaporation of the solvent. Excess drug on the surface of the stent may be removed via an additional brief solvent wash. In yet other embodiments, compounds of the disclosure may be covalently linked to a stent or graft. A covalent linker may be used which degrades in vivo, leading to the release of the compound of the disclosure. Any bio-labile linkage may be used for such a purpose, such as ester, amide or anhydride linkages. Compounds of the disclosure may additionally be administered intravascularly from a balloon used during angioplasty. Extravascular administration of the compounds via the pericard or via advential application of formulations of the disclosure may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The subject composition may, for example, be in a form suitable for oral administration as a tablet, capsule, pill, microspheres, powder, sustained release formulations, solution, suspension for parenteral injection as a sterile solution, suspension or emulsion, for topical administration as an ointment or cream or for rectal administration as a suppository. The composition may be in unit dosage forms suitable for single administration of precise dosages. The composition may include a conventional pharmaceutical carrier or excipient and a compound according to the disclosure as an active ingredient. In addition, it may include other medicinal or pharmaceutical agents, carriers, adjuvants, etc.

Preparations for parenteral administration typically include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate.

Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

When a compound of the disclosure is administered in a composition that comprises one or more agents, and the agent has a shorter half-life than the compound of the disclosure, unit dose forms of the agent and the compound of the disclosure may be adjusted accordingly.

In one aspect, the present disclosure provides a composition comprising an amount of sinetirucallol present in an amount that is effective in reducing an inflammatory response. Administration of the disclosed composition can reduce inflammatory response, decrease in a level of one or more free radicals in an inflammatory response, and/or reduce tissue swelling.

In some embodiments of the disclosure, administration of the composition reduces inflammatory response and causes reduction in expression or activity of one or more biological markers such as iNOS, COX-2, TNF-alpha, PGE2, IL-6, IL-1β, IL-33, NLRP3, pERK, NFκB, MMP2, and MMP9.

Typically, inflammation is the body's reaction to invading infectious microorganisms and generally results in an increase in blood flow to the affected area, the release of chemicals that draw white blood cells, an increased flow of plasma, and the arrival of monocytes (or astrocytes in the case of the brain) to clean up the debris. Anything that stimulates the inflammatory response is said to be inflammatory. A reduction in inflammation can be measured by any suitable method, including methods described herein. A reduction in inflammation can also be measured by a reduction in the expression level of biological markers described herein. Typically, the expression level of biological markers can be achieved by measuring the level of DNA, RNA, gene transcription, and/or protein expression. Examples of common techniques to measure the expression level of biological markers described herein include, PCR, qRT-PCR, microarray, NanoString, RNA-seq, Western blot, and spectrophotometry. In some embodiments, the composition is effective in reducing an inflammatory response by at least about 0.1%, 2%, 5%, 10%, 15%, 20%, 25%, 30%, 50%, 60%, or about 75% to 90% or more.

In some embodiments, administration of the composition decreases a level of one or more free radicals in an inflammatory response. The one or more free radicals that are reduced in response to the administration of said composition can include the group consisting of superoxide radical anion ($O_2^-$), hydrogen peroxide ($H_2O_2$), hydroxyl radical (.OH), singlet oxygen ($^1O_2$), peroxynitrite ($ONOO^-$), nitric oxide (NO), nitrosonium cation ($NO^+$), and nitroxyl anion ($NO^-$).

The effectiveness of said composition in reducing free radical can be measured, for example, by nitrite quantification. In some embodiments, the composition is effective in reducing inflammatory response by at least about 0.1%, 2%, 5%, 10%, 15%, 20%, 25%, 30%, 50%, 60%, or about 75% to 90% or more.

In some embodiments, administration of the composition reduces tissue swelling. Non-limiting examples of tissues in which swelling may be reduced includes skin, epithelia, synovial tissue, tendons, cartilage, ligaments, bone, muscle, organs, dura, blood vessels, bone marrow, and extracellular matrix.

The reduction of tissue swelling can be determined by the change of swelling index. As a non-limiting example, the swelling index can be calculated by dividing the area of the injured limb of an animal by the area of the control uninjured limb of an animal. The swelling index can be presented as a ratio based on the swelling index of the injured and control uninjured limb. In some embodiments, the swelling index of the injured and control uninjured limb prior to and after said administration may be recorded for comparison. As another non-limiting example, inflammation in animal models can be induced by injecting Complete Freund's Adjuvant (CFA) in one paw. The swelling index can be calculated using the formula shown below and can be presented as a ratio based on the swelling index before injection (Day 0). In some embodiments, the composition is effective in reducing tissue swelling by at least about 0.1%, 2%, 5%, 10%, 15%, 20%, 25%, 30%, 50%, 60%, or about 75% to 90% or more.

$$\frac{\text{Length} \times \text{Width of right hindpaw (injected paw)}}{\text{Length} \times \text{Width of left hindpaw (uninjected paw)}}$$

In some embodiments, administration of the composition has anti-liver fibrosis activities. Examples of anti-liver fibrosis include, but are not limited to, indications such as accumulation of lipid in hepatic stellate cells, down-regulation of the proliferation of hepatic stellate cells, inhibitions of the mobility of hepatic stellate cells, prevention of the activation of the hepatic stellate cells, and/or decrease of the synthesis of ECM proteins.

In general, liver fibrosis is a scarring process in response to liver damage. Typically, liver fibrosis is overly or exuberant wound healing in which excessive connective tissue builds up in the liver. The extracellular matrix (ECM) is overproduced, or degraded deficiently, or a combination thereof. Over time, this process can lead to cirrhosis of the liver and may lead to severe complications including portal hypertension, liver failure, and/or liver cancer.

Scars are typically dense and thick, and usually are paler than the surrounding tissue because scars are typically poorly supplied with blood, and although it structurally replaces destroyed tissue, it typically cannot perform all functions of the missing tissue. Scars are typically composed of collagenous fibers, which will often restrict normal elasticity in the tissue involved. A reduction in scar tissue can be assessed by the population of cell types within the injured site. For example, a reduction in scar tissue formation can be measured by a simple measurement of scar width or area of scar tissue (Wilgus et al., 2003). In addition histological assessments can be made about the restoration of structural complexity within healed tissue in comparison to normal tissue. In some embodiments, scar formation can be reduced by at least about 0.1%, 2%, 5%, 10%, 15%, 20%, 25%, 30%, 50%, 60%, or about 75% to 90% or more by a composition disclosed herein, such as a composition or dosage form comprising sinetirucallol.

Pharmaceutical Composition

In one aspect, the disclosure provides a pharmaceutical composition. In some embodiments, the pharmaceutical composition comprises (a) an amount of *Spiranthes sinensis* extract (SSE) or sinetirucallol present in an amount that is effective in reducing an inflammatory response, and (b) a pharmaceutically acceptable carrier. A pharmaceutical composition of the present disclosure typically contains an active ingredient (e.g., a compound of the present disclosure or a pharmaceutically acceptable salt and/or coordination complex thereof), and one or more pharmaceutically acceptable excipients, carriers, including but not limited to, inert solid diluents and fillers, diluents, sterile aqueous solution and various organic solvents, permeation enhancers, solubilizers and adjuvants.

In some embodiments, the disclosure provides a pharmaceutical composition comprising an amount of *Spiranthes sinensis* extract and/or sinetirucallol formulated for administration to a subject in need thereof. In some embodiments, the pharmaceutical composition comprises between about 0.001-1000 mg, 0.01-100 mg, 0.1 to 200 mg, 3 to 200 mg, 5 to 500 mg, 10 to 100 mg, 10 to 1000 mg, 50 to 200 mg, or 100 to 1000 mg of *Spiranthes sinensis* extract and/or sinetirucallol. In some embodiments, the pharmaceutical composition comprises about or more than about 0.001 µg, 0.01 µg, 0.1, 0.5 µg, 1 µg, 2 µg, 3 µg, 4 µg, 5 µg, 6 µg, 7 µg, 8 µg, 9 µg, 10 µg, 15 µg, 20 µg, 25 µg, 50 µg, 75 µg, 100 µg, 200 µg, 500 µg, 1000 µg, or more of *Spiranthes sinensis* extract and/or sinetirucallol. In some embodiments, the pharmaceutical composition comprises at least about 44 µg of *Spiranthes sinensis* extract. In some embodiments, the pharmaceutical composition comprises at least about 44 µg of sinetirucallol. In some embodiments, the pharmaceutical composition comprises an amount between about 4.4-44 µg of *Spiranthes sinensis* extract. In some embodiments, the pharmaceutical composition comprises an amount between about 4.4-44 µg of sinetirucallol. In some embodiments, the pharmaceutical composition comprises at least about 150 g of *Spiranthes sinensis* extract. In some embodiments, the pharmaceutical composition comprises at least about 250 g of sinetirucallol.

In some embodiments, the pharmaceutical composition is formulated for administration to a subject in need thereof. The composition can be formulated for intravenous, intraarterial, oral, parenteral, buccal, topical, transdermal, rectal, intramuscular, subcutaneous, intraosseous, transmucosal, inhalation, and/or intraperitoneal administration. In some embodiments, the composition is formulated for topical administration.

In some embodiments, the pharmaceutical composition is formulated as a unit dosage in liquid, gel, semi-liquid, or solid form. In some embodiments, the pharmaceutical composition is formulated as a topical cream.

In some embodiments, the pharmaceutical composition can be formulated a food, such as a solid food or a semi-solid food. In some embodiments, the composition can be formulated in a beverage. In some embodiments, the composition can be formulated in a dietary supplement.

In some embodiments, the disclosed pharmaceutical composition when administered to a subject in need thereof can reduce an inflammatory response and cause reduction in expression or activity of one or more biological marker. Without bound by any theory, the one or more biological marker includes iNOS, COX-2, TNF-alpha, PGE2, IL-6, IL-1β, IL-33, NLRP3, pERK, NFκB, MMP2, and MMP9.

In some embodiments, the disclosed pharmaceutical composition when administered to a subject in need thereof can decrease in a level of one or more free radicals in an inflammatory response. Without bound by any theory, the one or more free radicals that are reduced in response to the administration of said composition includes the group consisting of superoxide radical anion ($O_2^-$), hydrogen peroxide ($H_2O_2$), hydroxyl radical (.OH), singlet oxygen ($^1O_2$), peroxynitrite ($ONOO^-$), nitric oxide (NO), nitrosonium cation ($NO^+$), and nitroxyl anion ($NO^-$).

In some embodiments, administering the composition disclosed herein can reduce an inflammatory response and reduce tissue swelling. Non-limited examples of reduced tissue swelling includes skin, epithelia, synovial tissue, tendons, cartilage, ligaments, bone, muscle, organs, dura, blood vessels, bone marrow, and extracellular matrix.

In some embodiments, the pharmaceutical composition can be formulated in a unit dosage in liquid, gel, semi-liquid, semi-solid, or solid form.

In some embodiments, the pharmaceutical acceptable carriers, excipients are selected from the group consisting of water, alcohol, glycerol, chitosan, alginate, chondroitin, Vitamin E, mineral oil, and dimethyl sulfoxide (DMSO).

Pharmaceutical Composition for Topical (e.g., Transdermal) Delivery.

In some embodiments, the disclosure provides a pharmaceutical composition for transdermal delivery containing a compound of the present disclosure and a pharmaceutical excipient suitable for transdermal delivery. The composition may be in the form of a solid, liquid, gel, semi-liquid, or semi-solid. In some embodiments, the composition further comprises a second agent.

Composition of the present disclosure can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical composition also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Formulations for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Another exemplary formulation for use in the methods of the present disclosure employs transdermal delivery devices ("patches"). Such transdermal patches may be used to provide continuous or discontinuous infusion of a compound of the present disclosure in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Composition for Oral Administration

In some embodiments, the disclosure provides a pharmaceutical composition for oral administration containing a compound of the present disclosure, and a pharmaceutical excipient suitable for oral administration. The composition may be in the form of a solid, liquid, gel, semi-liquid, or semi-solid. In some embodiments, the composition further comprises a second agent.

Pharmaceutical composition of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, which typically include the step of bringing the active ingredient into association with the carrier. In general, the composition are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical composition and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical composition and dosage forms of the disclosure can be prepared using anhydrous or low moisture containing ingredients and low moisture or low humidity conditions. Pharmaceutical composition and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous composition may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the composition for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical composition and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the composition of the disclosure to provide tablets that disintegrate when exposed to an aqueous environment. Too much of a disintegrant may produce tablets which may disintegrate in the bottle. Too little may be insufficient for disintegration to occur and may alter the rate and extent of release of the active ingredient(s) from the dosage form. A sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical composition and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phytosterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters;

sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, S-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. If present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Composition for Injection.

In some embodiments, the disclosure provides a pharmaceutical composition for injection containing a compound of the present disclosure and a pharmaceutical excipient suitable for injection. Components and amounts of agents in the composition are as described herein.

The forms in which the novel composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Composition for Inhalation.

Compositions for inhalation or insufflation include solutions and suspensions in pharmaceutically acceptable, aqueous or organic solvents, or mixtures thereof, and powders. The liquid or solid composition may contain suitable pharmaceutically acceptable excipients as described supra. Preferably the composition is administered by the oral or nasal respiratory route for local or systemic effect. Composition in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder composition may be administered, preferably orally or nasally, from devices that deliver the formulation in an appropriate manner.

Other Pharmaceutical Composition.

Pharmaceutical compositions may also be prepared to comprise a composition described herein, such as a composition comprising sinetirucalol or a *Spiranthes sinensis* extract, and one or more pharmaceutically acceptable excipients suitable for sublingual, buccal, rectal, intraosseous, intraocular, intranasal, epidural, or intraspinal administration. Excipients and their use in pharmaceutical composition are well-known in the art. See, e.g., See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

In some embodiments, the compositions and methods further comprise administering, separately or simultaneously one or more additional agents (e.g. 1, 2, 3, 4, 5, or more). Additional agents can include those useful in wound healing. Non-limiting examples of additional agents include antibiotics (e.g. Aminoglycosides, Cephalosporins, Chloramphenicol, Clindamycin, Erythromycins, Fluoroquinolones, Macrolides, Azolides, Metronidazole, Penicillin's. Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Ciclopofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

Food

In one aspect, the disclosure provides a food composition comprising a food carrier and an amount of sinetirucallol. The food composition may be a dosage form for the administration of sinetirucallol, such as a dosage form as described herein. In some embodiments, the food composition comprises sinetirucallol between about 0.001 to 1000 mg, 0.01 to 100 mg, 0.1 to 200 mg, 3 to 200 mg, 5 to 500 mg, 10 to 100 mg, 10 to 1000 mg, 50 to 200 mg, or 100 to 1000 mg of sinetirucallol. In some embodiments, the food composition comprises about or more than about 0.001 µg, 0.01 µg, 0.1, 0.5 µg, 1 µg, 2 µg, 3 µg, 4 µg, 5 µg, 6 µg, 7 µg, 8 µg, 9 µg, 10 µg, 15 µg, 20 µg, 25 µg, 50 µg, 75 µg, 100 µg, 200 µg, 500 µg, 1000 µg, or more of sinetirucallol. In some embodiments, the food composition comprises at least about 4.4 µg of sinetirucallol. In some embodiments, the food composition comprises an amount between about 4.4-44 µg of sinetirucallol. In some embodiments, the food composition comprises at least about 44 µg of sinetirucallol. In some embodiments, the food composition comprises a *Spiranthes sinensis* extract.

Packaging of the disclosed food composition can be achieved by any of a variety of suitable methods. For example, the food composition may be packaged as a beverage, a solid food, and/or a semi-solid food. In some cases, the disclosed food composition is packaged as a food product such as one or more forms in the group consisting of a snack bar, cereal product, bakery product, and dairy product.

In some embodiments, the disclosed pharmaceutical composition is packaged in food stuff formulated as a unit dosage. Without being bound by any limitation, the unit dosage is formulated as a beverage, a dietary supplement, a solid food, and/or a semi-solid food.

Treatment

In some aspects, the present disclosure provides pharmaceutical compositions and methods of reducing free radicals, reducing an inflammatory response, and/or promotion of wound healing. In some embodiments, the methods comprise administering to a subject in need thereof a dosage form comprising sinetirucallol formulated for administration to a subject. In some embodiments, the dosage form further comprises a pharmaceutical carrier. In some embodiments, the dosage form comprises a *Spiranthes sinensis* extract. The methods can include administering any of the compositions disclosed herein, such as dosage forms, pharmaceutical compositions, or food compositions. Administration of the composition and measurement of effectiveness are described herein, such as with respect to the various compositions disclosed herein.

As noted above, the present disclosure provides methods for reducing inflammatory response comprising administering to a subject in need thereof a dosage form comprising sinetirucallol. The composition can be any sinetirucallol-containing composition described herein. In one embodiment, the dosage form of sinetirucallol is formulated for administration to a subject. In a related embodiment, the dosage form is a pharmaceutical composition comprising a pharmaceutically acceptable carrier, examples of which are described herein. In a still related embodiment, the dosage form comprises a *Spiranthes sinensis* extract, such as an extract described herein.

In some embodiments, the present disclosure provides the pharmaceutical composition and methods for the treatment of inflammation including but not limited to liver fibrosis. The disclosed composition may be used to provide anti-inflammatory, anti-liver fibrosis, and/or anti-oxidation activities. In some embodiments, the composition comprises an effective amount of sinetirucallol. In some embodiments, the pharmaceutical composition comprises an effective amount of *Spiranthes sinensis* extract. In some embodiments, the pharmaceutical composition further comprises a pharmaceutically acceptable carrier.

In some embodiments, methods provided herein can reduce inflammation in a subject. Typically, inflammation is the body's reaction to invading infectious microorganisms and typically results in an increase in blood flow to the affected area, the release of chemicals that draw white blood cells, an increased flow of plasma, and the arrival of monocytes (or astrocytes in the case of the brain) to clean up the debris. An inflammatory stimulant can be anything that stimulates the inflammatory response. In some embodiments, in addition to reducing inflammation in a subject in response to tissue injury, the provided compositions and methods can also be used to treat disorders associated with pathological increases in levels of inflammatory cells, including, for example, asthma, eczema, sinusitis, atherosclerosis, rheumatoid arthritis, inflammatory bowel disease, cutaneous and systemic mastocytosis, psoriasis, and multiple sclerosis. Treatment with the provided polypeptide may be used to reduce itching, for example of healing wounds. Generally, itching results from histamine release by mast cells. In some embodiments, the provided compositions are used to reduce mast cell de-granulation and histamine release. In some embodiments, the provided compositions are used to treat conditions involving histamine release, including, but not limited to, itching, scratching, sinus irritation, allergic cough, red eyes, asthma, and eczema.

In some embodiments, an inflammatory response is related to chronic or acute immune disorders. In some embodiments, the composition provides method for the treatment of diseases or conditions related to chronic or acute immune disorders, or immunodeficiency such as primary immunodeficiency and secondary or acquired immunodeficiency, and/or auto-immune disorders. Examples of auto-immune disorders may include lupus, scleroderma, certain types of hemolytic anemia, vasculitis, Type I diabetes, Graves disease, rheumatoid arthritis, multiple sclerosis, Goodpasture's syndrome, pernicious anemia, some types of myopthay, and Lyme disease (Late). Exemplary of primary immunodeficiency includes severe combined immunodeficiency (SCID), DiGeorge syndrome, hyperimmunoglobulin E syndrome (also known as Job's Syndrome), common variable immunodeficiency (CVID), chronic granulomatous disease (CGD), Wiskott-Aldrich syndrome (WAS), autoimmune lymphoproliferative syndrome (ALPS), hyper IgM syndrome, Leukocyte adhesion deficiency (LAD), NF-κB Essential Modifier (NEMO) Mutations, selective immunoglobulin A deficiency, X-linked agammaglobulinemia (XLA, also known as Bruton type agammaglobulinemia), and X-linked lymphoproliferative disease (XLP) and Ataxia-telangiectasia. An example of secondary immune deficiency is AIDS. Other immune disorders include allergies such as seasonal allergy, mastocytosis, perennial allergy, anaphylaxis, food allergy, allergic rhinitis, and atopic dermatitis. Additional non-limiting examples include acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Ha e (OMS), optic neuritis, Ord's thyroiditis, oemphigus, polyarthritis, primary biliary cirrhosis, psoriasis, rheumatoid shimoto's disease, lupus erythematosus, multiple sclerosis, myasthenia gravis, opsoclonus myoclonus syndrom arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thromobsis.

In some embodiments of the disclosure, the administration of said composition reduces one or more symptoms associated with the autoimmune disease, neurodegenerative disease, or disease associated with inflammation. Non-limiting examples of such symptoms include inflammation, fatigue, dizziness, malaise, elevated fever and high body temperature, extreme sensitivity to cold in the hands and feet, weakness and stiffness in muscles and joints, weight changes, digestive or gastrointestinal problems, low or high blood pressure, irritability, anxiety, or depression, infertility or reduced sex drive (low libido), blood sugar changes, and depending on the type of autoimmune disease, an increase in the size of an organ or tissue, or the destruction of an organ or tissue.

In some embodiments, administering a composition comprising sinetirucallol is effective in ameliorating symptoms associated with rheumatoid arthritis including but not limited to a reduction in the swelling of joints, a reduction in serum anti-collagen levels, and/or a reduction in joint pathology such as bone resorption, cartilage damage, pannus, and/or inflammation. In some embodiments, the subject methods are effective in reducing joint (e.g. leg or ankle) inflammation by at least about 2%, 5%, 10%, 15%, 20%, 25%, 30%, 50%, 60%, or about 75% to 90%. In some embodiments, inflammation is reduced by at least about 2%, 5%, 10%, 15%, 20%, 25%, 30%, 50%, 60%, or about 75% to 90% or more. In some embodiments, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In some embodiments, the subject methods are effective in reducing ankle histopathology scores by about 5%, 10%, 15%, 20%, 25%, 30%, 40%, 50%, 60%, 75%, 80%, 90% or more. In some embodiments, the subject methods are effective in reducing knee histopathology scores by about 5%, 10%, 15%, 20%, 25%, 30%, 40%, 50%, 60%, 75%, 80%, 90% or more.

In some embodiments, administering a composition comprising sinetirucallol is effective for the treatment of asthma. Also, the compounds or pharmaceutical composition described herein may be used for the treatment of endotoxemia and sepsis. In one embodiment, the compounds or pharmaceutical composition described herein are used to for the treatment of rheumatoid arthritis (RA). In yet another embodiment, the compounds or pharmaceutical composition described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

A reduction in inflammation can be measured using a variety of methods, such as methods described herein. In some embodiments, a reduction in inflammatory response is an indicia of reduction in inflammation. Methods for measuring reduction in inflammatory response include, for example, a reduction in expression or activity of one or more biological markers selected from the group consisting of: iNOS, COX-2, TNF-alpha, PGE2, IL-6, IL-β, IL-33, NLRP3, pERK, NFκB, MMP2, and MMP9.

A reduction in inflammation can also be measured by a reduction in the density of inflammatory cell types such as, for example, monocytes or astrocytes. A reduction in inflammation can be measured by a reduction in the density of inflammatory cell types such as, for example, neutrophils, mast cells, basophils, and monocytes. A reduction in inflammation can be calculated by an in vivo measurement of neutrophil activity. In addition factors like frequency of mast cell degranulation or measurement of histamine levels or levels of reactive oxygen species can be used as measurements of reduction in inflammation. The level of inflammation can also be indirectly measured by checking for transcription levels of certain genes by qRT-PCR for e.g. genes like, Interferon-alpha, -beta and -gamma, Tumor Necrosis Factor-alpha, Interleukine 1beta, -2, -4, -5, -6, -8, -12, -18, -23, -27, CD4, CD28, CD80, CD86, MHCII, and iNOS. Measurement of pro-inflammatory cytokine levels in the tissues and or bodily fluids of the subject including plasma can measure a reduction in inflammation. It is noteworthy that a mechanism of ACT peptide action may be by inhibition of inflammatory cell migration and/or inhibition of pro-inflammatory chemicals (histamine, reactive oxygen species) and pro-inflammatory cytokines such as Interleukin (IL)-1, IL-6, IL-8 and tumor necrosis factor (TNF).

In some embodiments, a reduction in inflammatory response is also evidenced by a decrease in a level of one or more free radicals associated with an inflammatory response, such as reactive oxygen species or a reactive nitrogen species. Reactive oxygen species ("ROS") and reactive nitrogen species ("RNS") are two major types of compounds with important physiological functions in organisms. ROS and RNS include not only radicals, but other related non-radical species that are formed during intracellular oxidation processes. These free radicals and related species can also participate in the regulation of signal transduction from membrane receptors, immunological and inflammatory responses, smooth muscle relaxation, redox homeostasis, apoptosis, and vascular tone, among others.

ROS include radical species, such as superoxide radical anion ($O_2^-$.) and hydroxyl radical (.OH); and related non-radical species, such as peroxide (ROOR), hydrogen peroxide ($H_2O_2$), singlet oxygen ($^1O_2$), and peroxynitrite ($ONOO^-$). RNS include radical species, such as nitric oxide (.NO); and related non-radical species, such as nitrosonium cation ($NO^+$), nitroxyl anion ($NO^-$), and peroxynitrite ($ONOO^-$). Numerous enzymatic processes, such as the reactions catalyzed by xanthine oxidase, nicotinamide adenine dinucleotide phosphate (NADPH) oxidase isoforms and cyclooxygenase isoforms, lead to the formation of ROS (Fink M P. "Reactive oxygen species as mediators of organ dysfunction caused by sepsis, acute respiratory distress syndrome, or hemorrhagic shock: potential benefits of resuscitation with Ringer's ethyl pyruvate solution", Curr Opin Clin Nutr Metab Care 2002, 5:167-174). RNS are intermediates that can be formed as a result of oxidation of L-arginine. This oxidation process is catalyzed by nitric oxide synthase (NOS) isoforms and results in the formation of nitric oxide (.NO). There are three NOS isoforms: neuronal NOS (nNOS), endothelial NOS (eNOS), and inducible NOS (iNOS). These isoforms are expressed in various subcellular locations and tissues, where non-limiting examples include cardiac myocytes, glial cells, skeletal cells, neutrophils, vascular smooth muscle cells, and platelets. Nitric oxide can be converted into other nonradical RNS, such as nitrosonium cation ($NO^+$), nitroxyl anion ($NO^-$), and peroxynitrite ($ONOO^-$, a toxic compound formed from a reaction between nitric oxide and superoxide anion).

ROS and RNS could also play critical roles as mediators in a number of different intracellular signaling cascades, including inflammatory processes (Dröge W, "Free radicals in the physiological control of cell function", Physiol Rev., 82(1):47-95, 2002). In particular, ROS have been implicated in the regulation of signaling mediated by the pro-inflammatory transcription factors, NF-κB (Pantano et al., "Redox-sensitive kinases of the nuclear factor-kappaB signaling pathway". Antioxid Redox Signal., 8(9-10):1791-806, 2006; Gloire et al., "NF-kappaB activation by reactive oxygen species: fifteen years later", Biochem Pharmacol, 72:1493-1505, 2006) and activator protein (AP)-1 (Liu et al. 'Redox-dependent transcriptional regulation". Circ Res 97:967-974, 2005; Lin et al., "Superoxide dismutase inhibits the expression of vascular cell adhesion molecule-1 and intracellular cell adhesion molecule-1 induced by tumor necrosis factor-alpha in human endothelial cells through the JNK/p38 pathways", Arterioscler Thromb Vasc Biol, 25:334-340, 2005). Redox-dependent signaling mechanisms also have been implicated in the activation of pro-inflammatory mitogen-activated protein kinases (MAPK), including p38 and JNK (Nagai et al., "Pathophysiological roles of ASK1-MAP kinase signaling pathways", J Biochem Mol Biol, 40:1-6, 2007). Expression of nitric oxide synthase isoforms have been associated with inflammation, where induction of inducible nitric oxide synthase (iNOS) can be initiated by liposaccharide (LPS), endotoxin, or inflammatory cytokines, such as IFN-γ, TNF-αc, and IL-1 (Guzik et al., "Nitric oxide and superoxide in inflammation and immune regulation," J Physiol Pharmacol, 54(4):469-87, 2003).

Proper regulation of ROS and RNS provides protection against oxidative stress and provides important mediators in cellular processes. However, excessive production or improper clearance of ROS and RNS can result in damage to cellular constituents, such as proteins, DNA, and membrane lipids; dysfunction of intracellular signaling cascades; cytotoxicity; and enzyme inactivation. Free radicals have been implicated as being important in the pathogenesis in a wide range of diseases and pathological processes, including various forms of cancer, type 2 diabetes mellitus, atherosclerosis, chronic inflammatory conditions, ischemia/reperfusion injury, sepsis and some neurodegenerative diseases (Dröge W. Free radicals in the physiological control of cell function. Physiol Rev 2002, 82:47-95).

In some embodiments, administering a composition in accordance with the present disclosure is effective in reducing the level of one or more free radicals by at least about 0.1%, 2%, 5%, 10%, 15%, 20%, 25%, 30%, 50%, 60%, or about 75% to 90% or more. A reduction in the level of one or more free radicals can be measured by any suitable assay, such as by nitrite quantification. A reduction in the level of one or more free radicals may also be measured in an assay for anti-oxidant activity, such as an assay disclosed herein.

Inflammatory response may also result in tissue swelling. As described herein, swelling is typically a reaction of the body to an injury as a result of the increased movement of fluid and white blood cells into the area of inflammation. In general, swelling is any abnormal enlargement of a body part. This can be due to fluid—including blood—bony malformation, muscle, or any number of things. In some cases, swelling can be edema, which describes fluid, or swelling, that has accumulated in the tissue outside of the joint capsule including, swelling in the calf or thigh. In some cases, swelling can be effusion, which describes fluid that is inside the joint capsule, such as a swollen ankle or knee. In some cases, swelling can be hemarthrosis, which is a condition where there is blood in the effusion within the joint capsule and indicates either a ligamentous injury, such as an ACL tear, or a fracture. This is typically determined by extracting some fluid from the joint capsule with a needle. Hemarthrosis can be acute or chronic. Acute hemarthrosis refers to swelling that occurs within 24 hours of injury. If the swelling occurs within the first 2 hours, it is probably associated with hemarthrosis, and should be checked out by a medical profession. Chronic hemarthrosis refers to swelling that occurs over a long period of time, and can be difficult to detect, but is very detrimental if left untreated.

In some embodiments, the reduction of inflammatory response is evidenced by a reduction in tissue swelling. As described herein, a reduction of swelling can be found in tissues including skin, epithelia, synovial tissue, tendons, cartilage, ligaments, bone, muscle, organs, dura, blood vessels, bone marrow, and extracellular matrix. The reduction of tissue swelling can be determined by the change of swelling index. As a non-limiting example, the swelling index can be calculated by dividing the area of the injured limb of an animal by the area of the control uninjured limb of an animal. The swelling index can be presented as a ratio based on the swelling index of the injured and control uninjured limb. In some embodiments, the swelling index of the injured and control uninjured limb prior to and after said administration may be recorded for comparison. As another non-limiting example, inflammation in animal models can be induced by injecting Complete Freund's Adjuvant (CFA) in one paw. In some embodiments, administering the composition is effective in reducing tissue swelling by at least about 0.1%, 2%, 5%, 10%, 15%, 20%, 25%, 30%, 50%, 60%, or about 75% to 90% or more.

In one aspect, the present disclosure provides pharmaceutical compositions and methods for promoting wound healing comprising administering to a subject in need thereof a dosage form comprising sinetirucallol. The composition can be any sinetirucallol-containing composition described herein. In one embodiment, the dosage form of sinetirucallol is formulated for administration to be a subject. In a related embodiment, the dosage form is a pharmaceutical composition comprising a pharmaceutically acceptable carrier, examples of which are described herein. In a still related embodiment, the dosage form comprises a *Spiranthes sinensis* extract, such as an extract described herein. In some embodiments, promoting wound healing comprises increasing the rate of wound healing compared to a rate at which a comparable untreated wound heals, or compared to a rate at which the treated wound was healing prior to treatment. An improved rate of wound healing can include a 10%, 20%, 30%, 40%, 50%, 100%, 150%, 200%, 250%, 500%, 1000%, or higher increase in healing rate.

In some embodiments, promoting wound healing comprises reducing fibrosis as compared to fibrosis that occurs in a comparable untreated wound, or fibrosis found in a partially healed portion of a healing wound prior to treatment. Fibrosis is a pathologic process, which includes scar formation and over production of extracellular matrix, by the connective tissue, as a response to tissue damage. The repair process typically involves two distinct phases: a regenerative phase, in which injured cells are replaced by cells of the same type, leaving no lasting evidence of damage; and a phase know as fibroplasia or fibrosis, in which connective tissues replaces normal parenchymal tissue. Although initially beneficial, the repair process becomes pathogenic when it is not controlled appropriately, resulting in substantial deposition of extracellular matrix component in which normal tissue is replaced with permanent scar tissue. In some embodiments, administering a composition of the disclosure reduces fibrosis by about or more than about 10%, 20%, 30%, 40%, 50%, 100%, 150%, 200%, 250%, 500%, 1000%, or more.

In some embodiments, methods provided herein can reduce scar tissue formation in a subject following tissue injury. Scar tissue may replace injured skin and underlying muscle, damaged heart muscle, or diseased areas of internal organs such as the liver. Dense and thick, it is usually paler than the surrounding tissue because it is poorly supplied with blood, and although it structurally replaces destroyed tissue, it typically cannot perform all functions of the missing tissue. It is typically composed of collagenous fibers, which will often restrict normal elasticity in the tissue involved. Scar tissue may therefore limit the range of muscle movement or prevent proper circulation of fluids when affecting the lymphatic or circulatory system. Glial scar tissue following injury to the brain or spinal cord is one of the main obstacles to restoration of neural function following damage to the central nervous system. A reduction in scar tissue can be assessed by the population of cell types within the injured site. For example, a reduction in glial scar tissue can be estimated by an increased ratio of neuronal to astrocytic cells. A reduction in scar tissue formation can be measured by a simple measurement of scar width or area of scar tissue (Wilgus et al., "Reduction of scar formation in full-thickness wounds with topical celecoxib treatment." Wound Rep Reg 11:25-34, 2003). In addition histological assessments can be made about the restoration of structural complexity within healed tissue in comparison to normal tissue. In some embodiments, scar formation can be reduced by at least about 0.1%, 2%, 5%, 10%, 15%, 20%, 25%, 30%, 50%, 60%, or about 75% to 90% or more.

A reduction in fibrotic tissue formation in a subject can be measured by clinical judgment of a doctor assessing whether a regain in normal structure and function of a given tissue and/or organ in a subject has resulted following a treatment. As an example, for psoriasis a medical profession would assess the subject's skin to determine whether there has been a reduction in patches of raised red skin covered by flaky white buildup. Certain kinds of psoriasis, are characterized by a pimple-ish (pustular psoriasis) or burned (erythrodermic) appearance. In such cases, the medical profession would determine whether treatment has resulted in the reduction of these symptoms. In the case of an tissue or organ in which a subject where a medical profession judges that a biopsy is clinically available and/or necessary or in an animal model of the human disease, tissue fragments of bioposies would be prepared and tissue histological structure would be assessed by a clinical pathologist and/or trained histopathologist to determine if reduction in fibrosis and restoration of normal tissue structure and function has occurred. The area of fibrosis to normal tissue could also be quantitatively assessed on such histological preparations.

Providing wound healing may comprise treating a subject undergoing cosmetic surgery or having a tissue injury. In other embodiments, the present disclosure provides methods for treating injuries, and/or promoting regeneration of tissues using the subject compositions. Examples of tissue injury include a scrape, cut, laceration wound, crush wound, compression wound, stretch injury, bite wound, graze, bullet wound, explosion injury, bed sore, body piercing, stab wound, burn wound, gunshot wound, wind burn, sun burn, chemical burn, surgical wound, surgical intervention, medical intervention, host rejection following cell, tissue or organ grafting, pharmaceutical effect, pharmaceutical side-effect, bed sore, radiation injury, cosmetic skin wound, internal organ injury, disease process (e.g., asthma, cancer), infection, infectious agent, developmental process, maturational process (e.g., acne), genetic abnormality, developmental abnormality, environmental toxin, allergen, scalp injury, facial injury, jaw injury, foot injury, toe injury, finger injury, bone injury, sex organ injury, joint injury, excretory organ injury, eye injury, corneal injury, muscle injury, adipose tissue injury, lung injury, airway injury, hernia, anus injury, piles, ear injury, retinal injury, skin injury, abdominal injury, arm injury, leg injury, athletic injury, back injury, birth injury, premature birth injury, toxic bite, sting, tendon injury, ligament injury, heart injury, heart valve injury, vascular system injury, cartilage injury, lymphatic system injury, craniocerebral trauma, dislocation, esophageal perforation, fistula, nail injury, foreign body, fracture, frostbite, hand injury, heat stress disorder, laceration, neck injury, self mutilation, shock, traumatic soft tissue injury, spinal cord injury, spinal injury, sprain, strain, tendon injury, ligament injury, cartilage injury, thoracic injury, tooth injury, trauma, nervous system injury, aging, aneurism, stroke, digestive tract injury, infarct, ischemic injury, fracture, sprain, strain, stroke, infarction, aneurism, herniation, ischemia, fistula, dislocation, radiation, cell, tissue or organ grafting, or cancer. In some embodiments, the compounds described herein are used to treat and/or prevent acne.

In some embodiments, promoting wound healing comprises restoring an amount of normal tissue mechanical properties to a wounded tissue, such as tensile strength following tissue injury in a subject. "Tensile strength" refers to the amount of stress or strain required to break the tissue or wound. The tensile strength of treated wounds can be 60, 65, 70, 75, 80, 85, 90, 95, 100% that of uninjured tissue within 1 month, 2 months, 3 months, 4 months, 5 months or 6 months after treatment. In some embodiments, provided is a method of restoring tissue mechanical properties, including increasing tensile strength of a healed injury to approach or reach that of normal uninjured tissue, in a subject comprising administering to the subject one or more of the herein provided compositions (e.g. sinetirucallol or *Spiranthes sinensis* extract) in a pharmaceutically acceptable carrier.

Examples of tissues that may be treated to restore tensile strength using a disclosed composition or method include injuries to musculoskeletal structures/tissues, and the skin covering these structures. For example, the provided compositions may be administered to improve tensile strength of articulating joints, bone, cartilage, tendons, or ligaments. Improving tensile strength can include improving tensile strength of skin under higher degrees of stress/strain, such as the skin covering the elbow, knee, or foot. The most common problems associated with healing of joint injuries is that excessive scarring in these areas leads to contraction, and non-extensibility of the healed joint area. This has serious cosmetic and psychological consequences. The properties of the composition can be used to modulate and lessen the formation of such scar tissue leading to greater mobility of the joint.

In some embodiments, promoting wound healing comprising increasing tissue regeneration following tissue injury in a subject. In contrast to scarring, tissue regeneration involves the restoration of the tissue to its original structural, functional, and physiological condition. This is also referred to herein as tissue "complexity". The restoration can be partial or complete, meaning 10, 20, 30, 40, 50, 60, 70, 80, 90, 100% restoration, or any amount of restoration in between as compared to native or control levels. As an example, in the case of a skin injury, tissue regeneration can involve the restoration of hair follicles, glandular structures, blood vessels, muscle, or fat. In the case of a brain injury, tissue regeneration can involve maintenance or restoration of neurons. As an example in the case of skin an improvement in tissue regeneration can be assessed by measurements of the volume of fibrous scar tissue to normal regenerated skin as a ratio. As another example, counts can be made of discrete regenerating structures such as regenerating skin glands normalized to the volume of the wound area.

In one embodiment, tissue regeneration involves the recruitment and differentiation of stem cells to replace the damaged cells. The primary roles of stem cells in a living organism are to maintain and repair the tissue in which they are found. By stem cell differentiation is meant the process whereby an unspecialized cell (e.g., stem cell) acquires the features of a specialized cell such as a skin, neural, heart, liver, or muscle cell. As an example, in the case of a skin injury, tissue regeneration can involve the differentiation of stem cells present in the epithelium into hair follicles (Alonso and Fuchs, 2003). In the case of a brain injury, tissue regeneration can involve the differentiation of stem cells into neurons. The provided method can enhance stem cell differentiation following tissue injury in a subject. Enhanced stem cell differentiation can be measured by providing a clinically acceptable genetic or other means of marking endogenous or engrafted stem cells and determining the frequency of differentiation and incorporation of marked stem cells into normal tissue structures. As another example, certain structures such as hair follicles are known to be regenerated from endogenous stem cells following tissue injury. As such, counts of hair follicles normalized to tissue injury area would serve as a quantitative assessment of enhanced stem cell differentiation.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Purification of Sinetirucallol

Methods

The air-dried whole plants of *Spiranthes sinensis* (PERS.) AMES were purchased from a local herbal medicine store, Hualien, Taiwan, in November, 2013, and identified by comparison with the voucher specimens already deposited at the Herbarium of the Department of Botany, National Taiwan University, Taipei, Taiwan (no: TAI. 218182, collected on Apr. 12, 1934).

The air-dried whole plants of *Spiranthes sinensis* (e.g. 2.4 kg) were powdered and directly extracted with EtOAc (e.g. 50 L) three times at room temperature for 72 h each time, and the combined extracts were concentrated under reduced pressure. The crude extract (e.g. 160 g) was subjected to column chromatography over silica gel using gradient mixtures of n-hexane-EtOAc-methanol (1:0:0, 10:1:0, 5:1:0, 3:1:0, 1:1:0, 0:1:0, 0:40:1, 0:30:1, 0:20:1 and 0:10:1, respectively) as eluents. According to TLC results, thirteen fractions were obtained. The fourth fraction was further chromatographed on silica gel column using n-hexane-EtOAc (3:1) as eluent to yield ten fractions. Fraction 4-4 & 5 found crystals appeared after filtration and purified by recrystallization to obtain sinetirucallol. The identity of the compound was fully characterized by comparing their spectral data (IR, NMR and mass) with information reported in the literature.

For the following experiments, a stock composition was made by dissolving said extract in DMSO at a concentration of 1 mg/mL based on the total volume of said DMSO.

Example 2: Cell Toxicity of *Spiranthes sinensis* and Sinetirucallol

Methods
Cell Culture

The RAW264.7 murine macrophage cell line was purchased from the Bioresource Collection and Research Center (BCRC, Taiwan). The cells were incubated at 37° C. in 5% $CO_2$ in Dulbecco's modified Eagle's medium (DMEM; Gibco Inc., NY, USA) supplemented with 100 U/mL penicillin, 100 µg/mL sodium pyruvate and 10% fetal bovine serum (FBS; Gibco Inc.).

The cells were also treated with 0.01% DMSO as a vehicle control. The cells were seeded into 12-well plates at a density of $6\times10^5$ cells/well in 24 h then incubated with 0.1% BSA with serum-free medium 3 h, treated with different concentrations of *Spiranthes sinensis* extract or SI then incubated in the presence of LPS (1 µg/mL) for 4 h.
Cell Viability In order to examine the bio-compatibility of the extract of the present disclosed composition, a MTT assay (3-(4,5-dimethylthiazol-2-yl)-2,5-diphenyltetrazolium bromide (MTT, Invitrogen), a colorimetric based assay) was performed.

Briefly, $8\times10^3$ of cells per well were seeded in 96-well plates and were incubated in 5% $CO_2$ at 37° C. for overnight. Cells were treated different concentrations (5, 20, 50, and 100 µg/mL) of *Spiranthes sinensis* extract for 24 h, after incubation 20 µL (5 mg/mL) of MTT solution was added per well and further incubated for 4 h. The media was removed, and formazan was solubilized by adding 100 µl/well of DMSO (Sigma-Aldrich) and OD was measured at 570 nm using a microplate reader (ELISA reader, Thermo Labsystems). Percentage of viable cells was estimated by comparing with untreated control cells. The average absorbance value of the control cells was taken as 100% viability.

Data are expressed as means±S.E. Statistical comparisons of the results were made using one-way analysis of variance (ANOVA). Means within each column followed by the different letters are significantly different at p<0.05 by Turkey's test.

Results

Figure 1B:
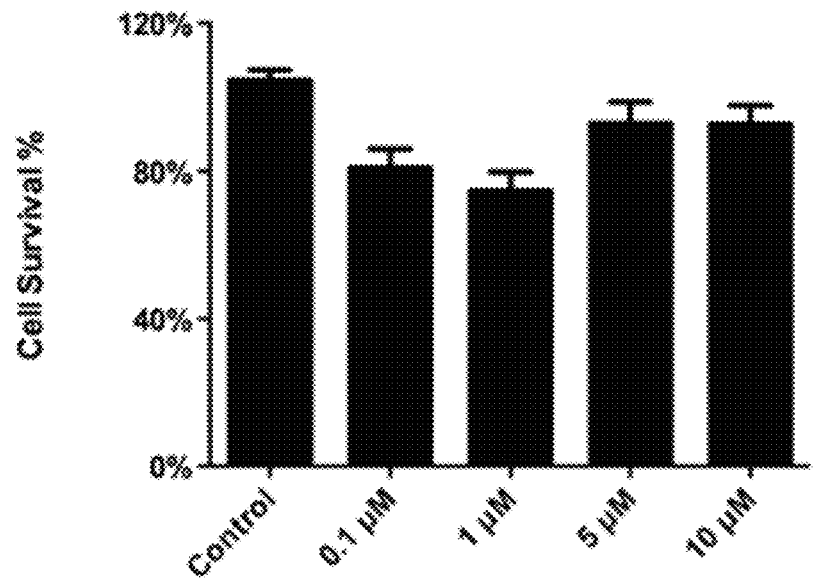

The cytotoxicity of *Spiranthes sinensis* extract and sinetirucallol in RAW 264.7 cells as analyzed by MTT assay. Cell viability was not affected with treatment *Spiranthes sinensis* extract (5, 20, 50, and 100 μg/mL) and sinetirucallol (0.1, 1, 5, and 10 μM) for 24 h (FIG. 1). These observations suggested that *Spiranthes sinensis* and sinetirucallol were not toxic to cells.

Example 3: Effect of *Spiranthes sinensis* Extract and Sinetirucallol on CFA-Induced Inflammation in Mice Methods
Animal C57BL/6 mice were obtained from the National Laboratory Animal Center (Taipei, Taiwan) and kept at controlled environmental conditions with room temperature (22±2° C.) and humidity (60±10%). The 12 h light (0600 am-1800 pm) and dark cycle was maintained throughout the study. Animal experiments were approved by the National Dong-Hwa University Animal Ethics Committee and were used according to the "Guide for the Care and Use of Laboratory Animals" of National Dong-Hwa University. All the animals which received CFA, developed severe inflammation, typically hind limb became severely red and edematous within 20 min period such that inflammatory score was 200% swelling. The experiment contained: CFA group: this group only induced by CFA but without treatment; *Spiranthes sinensis* extract (SS) group: this group received intraperitoneal injection of different concentrations (0.5, 0.3, and 0.06 mg/kg b.w) of *Spiranthes sinensis* extract; sinetirucallol (SI) group: this group received intraperitoneal injection of different concentrations (4.4, 2.2, and 0.44 μg/kg) of SI; Triamcinolone (TS): this group received intraperitoneal injection of 0.3 mg/kg of triamcinolone (a clinical steroid medicine) as a positive control; Sevatrim (SE): this group received intraperitoneal injection of 3 mg/kg of Sevatrim (a clinical NSAID) as a positive control. Five mice were in each group. To produce a chronic inflammatory response, mice were injected with 20 μL of Complete Freund's Adjuvant (CFA; *Mycobacterium tuberculosis*; Sigma, St. Louis, Mo., USA) subcutaneously in the plantar surface of the right hind paw (i.pl.). The left hind paw was used as a control.

After induced CFA (Day 0), mice were treated with SS extract and SI by intraperitoneal injection for 3 times until to Day 2. Anti-inflammatory effect was examined for 4 days and the swelling index was recorded every day. The swelling index was calculated by the following formula below and presented as a ratio based on the swelling index before injection (Day 0).

$$\frac{\text{Length} \times \text{Width of right hindpaw (injected paw)}}{\text{Length} \times \text{Width of left hindpaw (uninjected paw)}}$$

Data are expressed as means±S.E. Statistical comparisons of the results were made using one-way analysis of variance (ANOVA). Means within each column followed by the different letters were significantly different at p<0.05 by Turkey's test.

Results

Figure 2A:
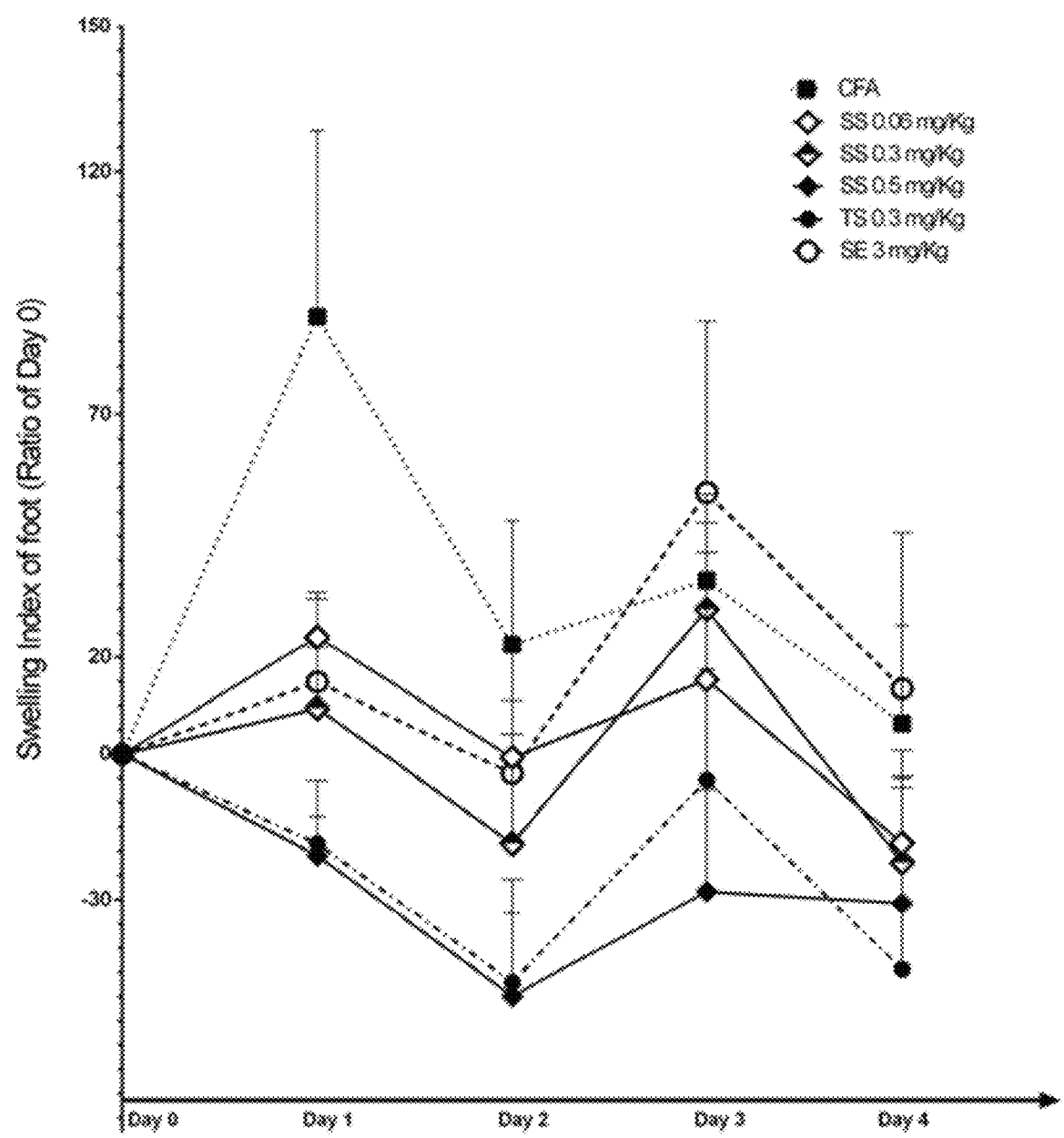
FIGS. 2A-2C show the inhibition of *Spiranthes sinensis* extract treatment on CFA-induced inflammation in mice.
Figure 2B:
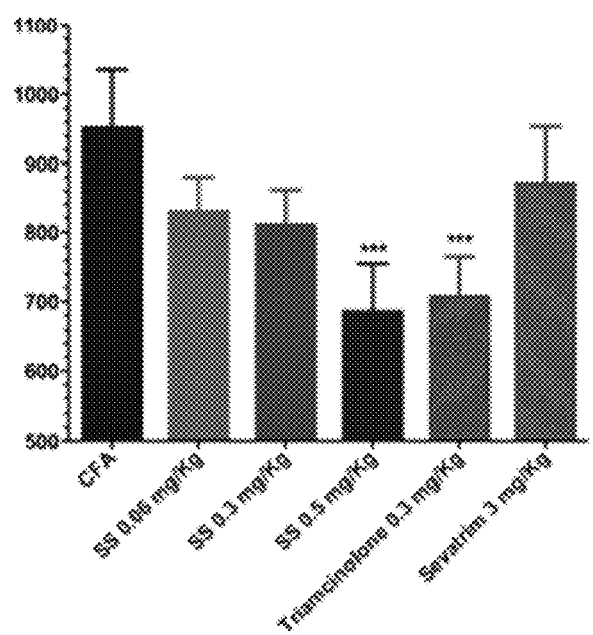
Figure 2C:
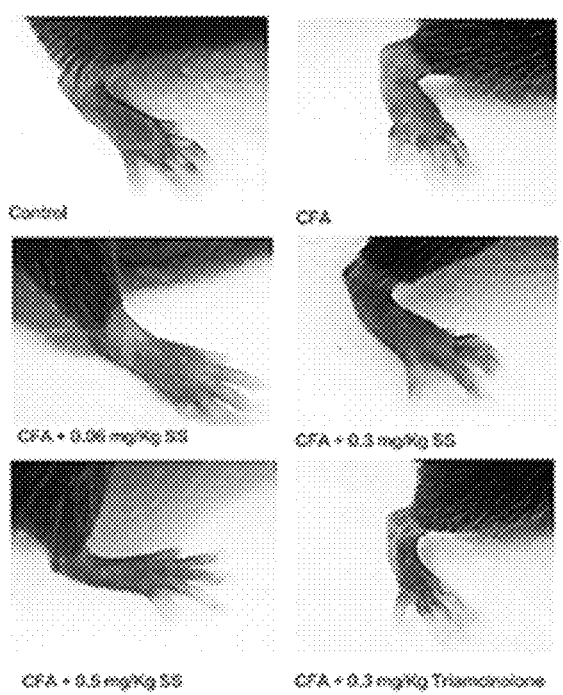
Figure 3A:
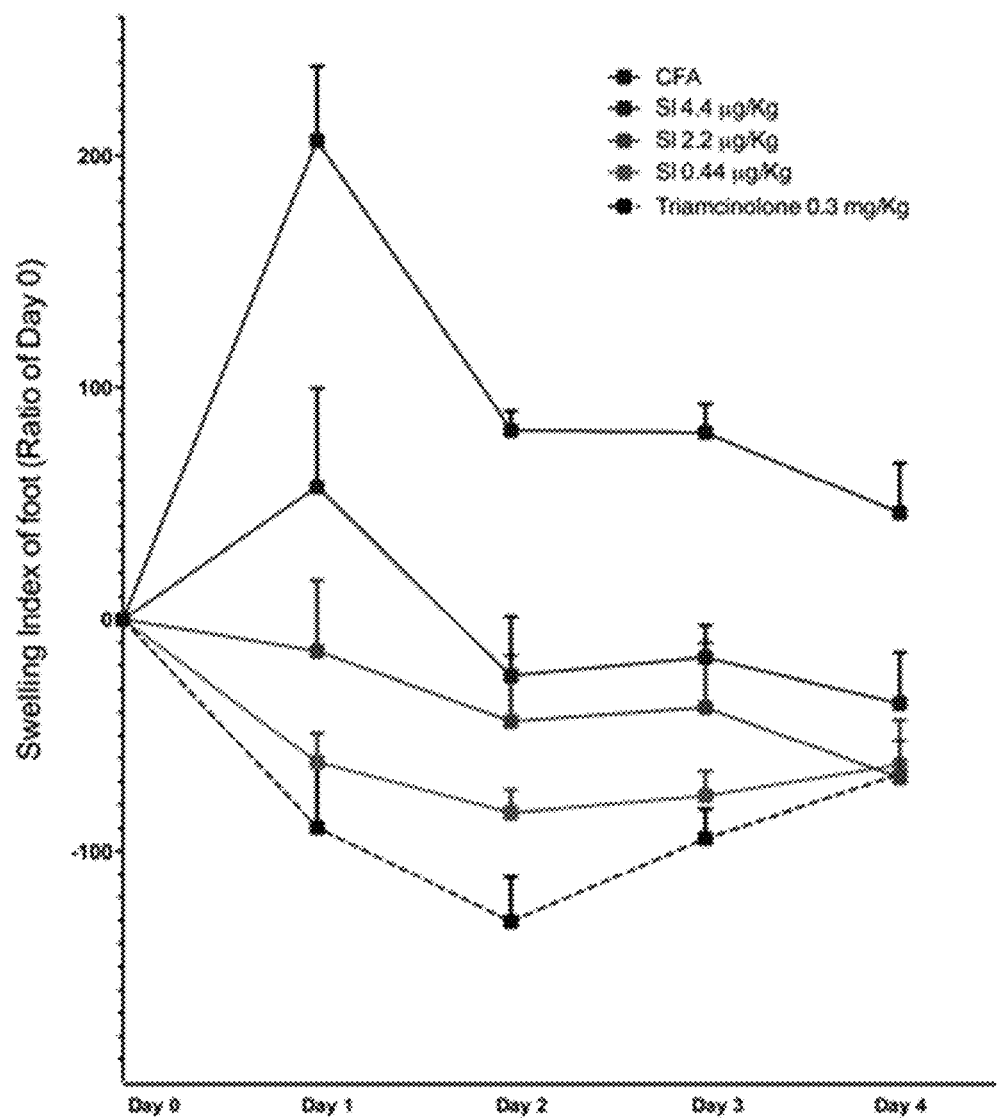
FIGS. 3A-3C show the inhibition of SI treatment on CFA-induced inflammation in mice.
Figure 3B:
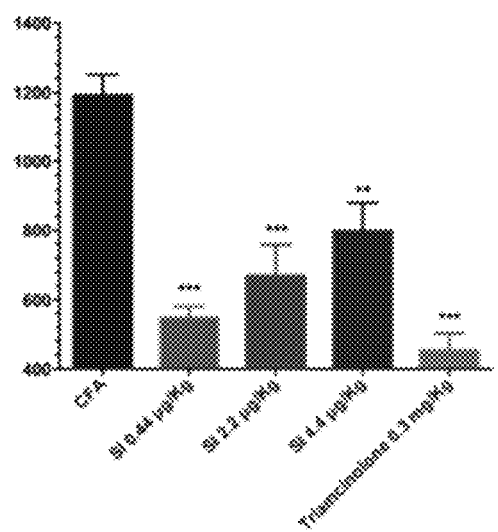
Figure 3C:
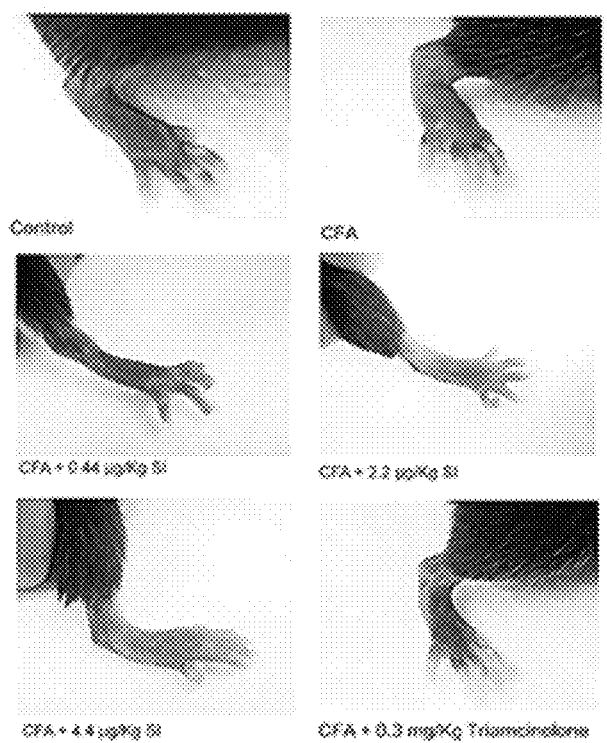

To evaluate the anti-inflammation of *Spiranthes sinensis* extract and SI, CFA-induced inflammation mice were performed to determine this effect. All treatment groups had anti-inflammatory effects when compared with CFA group. The higher concentration of *Spiranthes sinensis* extract had better anti-inflammatory effect among treatments. *Spiranthes sinensis* extract and positive control groups had significant recovery of swelling at Day 3 after stopping treatment especially steroid groups (FIG. 2). But the highest concentration at 0.5 mg/kg of *Spiranthes sinensis* extract had less foot swelling recovery than that of 0.3 mg/kg triamcinolone. SI group had anti-inflammatory effect much better than that of *Spiranthes sinensis* extract. And it had less foot swelling recovery than that of 0.3 mg/kg triamcinolone. But 0.44 μg/kg of SI was better effect than that of 4.4 μg/kg SI, indicating that high concentration of SI may cause excessively suppressed immune factors (FIG. 3).

Example 4: Effect of *Sipranthes sinensis* Extract on Blood MMP2 and MMP9 of CFA-Induced Inflammation in Mice Methods
Animal C57BL/6 mice were obtained from the National Laboratory Animal Center (Taipei, Taiwan) and kept at controlled environmental conditions with room temperature (22±2° C.) and humidity (60±10%). The 12 h light (0600 am-1800 pm) and dark cycle was maintained throughout the study. Animal experiments were approved by the National Dong-Hwa University Animal Ethics Committee and were used according to the "Guide for the Care and Use of Laboratory Animals" of National Dong-Hwa University. All the animals which received CFA, developed severe inflammation, typically hind limb became severely red and edematous within 20 min period such that inflammation score was 200% swelling. The experiment contained: CFA group: this group only induced by CFA but without treatment; *Spiranthes sinensis* extract (SS) group: this group intraperitoneal injection the difference concentration (0.5, 0.3, and 0.06 mg/kg b.w) of *Spiranthes sinensis* extract; sinetirucallol (SI) group: this group intraperitoneal injection the difference concentration (4.4, 2.2, and 0.44 μg/kg) of SI; Triamcinolone: this group intraperitoneal injection 0.3 mg/kg of triamcinolone of clinical steroid medicine for positive control; Sevatrim: this group intraperitoneal injection 3 mg/kg of Sevatrim of clinical NSAIDs for positive control. Five mice were in each group.

Gelatin Zymography

The activities of MMP2 and MMP9 were assayed by gelatin zymography because this method is capable to detect the active form and latent form of MMP2 and MMP9 based on their molecular weight. The blood was collected from CFA-induced mice at Day 4 and centrifuged to obtain serum. The serum was collected and quantified using Bradford dye (Bio-Rad). 8% SDS-PAGE gels were prepared containing 10% gelatin. 7.5 μg of protein sample was loaded into gel and electrophoresis separation was performed at 80V for 2-3 h. Incubated in developing buffer at 37° C. for 16 h. Finally, gel was stained in 0.1% Coomassie blue R-250 (Bio-Rad) for 4 h and then destained by fixing buffer. Gels were scanned using Epson scanner and quantified using multi-gauge software (Fujifilm).

Samples from mice in the SS group were processed similarly. Blood samples were collected from the tail vein at Day 4. The blood was pre-heated at 55° C. with 2× loaded dye (0.125 M Tris-HCl, pH 6.8, 4% SDS, 0.04% Bromophenol blue, 20% Glycerol). 8% SDS-PAGE gels were prepared containing 10%/gelatin. 5 μL of blood sample was loaded into the gel and electrophoresis separation was performed at 80V for 2-3 h. After electrophoresis, gel was washed 2 times in 50 mL of 2.5% Triton X-100 per gel, and then incubated in developing buffer (0.05 M Tris-HCl, pH 8.8, 5 mM $CaCl_2$), 0.02% $NaN_3$) at 37° C. for 16 h. Finally, the gel was stained in 0.1% Coomassie blue R-250 (Bio-Rad) for 4 h and then destained by fixing buffer (45% methanol, 10%/acetic acid). Gels were scanned using an Epson scanner and quantified using multi-gauge software (Fujifilm). This method is capable of detecting the active form and latent form of MMP9 at their correct molecular weight size.

Data was expressed as means±SEM. Statistical comparisons of the results were made using one-way analysis of variance (ANOVA). Means within each column followed by the different letters were significantly different at $p<0.05$ by Turkey's test.

Results

Figure 4A:
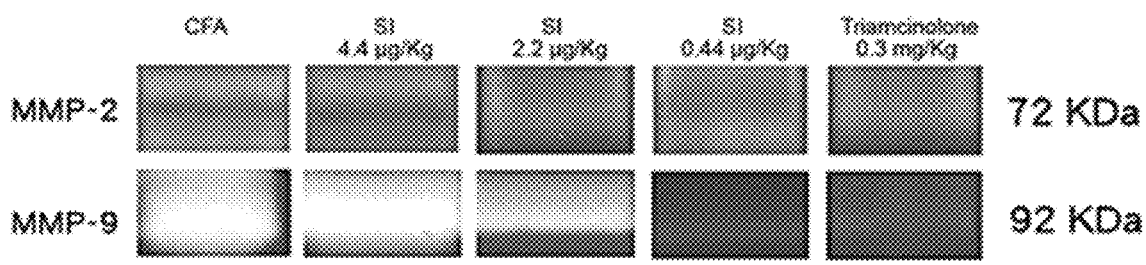
FIGS. 4A-4B show the suppression of serum MMP2 and MMP9 after SI treatment in CFA-induced inflammation mice.
Figure 4B:
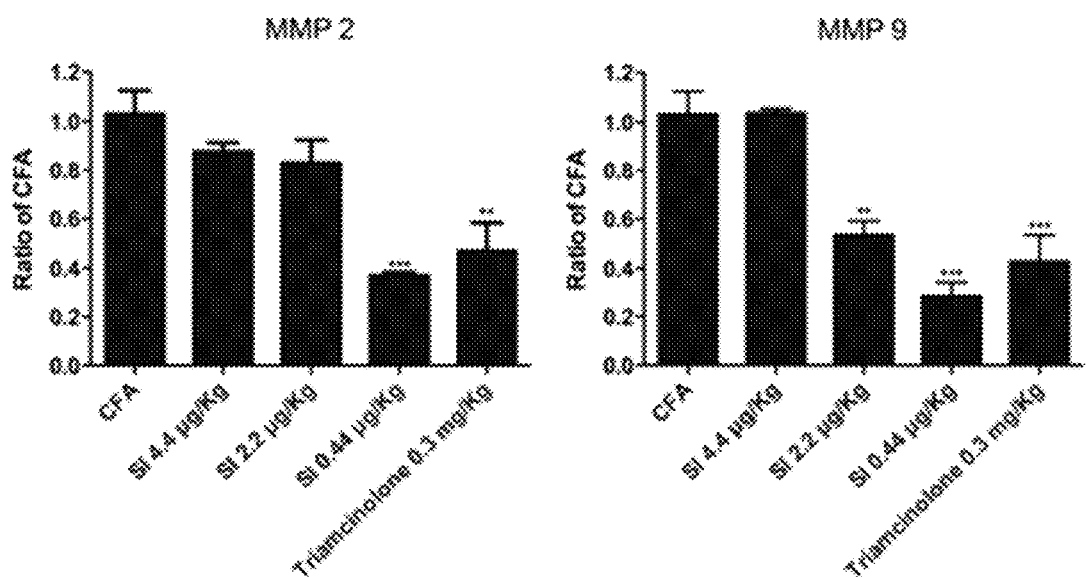
Figure 5A:
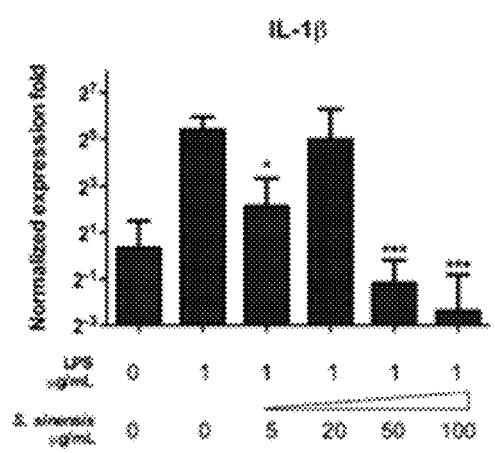
FIGS. 5A-5F show treatment with *Spiranthes sinensis* extract reduced cytokine and inflammation factor mRNA expression in LPS-induced RAW 264.7 cells. Different concentrations (5, 20, 50, and 100 μg/mL) of *Spiranthes sinensis* extract were employed to treat in LPS-induced RAW 264.7 cells for 6 h. The amounts mRNA of cytokines (FIG. 5A) IL-1β, (FIG. 5B) IL-6, (FIG. 5C) TNF-α, (FIG. 5D) iNOs, (FIG. 5E) NLRP3, and (FIG. 5F) IL-33 of RAW 264.7 cells. The mRNA levels were measured by Q-PCR. The values represent the means±S.E. of three independent experiments. *$P<0.05$; $P<0.01$; *$P<0.001$ as compared with the only 1 μg/mL of LPS treated group.
Figure 5B:
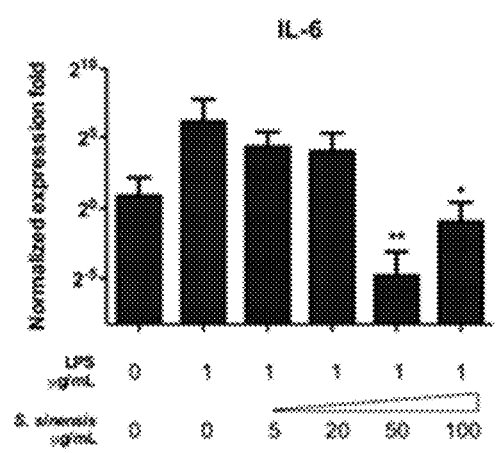
Figure 5C:
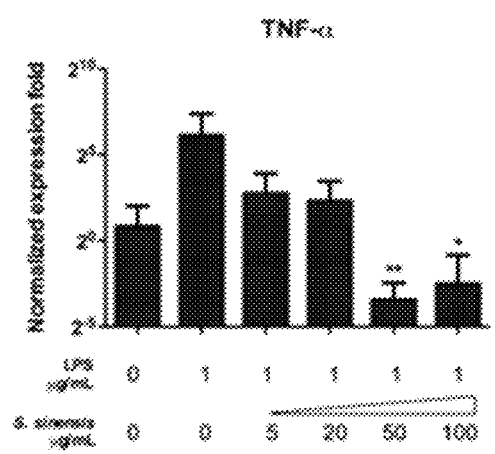
Figure 5D:
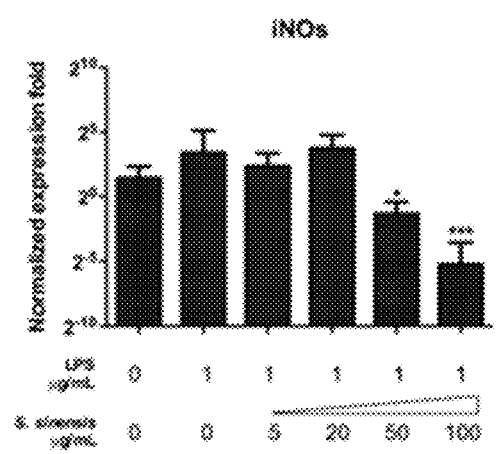
Figure 5E:
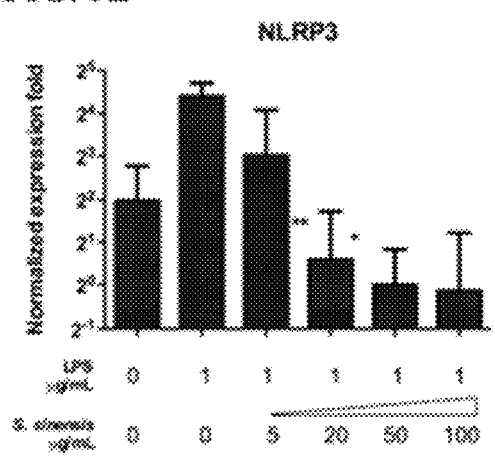
Figure 5F:
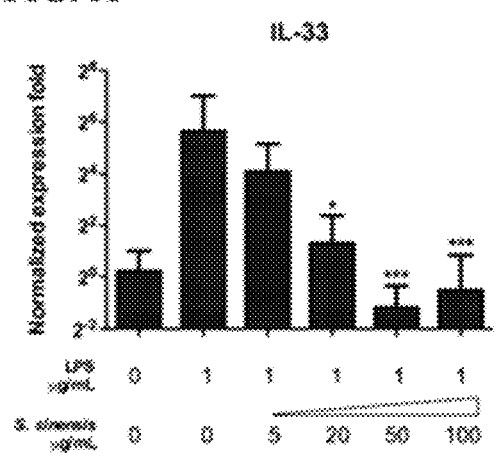
Figure 6A:
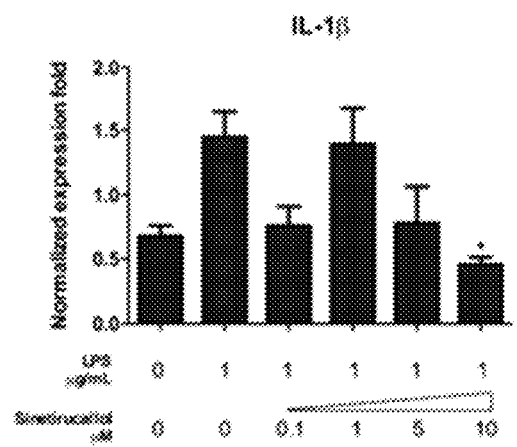
FIGS. 6A-6F show SI treatment reduced cytokine and inflammation factor mRNA expression in LPS-induced RAW 264.7 cells. Difference concentrations (0.1, 1, 5, and 10 μM) of SI were employed to treat in LPS-induced RAW 264.7 cells for 6 h. The amounts mRNA of cytokines (FIG. 6A) IL-1β, (FIG. 6B) IL-6, (FIG. 6C) TNF-α, (FIG. 6D) iNOS, (FIG. 6E) NLRP3, and (FIG. 6F) IL-33 of RAW 264.7 cells. The mRNA levels were measured by Q-PCR. The values represent the means±S.E. of three independent experiments. *$P<0.05$; $P<0.01$; *$P<0.001$ as compared with the only 1 μg/mL of LPS treated group.
Figure 6B:
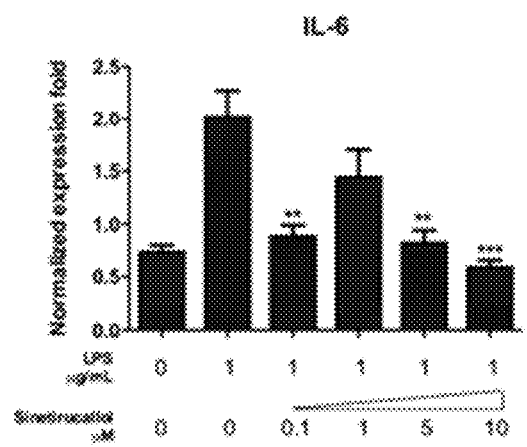
Figure 6C:
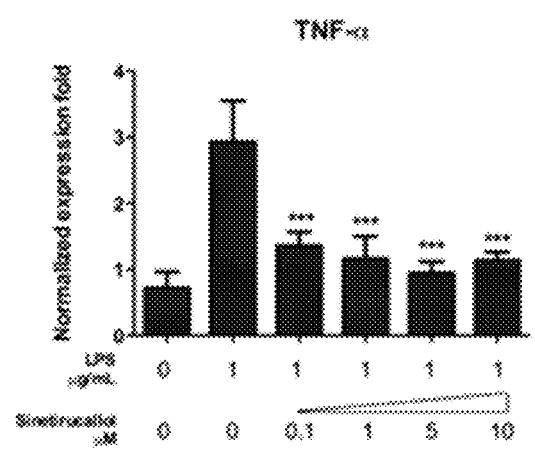
Figure 6D:
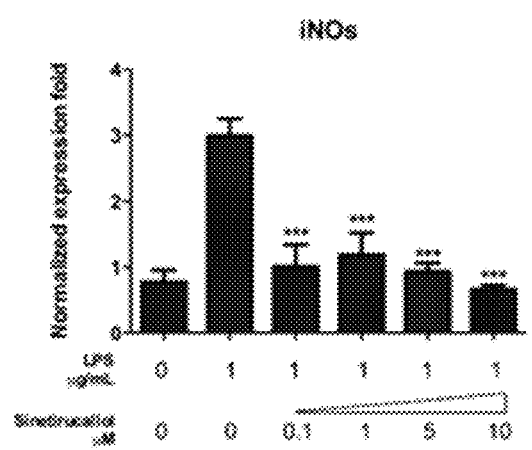
Figure 6E:
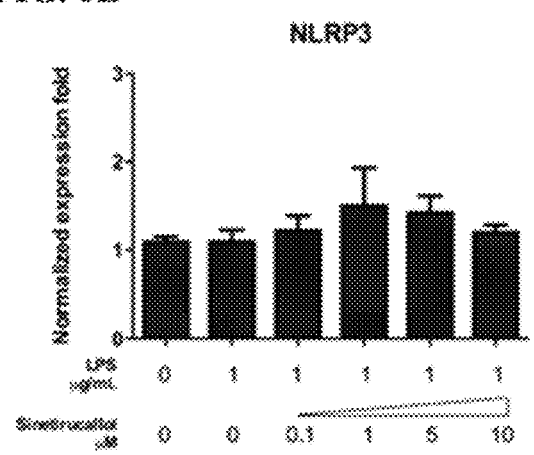
Figure 6F:
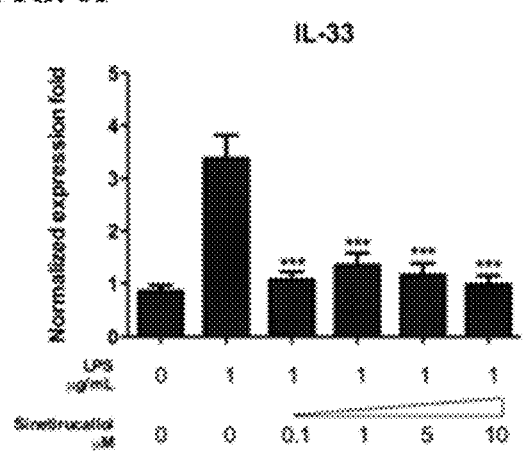
Figure 7A:
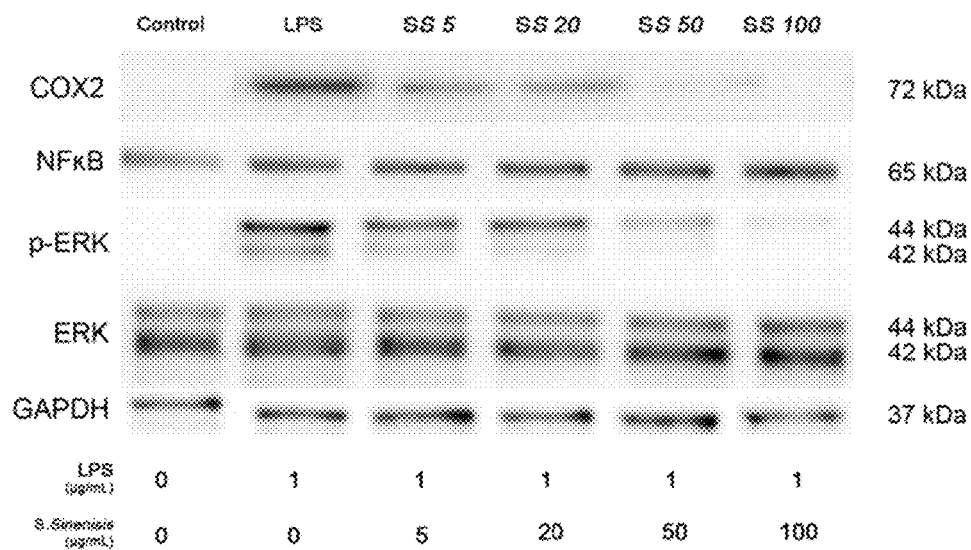
FIGS. 7A-7D illustrate *Spiranthes sinensis* extract inhibited expressions of COX-2, NFκB, p-ERK, and ERK of LPS-induced RAW264.7 cells. Treatment difference concentration (5, 20, 50, and 100 μg/mL) of *Spiranthes sinensis* extract were employed to treat in LPS-induced RAW 264.7 cells for 12 h. Cell were lysed in RIPA buffer for Western blot.
Figure 7B:
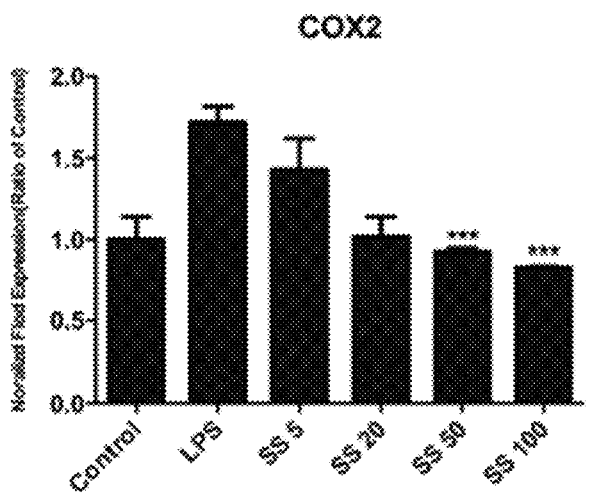
Figure 7C:
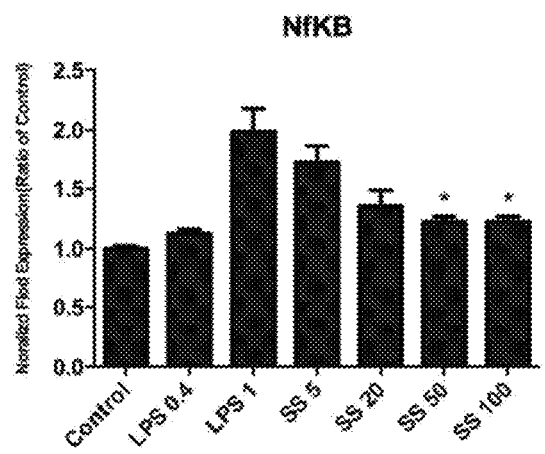
Figure 7D:
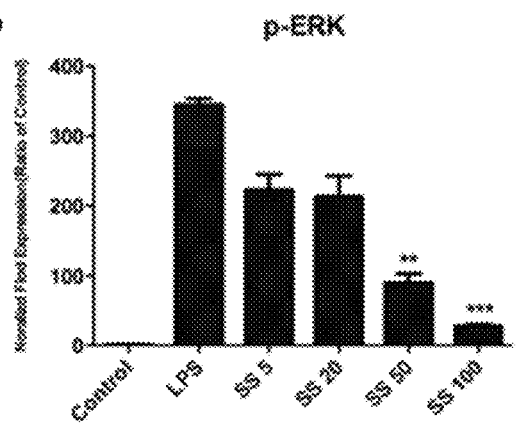
Figure 8A:
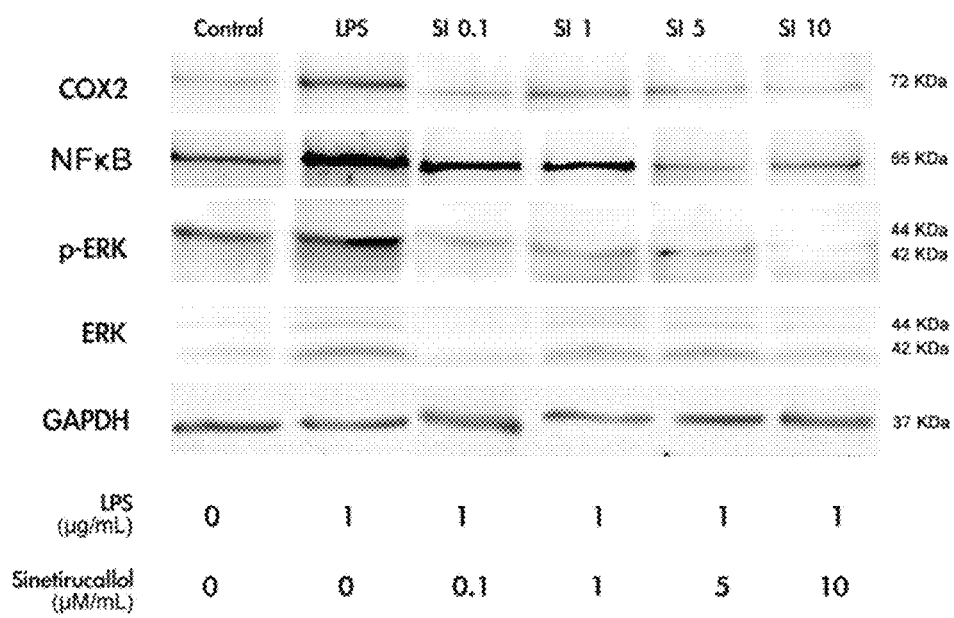
FIGS. 8A-8D show SI inhibited expression of COX-2, NFκB, p-ERK, and ERK of RAW264.7 cells. Treatment difference concentration (0.1, 1, 5, and 10 μM) of SI were employed to treat in LPS-induced RAW 264.7 cells for 12 h. Cell were lysed in RIPA buffer for Western blot.
Figure 8B:
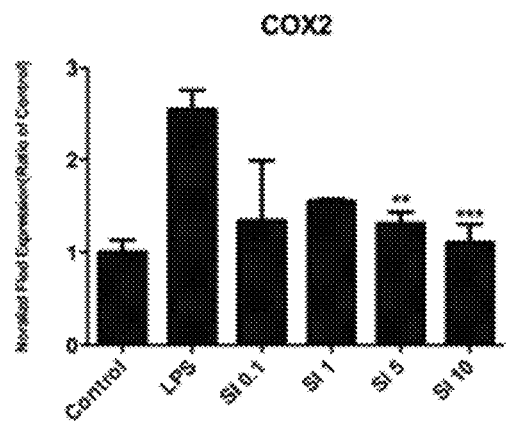
Figure 8C:
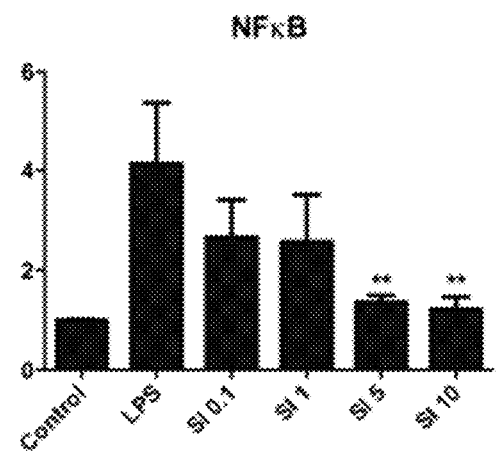
Figure 8D:
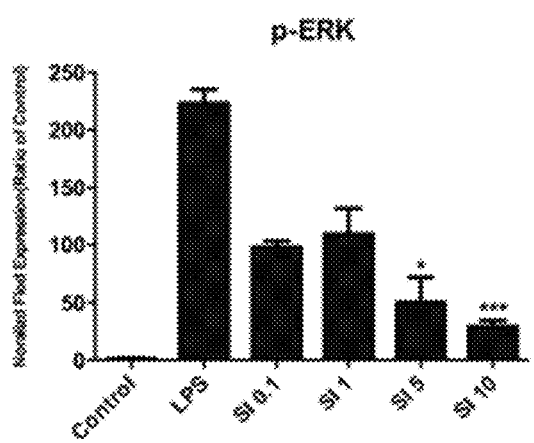
Figure 26:
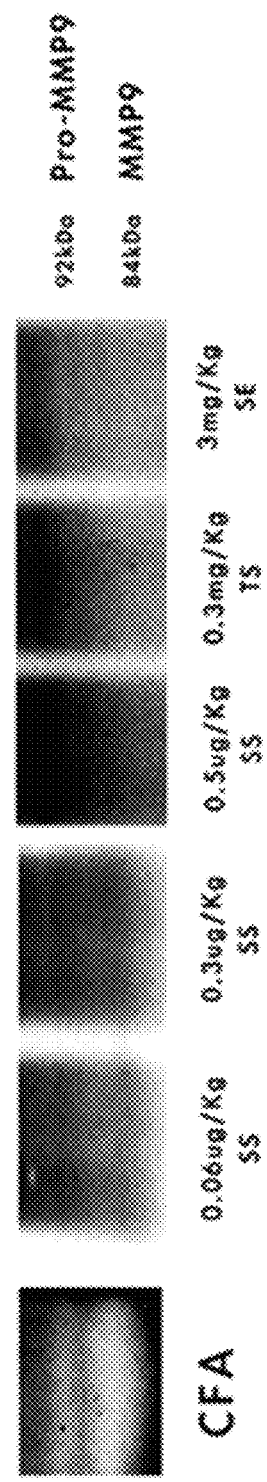
FIG. 26 depicts a portion of a gel showing the inhibitory effect of *Spiranthes sinensis* extract on MMP9 activity.

Zymography was applied to measure the effects of SI on blood MMP2 and MMP9 of CFA-induced inflammation mice. The CFA-induced inflammation mice had higher MMP2 and MMP9 expression in the blood (FIG. 4). The MMP quantifications revealed that MMP9 levels were reduced in CFA-induced mice in the treatment SI groups with different concentration. 0.44 μg/kg of SI had inhibitory effect on the activity of MMP9, but less significant in MMP2 level. Results for the SS samples are illustrated in FIG. 26, and indicate that *Spiranthes sinensis* extract has an inhibitory effect on the activity of MMP9, a kind of gelatinase that is up-regulated during liver fibrosis.

Example 5: Effect of *Spiranthes sinensis* Extract and Sinetirucallol on IL-1β, IL-6, iNOs, and TNF-α mRNA Expression of LPS-Induced in RAW 264.7 Cells Methods Cell Culture The RAW264.7 murine macrophage cell line was purchased from the Bioresource Collection and Research Center (BCRC, Taiwan). The cells were incubated at 37° C. in 5% $CO_2$ in Dulbecco's modified Eagle's medium (DMEM; Gibco Inc., NY, USA) supplemented with 100 U/mL penicillin, 100 μg/mL sodium pyruvate and 10% fetal bovine serum (FBS; Gibco Inc.).

The cells were also treated with 0.01% DMSO as a vehicle control. The cells were seeded into 12-well plates at a density of $6×10^5$ cells/well in 24 h then incubated with 0.1% BSA with serum-free medium 3 h, treated with different concentrations of *Spiranthes sinensis* extract or SI then incubated in the presence of LPS (1 μg/mL) for 4 h.

Real-Time PCR

Total RNA was prepared from freshly harvested RAW 264.7 cells and was isolated using Trizol extraction. RNA samples were frozen at −80° C. until analyzed. cDNA was then made using an M-MLV RT kit (Invitrogen, Carlsbad, Calif.) according to the manufacturer's protocol. The expression of selected cytokine and related genes in mouse tissue and in RAW264.7 cells exposed to the present *Spiranthes sinensis* extract was determined by the SensiFAST SYBR No-ROX Kit (BIOLINE, London, UK), as described previously. PCR cycling conditions for TNF-Alpha included a 95° C. heating step for 2 min at the beginning of every run. The tubes were then cycled at 95° C. for 5 sec, annealed at 60° C. for 10 sec, and extended at 72° C. for 20 sec for forty cycles. PCR conditions for iNOs, IL6, and IL included a 95° C. heating step for 2 min at the beginning of every run. The tubes were then cycled at 95° C. for 5 sec, annealed at 64° C. for 10 sec, and extended at 72° C. for 20 sec for thirty-eight cycles. In all cases, optical data were collected during the annealing phase. In order to quantify expression represented by each of the PCR products, an internal reference by β-actin. The primers used in the real-time PCR of this example were listed in Table 1.

Data are expressed as means±S.E. Statistical comparisons of the results were made using one-way analysis of variance (ANOVA). Means within each column followed by the different letters were significantly different at $p<0.05$ by Turkey's test.

TABLE 1

Primers for Real-time PCR

| Name | Sequences 5'->3' | SEQ ID NO |
|---|---|---|
| β-actin Forward | AGT GGT ACG ACC AGA GGC ATA C | SEQ ID NO 1 |
| β-actin Reverse | ATG GGT CAG AAG GAC TCC TAC G | SEQ ID NO 2 |
| iNOs Forward | TCC TAC ACC ACA CCA AAC | SEQ ID NO 3 |
| iNOs Reverse | CTC CAA TCT CTG CCT ATC C | SEQ ID NO 4 |
| TNF α Forward | AAC CCT CTG GCC CAA GGA | SEQ ID NO 5 |
| TNF α Reverse | GGC GAC GGG CTT ATC TGA | SEQ ID NO 6 |
| Interleukins IL-6 Forward | ATG AAC TCC CTC TCC ACA AGC | SEQ ID NO 7 |
| Interleukins IL-6 Reverse | TGG CTT TGT CTG GAT TCT TTC | SEQ ID NO 8 |
| Interleukins IL-1β Forward | AAA GGG GAC TTG AAG AGA G | SEQ ID NO 9 |
| Interleukins IL-1β Reverse | CTG CTT GAG AGG TGC TGA TGT | SEQ ID NO 10 |
| NLRP3 Forward | GCG TTT GTT GAG GCT CAC ACT | SEQ ID NO 11 |
| NLRP3 Reverse | TGA AGA AGA TTA CCG TAA GAA GTA CAG A | SEQ ID NO 12 |
| Interleukins IL-33 Forward | GAT GGG AAG AAG CTG ATG GTG | SEQ ID NO 13 |
| Interleukins IL-33 Reverse | TTG TGA AGG ACG AAG AAG GC | SEQ ID NO 14 |

Results

Figure 25:
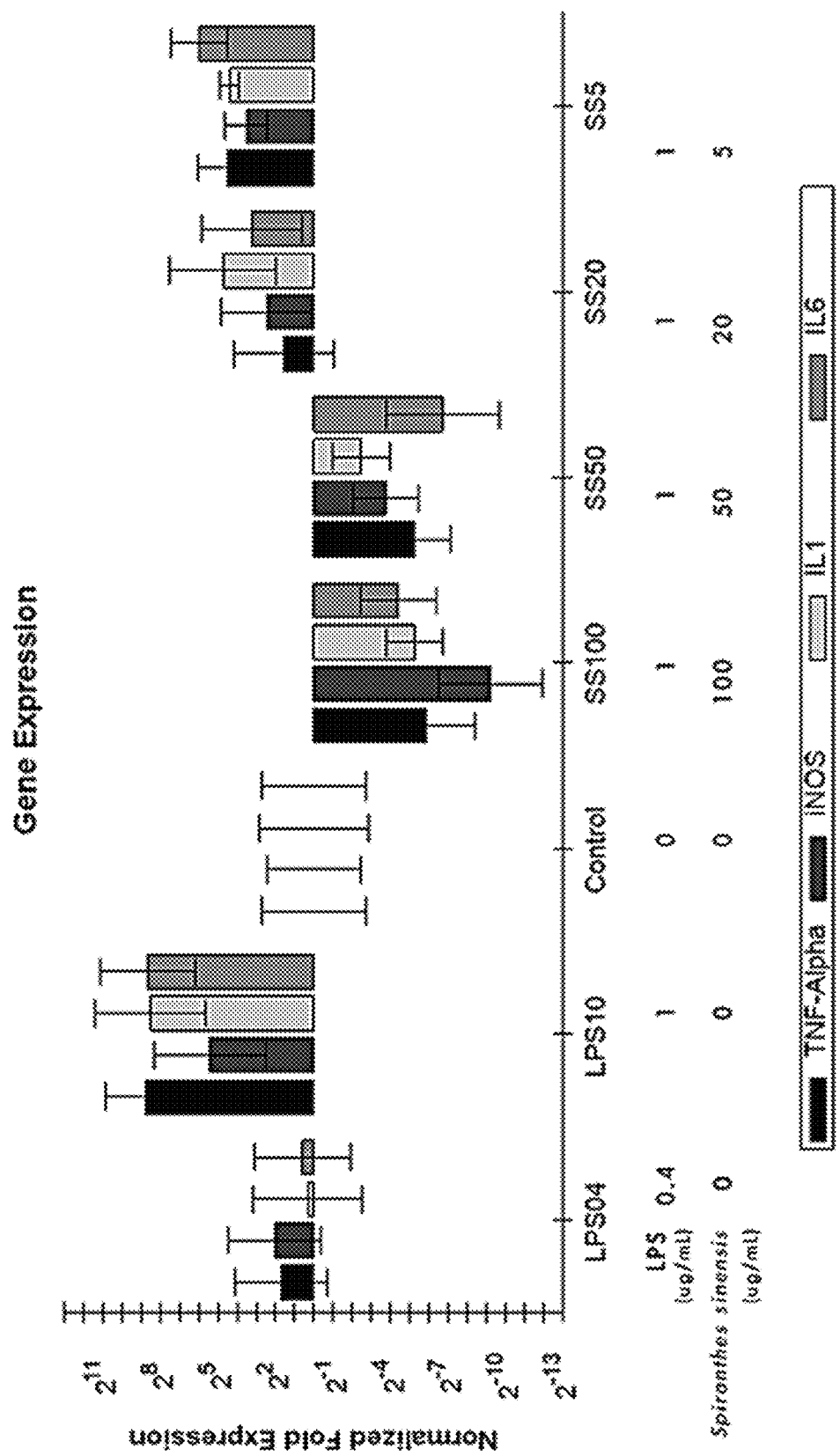
FIG. 25 illustrates the results of real time PCR assays.

Next, we investigated the effect of *Spiranthes sinensis* extract (FIG. 5) and SI (FIG. 6) on LPS-induced IL-1β, IL-6, and IL-33 release. Results indicated that the *Spiranthes sinensis* extract diminished LPS-induced inflammatory cytokine IL-1β and IL-6 transcription in a dose-dependent manner. We found that TNF-α, NLRP3, and iNOs mRNA levels were also significantly decreased by 50 μg/mL of *Spiranthes sinensis* extract with similar trend. And 5 μM SI had the better inhibition of inflammatory cytokine transcription. RAW264.7 cells after *Spiranthes sinensis* extract or SI treatment with a dose-dependent manner was found. An alternative illustration of the results for *Spiranthes sinensis* extract is provided in FIG. 25.

Example 6: Effect of *Spiranthes sinensis* Extract and Sinetirucallol on the Expression of COX-2, NFκB and Phosphor ERK Activation in LPS-Induced RAW264.7 Cells Methods
Cell Culture The RAW264.7 murine macrophage cell line was purchased from the Bioresource Collection and Research Center (BCRC, Taiwan). The cells were incubated at 37° C. in 5% $CO_2$ in Dulbecco's modified Eagle's medium (DMEM; Gibco Inc., NY, USA) supplemented with 100 U/mL penicillin, 100 μg/mL sodium pyruvate and 10% fetal bovine serum (FBS; Gibco Inc.).

The cells were also treated with 0.01% DMSO as a vehicle control. The cells were seeded into 12-well plates at a density of $6 \times 10^5$ cells/well in 24 h then incubated with 0.1% BSA with serum-free medium 3 h, treated with different concentrations of *Spiranthes sinensis* extract or SI then incubated in the presence of LPS (1 μg/mL) for 4 h.
Western Blot The concentrations of proteins from whole-cell lysates were determined by Bradford assay. Equal amounts of protein were separated by SDS-PAGE and transferred onto nitrocellulose membranes. The blots were then blocked overnight with 5% (wt/vol) nonfat dry milk, and probed with COX-2, NFκB, phospho-specific antibodies to ERK and ERK antibodies in 5% (wt/vol) BSA dissolved in TBS/T (20 mM Tris-HCl buffer, pH 7.6, containing 137 mM NaCl and 0.05% (vol/vol) Tween-20). With the use of horseradish peroxidase-conjugated secondary anti-rabbit or anti-mouse antibody, bound antibodies were detected by enhanced chemiluminescence. The signals were monitored using Western Lightning™ Plus-ECL (Perkin Elmer Life Sciences) and the PVDF membrane was exposed to Luminescent image analyzer LAS-3000 (Fujifilm, Minato, Tokyo, Japan). Acquired data were analyzed and compared the difference among treatments.

Data are expressed as means±S.E. Statistical comparisons of the results were made using one-way analysis of variance (ANOVA). Means within each column followed by the different letters were significantly different at p<0.05 by Turkey's test.
Results Western blot was employed to investigate the effect of *Spiranthes sinensis* extract and SI on the alteration of COX-2, NFκB, p-ERK, and ERK in LPS-induced RAW264.7 cells. The activation of ERK and the up-regulation of COX-2 protein expression were seen at 12 h by LPS-induced in RAW264.7 cells. LPS was treatment RAW264.7 cells for 12 h increased the COX-2 and NFκB expression about 2-fold over the basal level with and phosphorylation of ERK expression about 250-fold. The *Spiranthes sinensis* extract (FIG. 7) and SI (FIG. 8) diminished LPS-induced inflammatory cytokine and iNOs expression of COX-2 and NFκB as well as the phosphorylation of ERK in a dose-dependent manner.

Example 7: Effect of *Spiranthes sinensis* Extract and Sinetirucallol on NO Production in RAW264.7 Cells Methods
In LPS-Induced RAW264.7 Cells
Methods
Cell Culture The RAW264.7 murine macrophage cell line was purchased from the Bioresource Collection and Research Center (BCRC, Taiwan). The cells were incubated at 37° C. in 5% $CO_2$ in Dulbecco's modified Eagle's medium (DMEM; Gibco Inc., NY, USA) supplemented with 100 U/mL penicillin, 100 μg/mL sodium pyruvate and 10% fetal bovine serum (FBS; Gibco Inc.).

The cells were also treated with 0.01% DMSO as a vehicle control. The cells were seeded into 12-well plates at a density of $6 \times 10^5$ cells/well in 24 h then incubated with 0.1% BSA with serum-free medium 3 h, treated with different concentrations of *Spiranthes sinensis* extract or SI then incubated in the presence of LPS (1 μg/mL) for 4 h.
Nitrite Quantification NO production from activated RAW 264.7 cells was determined by measuring the amount of nitrite, a stable oxidation product of NO. An aliquot of the conditioned medium was mixed with an equal volume of 1% sulfanilamide in water and 0.1% N-1-naphthylethylenediamine dihydrochloride in 5% phosphoric acid. The absorbance was determined at 550 nm. Sodium nitrite, diluted in culture media at concentrations of 10-100 μM, was used to generate a standard curve.

Figure 9A:
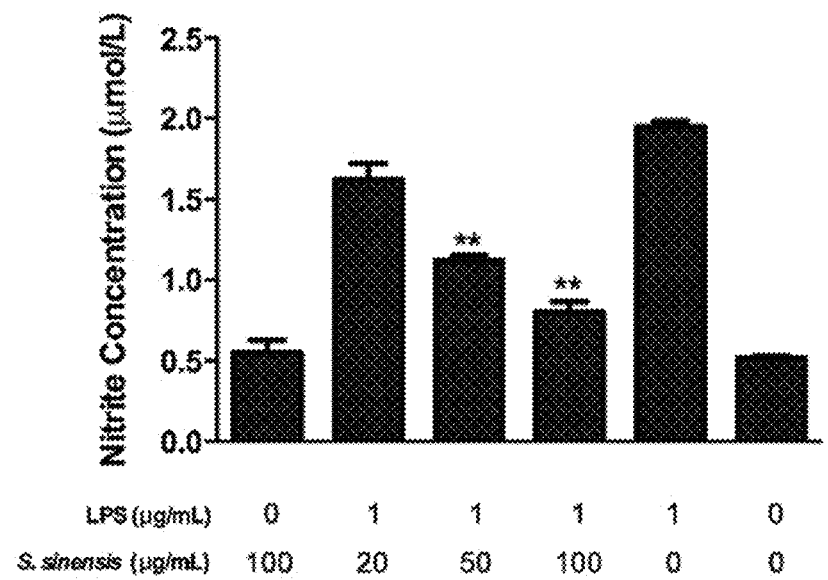
FIGS. 9A-9B show effect of (FIG. 9A) *Spiranthes sinensis* extract and (FIG. 9B) SI on NO release of RAW264.7 cells. Treatment difference concentration of *Spiranthes sinensis* extract (5, 20, 50, and 100 μg/mL) or SI (0.1, 1, 5, and 10 μM) were employed to treat in LPS-induced RAW 264.7 cells for 12 h. Conditioned medium was collected and centrifuged to remove the cell debris for NO assay. The values represent the means±S.E. of three independent experiments. P<0.01; *P<0.001 as compared with 1 μg/mL of LPS group.
Figure 9B:
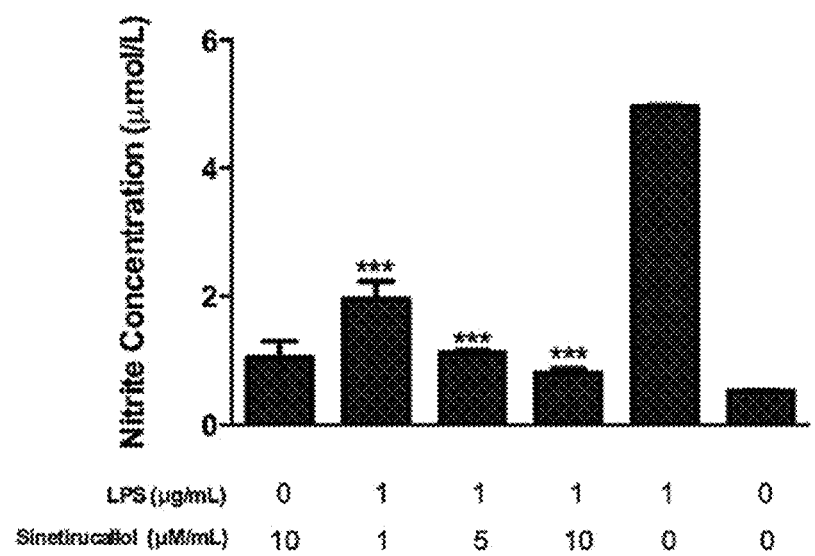

Data are expressed as means±S.E. Statistical comparisons of the results were made using one-way analysis of variance (ANOVA). Means within each column followed by the different letters were significantly different at p<0.05 by Turkey's test.
Results The amount of nitrite, a stable metabolite of NO, was used as the indicator of NO production in the medium. When 1 μg/mL of LPS was added, NO production was dramatically increased to 2.0±0.57 μM. To assess the effect of *Spiranthes sinensis* extract or SI on LPS-induced NO production in RAW 264.7 cells, the cells were treated with 1 μg/mL of LPS for 12 h after treatment *Spiranthes sinensis* extract (5, 20, 50, and 100 μg/mL) or SI (0.1, 1, 5, and 10 μM) for 12 h (FIG. 9). *Spiranthes sinensis* extract and SI contained inhibitory effect on NO production in LPS-induced RAW264.7 cells with a dose-dependent manner. We also tested only treatment with *Spiranthes sinensis* extract and SI for NO production to ensure that the plant extract alone did not contribute to inflammation.

Example 8: Anti-Oxidant Activity of *Spiranthes Sinensis* Extract In Vivo

Methods
Cell Culture

The RAW264.7 murine macrophage cell line was purchased from the Bioresource Collection and Research Center (BCRC, Taiwan). The cells were incubated at 37° C. in 5% $CO_2$ in Dulbecco's modified Eagle's medium (DMEM;

Gibco Inc., NY, USA) supplemented with 100 U/mL penicillin, 100 μg/mL sodium pyruvate and 10% fetal bovine serum (FBS; Gibco Inc.).

The cells were also treated with 0.01% DMSO as a vehicle control. The cells were seeded into 12-well plates at a density of $6\times10^5$ cells/well in 24 h then incubated with 0.1% BSA with serum-free medium 3 h, treated with different concentrations of *Spiranthes sinensis* extract or SI then incubated in the presence of LPS (1 μg/mL) for 4 h.

DPPH Assay

The DPPH radical scavenging activity of *Spiranthes sinensis* extract or SI was determined as previously described (Sharma et al. 2009). In brief, the reaction mixtures containing varying concentrations of *Spiranthes sinensis* extract and 0.04 mM DPPH (SIGMA, #D9132) in a 96-well plate were incubated at 37° C. for 30 min, and the absorbance was measured at 490 nm. Vitamin C was used as a positive control.

Results

Figure 10:
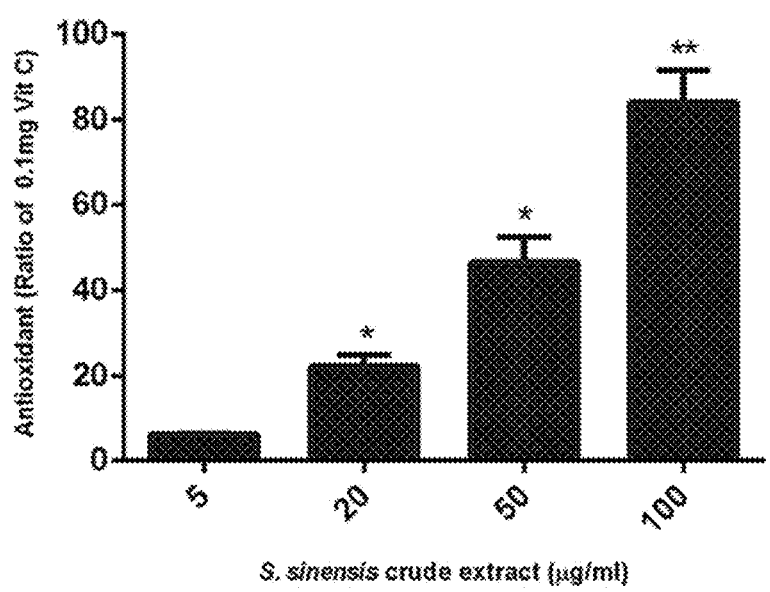
FIG. 10 shows anti-oxidant activity of *Spiranthes sinensis* extract by DPPH assay. The values represent the means±S.E. of three independent experiments. *P<0.05; **P<0.01 as compared with 5 μg/mL of the *Spiranthes sinensis* extract group.

During inflammation, various cells as macrophages are activated including the respiratory burst, in which a large increase of oxygen uptake results in massive release of ROS (Yang et al. 2011). The 100 μg/mL of *Spiranthes sinensis* extract has comparable ability with Vitamin C of 0.1 mg/mL in anti-oxidation (FIG. 10).

Example 9: THSCs and NHSCs Cell Culture and Viability

NHCSs and THSCs Cell Culture

Hepatic Stellate Cells (HSCs), a non-parenchymal cell, is a major cell type involved in liver fibrosis, which typically involves the formation of scar tissue in response to liver damage. In normal liver, HSCs are in a quiescent form, and are a principal storage site of vitamin A and lipids. The stored amount of vitamin A decreases progressively in liver injury. When the liver is damaged, stellate cells are changed into an activated state (Hjelkrem, Morales et al. 2012). The activated stellate cell is characterized by proliferation, contractility, and chemotaxis. Therefore, the quiescent form of HSC can be used as an indication of liver condition.

Non chemical-induced hepatic stellate cells (NHSCs >95% purity) were isolated from male Sprague-Dawley rat liver, and thioacetamide (TAA)-induced hepatic stellate cells (THSCs >95% pure) were isolated from TAA (Fluka) induced fibrotic liver of male Sprague-Dawley rat as our previous study described. Both the cell lines were maintained in DMEM (pH 7.4) supplemented with 10% FBS, and incubated at 37° C. with 5% CO2 in water saturated incubator. Media was changed in every 2 days and the cells were passage during 80%-90% confluence using trypsin/EDTA (Sigma-Aldrich).

Cell Viability

In order to examine the bio-compatibility of the extract of the present disclosed composition, a MTT assay (3-(4,5-dimethylthiazol-2-yl)-2,5-diphenyltetrazolium bromide (MTT, Invitrogen), a colorimetric based assay) is performed.

MTT Assay

The 3-(4,5-dimethylthiazol-2-yl)-2,5-diphenyltetrazolium bromide (MTT, Invitrogen) a colorimetric based assay was performed to analyze the viable cells. $8\times10^3$ of cells per well were seeded in 96-well plates. Cells were treated with different concentrations of *Spiranthes sinensis* extract or SI for 24 h, after incubation 20 μL (5 mg/mL) of MTT solution was added per well and further incubated for 4 h. The media was removed, and formazan was solubilized by adding 100 μL/well of DMSO (Sigma-Aldrich) and OD was measured at 570 nm using a ELISA reader. Percentage of viable cells was estimated by comparing with untreated control cells. The average absorbance value of the control cells was taken as 100% viability.

Figure 11:
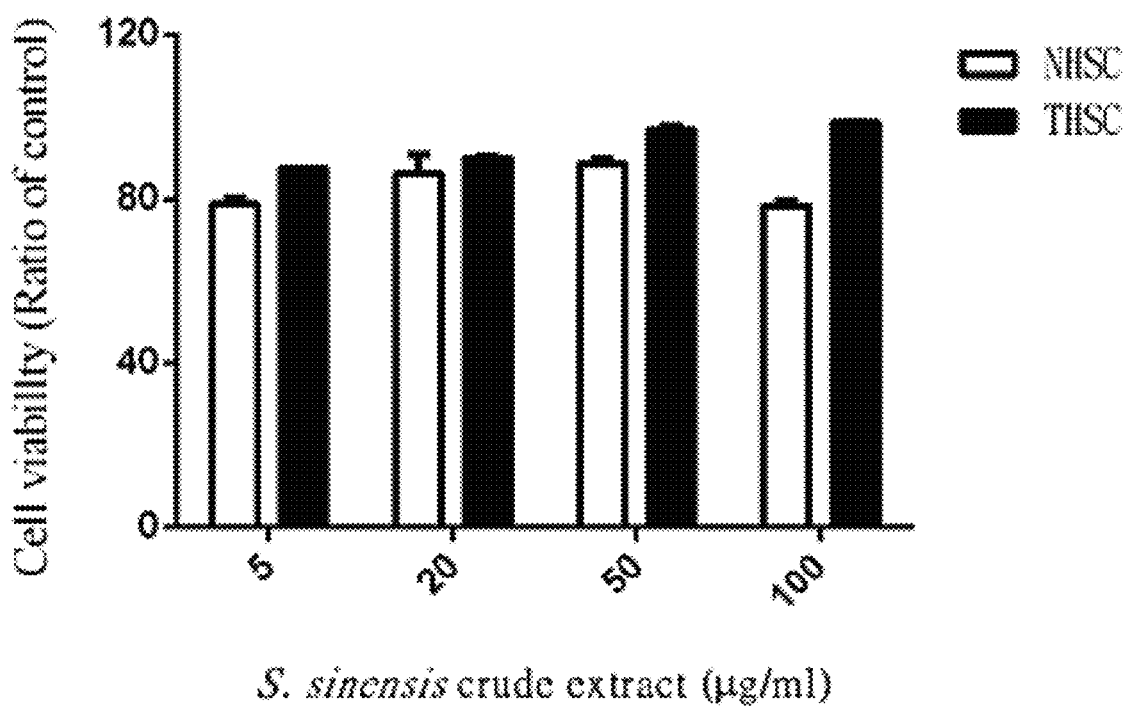
FIG. 11 shows the cell viability experiments for NHSCs and THSCs by using MTT assay. The cells were treated with the *Spiranthes sinensis* extract at various concentrations of 5, 20, 50, and 100 μg/mL for 24 h. The concentration is based on the volume of the culture medium.

The results in FIG. 11 showed that the extract of *Spiranthes sinensis* substantially had no harm to the cells at given dosages.

Example 10: Effect of *Spiranthes sinensis* Extract on Lipid Accumulation

Methods

The Oil Red O staining and the AdipoRed assay were performed to examine the effect of *Spiranthes sinensis* extract in lipid accumulation.

Data are expressed as means±S.E. Statistical comparisons of the results were made using one-way analysis of variance (ANOVA). Means within each column followed by the different letters were significantly different at $p<0.05$ by Turkey's test.

Oil Red O Staining Assay

Briefly, $1\times10^5$ of cells per well (NHSCs or THSCs) were seeded in 6-well plates and were incubated in 5% $CO_2$ at 37° C. overnight for confluence. Afterward, cells were treated with various concentrations (5, 20, and 50 μg/mL) of the present *Spiranthes sinensis* extract for 24 h, respectively. Cells were washed twice with PBS, and then fixed by 3.7% paraformaldehyde (pre-warmed) for 10 min. Oil red O stock solution 0.5% (w/v) filtered, and stained at RT under the dark for 1 h. Cells were washed with 50% isopropanol for 5 sec and counterstained with Hematoxylin (Sigma-Aldrich) for 1 min. Cells were washed with distilled water for three times and stored using glycerol. Images were acquired using ZEISS inverted microscope connected with Canon 700 D camera.

Results

Figure 13:
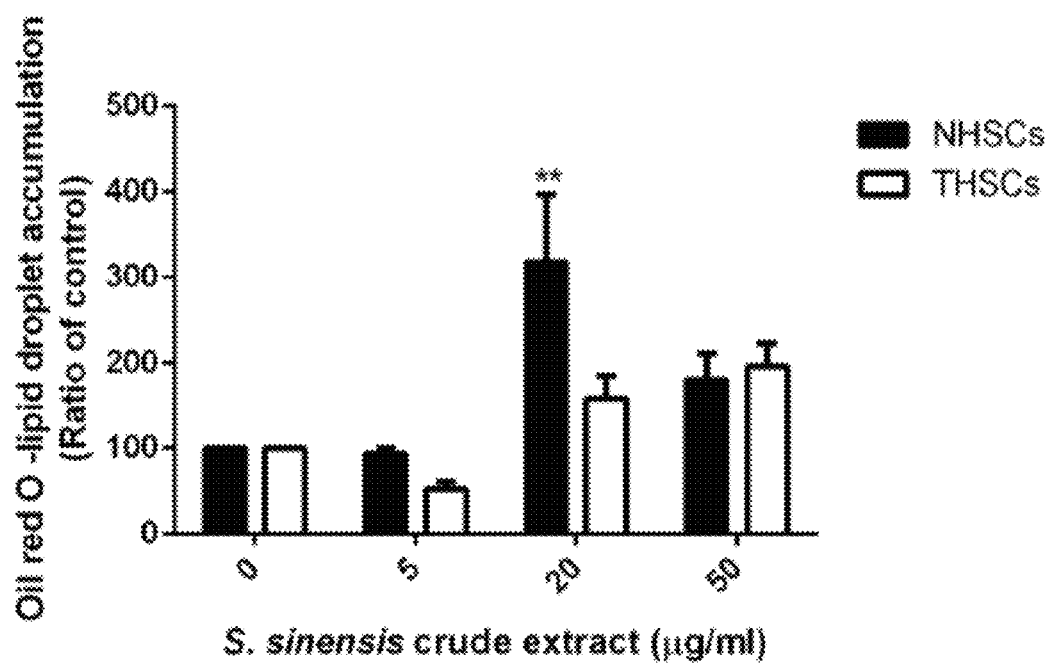
FIG. 13 depicts a bar diagram showing the quantitation from the results of the experiments shown in FIG. 12.

The results are shown in FIG. 12. It is noted that, the present *Spiranthes sinensis* extract increased the abundant perinuclear lipid droplets both in NHSCs and THSCs when compared with the control group. The results of FIG. 12 were also quantified as the bar chart shown in FIG. 13 from which it was more obvious that the treatment of the present *Spiranthes sinensis* extract respectively increased the fatty acid storage of NHSCs and THSCs in about 3 fold and about 1.5 fold compare with the untreated control groups.

AdipoRed Assay

Approximately $1\times10^4$ of cells per well were seeded in 96-well plates and incubated in 5% CO2 at 37° C. overnight. Cells were treated with various concentrations (5, 20, 50, and 100 μg/mL) of *Spiranthes sinensis* extract for 48 h. After incubation, the culture supernatant was removed and each well carefully rinsed with 200 μL of PBS. And then, each well was filled with 200 μL of PBS and 5 μL of AdipoRed Reagent (Lonza, Walkersville, Md., USA). After incubation at room temperature for 10 min, placed the plate in the fluorimeter and fluorescence with excitation at 485 nm and emission at 572 nm (Multimode Plate Reader, PerkinElmer Inc Waltham, Mass., USA) was acquired.

Results

Figure 14:
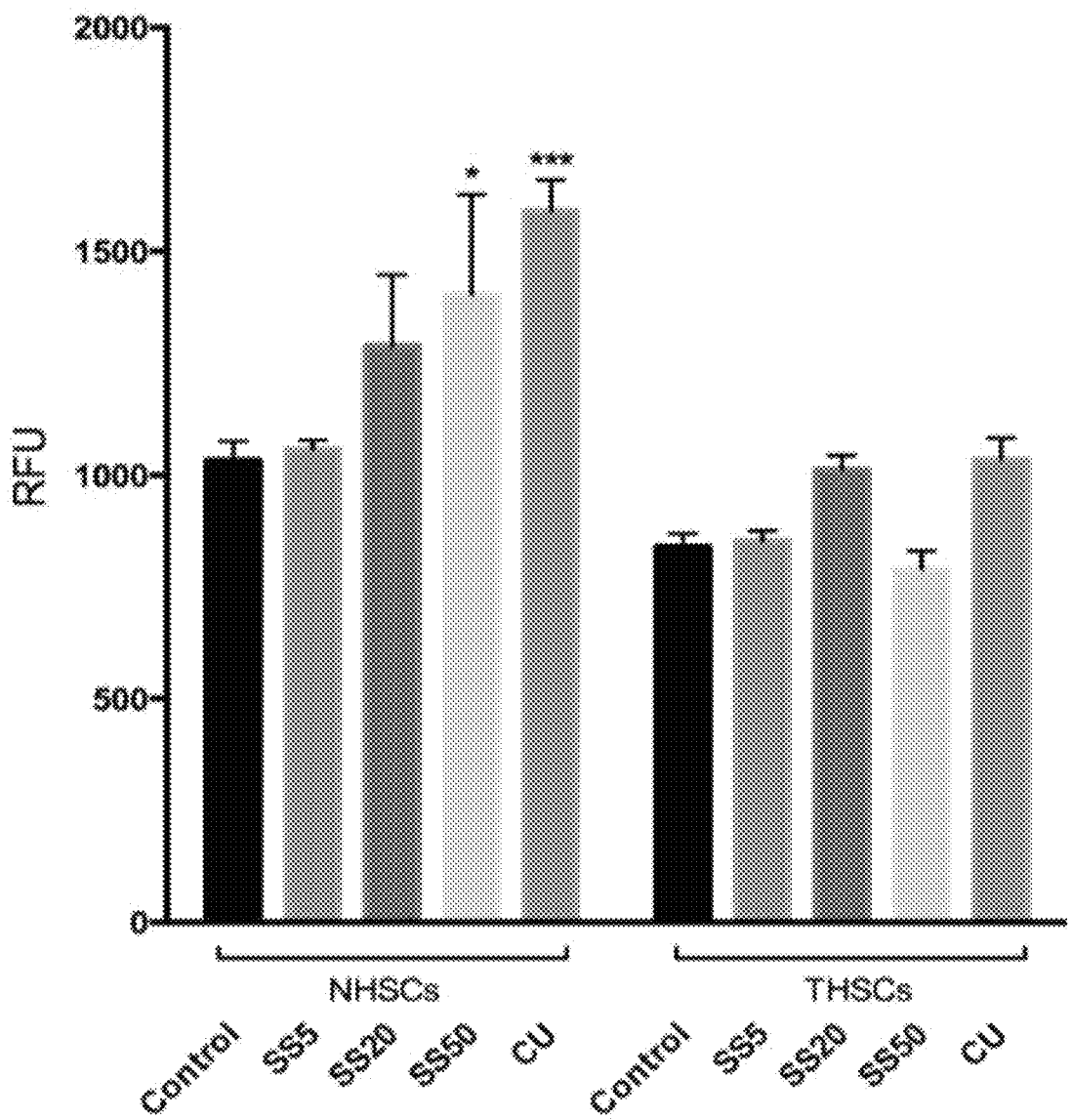
FIG. 14 shows the effect of *Spiranthes sinensis* extract (5, 20, and 50 μg/mL) and curcumin (25 μM) on fatty acid storage in NHSCs and THSCs at 48 h. *p<0.05; ***p<0.001 as compared with the control group.

The result (FIG. 14) shows that the *Spiranthes sinensis* extract increased the lipid accumulation in NHSCs (1.8 fold) and THSCs (1.4 fold) when compared with the control group. The observation was consistent with the results of the aforesaid Oil red O staining assay and further verified the capability of the present *Spiranthes sinensis* extract in lipid accumulation.

Example 11: Effect of *Spiranthes sinensis* on Collagen Accumulation

Methods

The Sirius Red stain was used for examining the effect of the present *Spiranthes sinensis* extract in Collagen accumulation. Briefly, $3 \times 10^4$ of cells per well were seeded in 12-well plates and are incubated in 5% CO2 at 37° C. overnight for confluence. Afterward, cells were treated with various concentrations (5, 20, and 50 μg/mL) of the present *Spiranthes sinensis* extract for 24 h, respectively. Cells were washed twice with PBS, and then fixed by 3.7% paraformaldehyde (pre-warmed) for 10 min. Picro-Sirius Red solution (ScyTek, Logan, Utah, USA) was stained at RT under the dark for 1 h. Cells were washed twice with ddH2O and counterstained with Hematoxylin (Sigma-Aldrich) for 1 min. Cells were washed with distilled water for three times and stored using glycerol. Images were acquired using ZEISS inverted microscope connected with Canon 700 D camera.

Data are expressed as means±S.E. Statistical comparisons of the results were made using one-way analysis of variance (ANOVA). Means within each column followed by the different letters were significantly different at $p<0.05$ by Turkey's test.

Results

The results are shown in FIG. 15. Both NHSCs and THSCs treated with *Spiranthes sinensis* extract (5, 20, and 50 μg/mL) for 24 h showed reduced perinuclear collagen comparing with the control groups.

Example 12: Effect of *Spiranthes sinensis* Extract on the Expression of COL1 I, COL1 III, TGF-β R1, TGF-β R2, RXRα, NrF2 and PPARγ

Methods

The expressions of COL1 III (collagen alpha 1 type III), COL1 I (collagen alpha 1 type I), TGF-β R1 (TGF-β Receptor 1), TGF-β R2 (TGF-β Receptor 2), RXRa (retinoidxreceptor), NrF2 (Nuclear factor (erythroid-derived 2)-like 2) and PPARγ (peroxisome proliferator-activated receptor y) were examined by Real-time PCR; wherein 18S is used as a control.

For RNA isolation and cDNA synthesis, $4 \times 10^5$ of HSCs were seeded into 6-well plates, after 70 to 80% confluence, and then treated with different concentrations (5, 20, 50, and 100 μg/mL) of the present *Spiranthes sinensis* extract in DMEM containing 5% FBS for 8 and 12 h, respectively. The positive control group was treated with 25 μM of curcumin. Total RNA was prepared from freshly harvested HSCs and was isolated using Trizol extraction. RNA samples were frozen at −80° C. until analyzed. cDNA was then made using an M-MLV RT kit (Invitrogen, Carlsbad, Calif.) according to the manufacturer's protocol.

For Real-time PCR, the SensiFAST SYBR No-ROX Kit (BIOLINE, London, UK) was used. PCR cycling conditions for RXRα, NrF2 and PPARγ included a 95° C. heating step for 2 min at the beginning of every run. The tubes were then cycled at 95° C. for 5 sec, annealed at 64° C. for 10 sec, and extended at 72° C. for 20 sec for forty cycles. PCR conditions for collagen alpha 1 type III, collagen alpha 1 type I, TGF-β Receptor 1, and TGF-β Receptor 2 included a 95° C. heating step for 2 min at the beginning of every run. The tubes were then cycled at 95° C. for 5 sec, annealed at 62° C. for 10 sec, and extended at 72° C. for 20 sec for 45 cycles. In all cases, optical data were collected during the annealing phase. In order to quantify expression represented by each of the PCR products, an internal reference by 18S. The primer sets used in this example were listed in Table 2.

Data are expressed as means±S.E. Statistical comparisons of the results were made using one-way analysis of variance (ANOVA). Means within each column followed by the different letters were significantly different at $p<0.05$ by Turkey's test.

Results

FIG. 16 shows that NHSCs and THSCs treated with the present *Spiranthes sinensis* extract for 8 h had reduced expression of COL1 I, COL1 III, TGF-βR1, and TGF-βR2.

FIG. 17 and FIG. 18 show that RXRα, NrF2 and PPARγ gene expression increased in both NHSCs and THSCs treated with the present *Spiranthes sinensis* extract for 12 h treatment.

TABLE 2

Primer sets for Real-time PCR

| Name | Sequence 5'->3 | SEQ ID NO |
|---|---|---|
| 18S Forward | ACG GAC CAG AGC GAA AGC AT | SEQ ID NO 15 |
| 18S Reverse | TGT CAA TCC TGT CCG TGT CC | SEQ ID NO 16 |
| PPARγ Forward | AGC ATG GTG CCT TCG CTG ATG C | SEQ ID NO 17 |
| PPARγ Reverse | AAG TTG GTG GGC CAG AAT GGC A | SEQ ID NO 18 |
| Collagen alpha 1 type III Forward | GAA AAA ACC CTG CTC GGA ATT | SEQ ID NO 19 |
| Collagen alpha 1 type III Reverse | GGA TCA ACC AGT ATT CTT CCA CTC T | SEQ ID NO 20 |
| TGF-β Receptor 1 Forward | CAT CGG CAA AGG TCG GTT T | SEQ ID NO 21 |
| TGF-β Receptor 1 Reverse | AAT ATC TTC ACG GCA ACT TCT TCT C | SEQ ID NO 22 |
| TGF-β Receptor 2 Forward | TCA CCT ACC ACG GCT TCA CTC T | SEQ ID NO 23 |
| TGF-β Receptor 2 Reverse | CGC CCT TTT CTT TTC CTT CA | SEQ ID NO 24 |
| RXRα Forward | GCC GGC CTC TGA CTG TGA | SEQ ID NO 25 |
| RXRα Reverse | GCA CCA CAA TGT CCC AGT GA | SEQ ID NO 26 |
| NrF2 Forward | GAC AAA CAT TCA AGC CGA TTA GAG G | SEQ ID NO 27 |
| NrF2 Reverse | ACT TTA TTC TTC CCT CTC CTG CGT | SEQ ID NO 28 |

Example 13: Effect of *Spiranthes sinensis* on Tissue Injury/Wound Healing

Methods

Rats were separated into 2 groups: control group animals treated with sterile gauze, and *Spiranthes sinensis* extract (SS) group animals treated with 5% *Spiranthes sinensis* extract with white vaselin and sterile gauze. The skin of the dorsal region of rats was injured and the wound was applied with treatments to evaluate the effect of *Spiranthes sinensis* extract on wound healing. The wound size (1.5 cm×1.5 cm) of each rat was measured and recorded. The wound was treated with control or *Spiranthes sinensis* extract and was observed at 0, 1st, 2ed, 3rd, 5th, 6th, 7th, 9th 12th, and 13th day. Scar tissue excision was performed on the 14th day and histopathological examination was performed by staining with haematoxylin and eosin. The wound healing sizes and rates were calculated using ImageJ software.

Results

Figure 19:
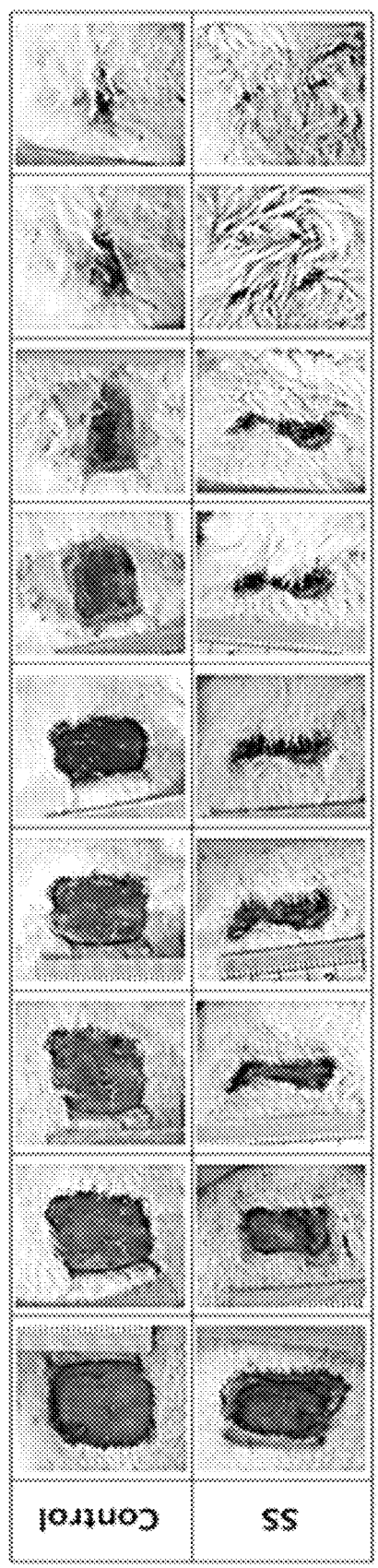
FIG. 19 illustrates the images of wound healing in the dorsal skin of control group and *Spiranthes sinensis* extract (SS) group rats. Control rats are treated with sterile gauze only. SS group rats are treated with white vaseline plus 5% *Spiranthes sinensis* extract with sterile gauze. SS group rats show rapid wound healing in response to treatment and the healing is consistent as the wound continues to heal. Wound healing in SS group rats is faster than wound healing in control rats.
Figure 20:
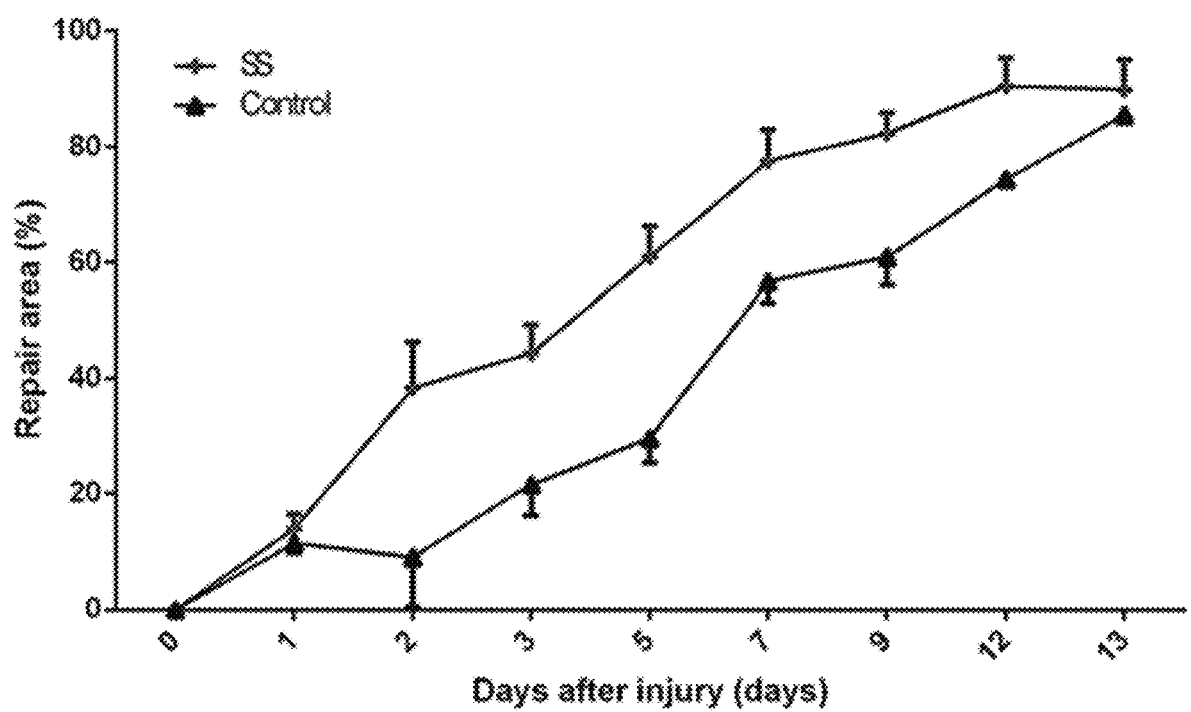
FIG. 20 shows the area of repair in wounds in the dorsal skin of control group rats and SS group upon treatment over 13 days of observation. The repair area (%) is represented by the area of repair verse the area of wound.
Figure 21:
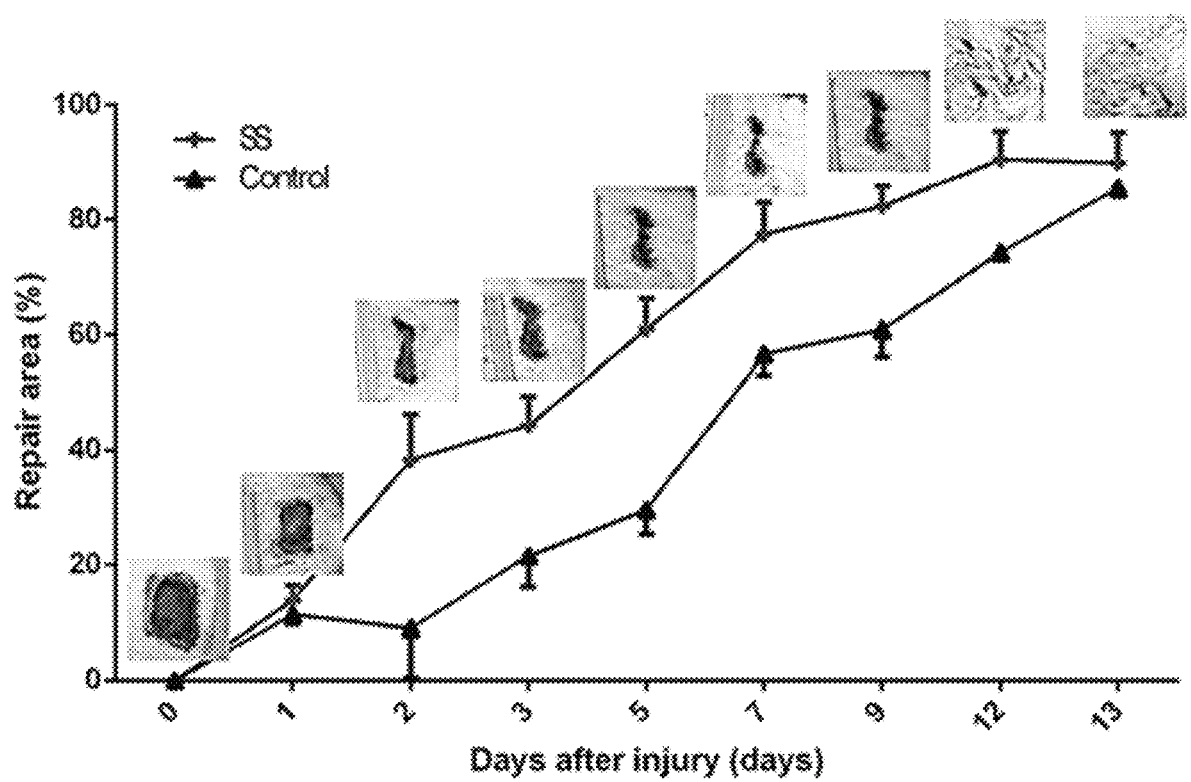
FIG. 21 depicts the tissue sections of wound areas in control group and SS group rats. Shown are the healing wound sizes in control group and SS-treated group animals.
Figure 22B:
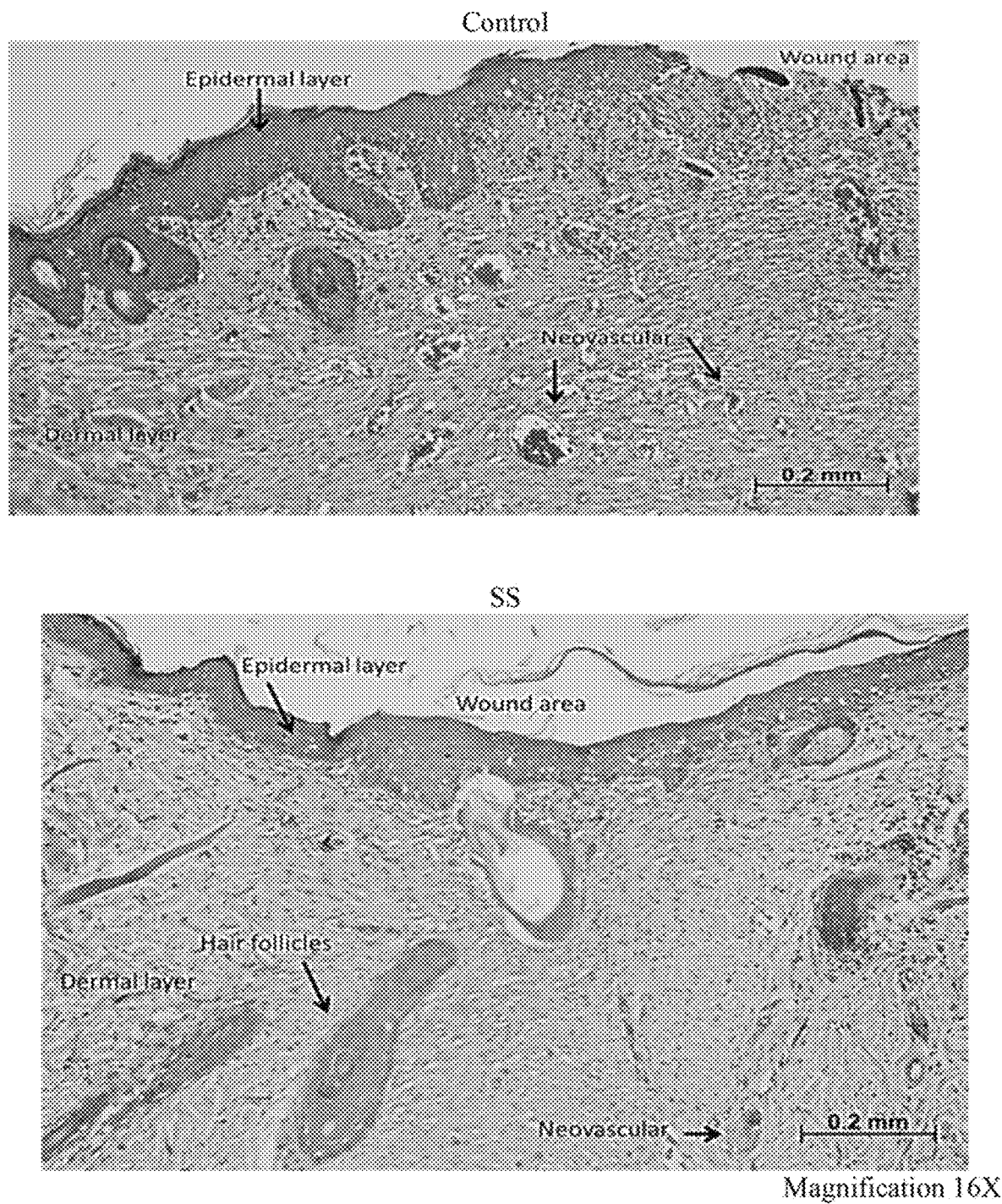

FIG. 19 shows the wound healing progress of rat skin in response to treatments. Rats treated with *Spiranthes sinensis* extract showed extensive and gradual recovery compared with rats in the control group. FIGS. 20 and 21 show the change of repair area in SS group and control group rats. Moreover, this beneficial effect was demonstrated by tissue sections (FIG. 22). The SS group rats showed completion of epidermal and dermal layers of skin in the wound area, whereas the epidermal and dermal layers of skin were not well-healed.

Example 13: Preparation of *Spiranthes sinensis* Extract

Air-dried *Spiranthes sinensis* was obtained from a local market, Hualien, Taiwan. The dried *Spiranthes sinensis* was ground into powder and extracted with 100% ethyl acetate (preferably, 10 fold dry weight volumes) for one week at room temperature (RT). The liquid extract was in vacuo evaporated to produce its dried powder with a yield of about 20.9% on a dry weight basis. For the following experiments, a stock composition was made by dissolving said extract in DMSO at a concentration of 1 mg/mL based on the total volume of said DMSO. A stock composition was made by dissolving the extract in DMSO at a concentration of 1 mg/mL based on the total volume of DMSO.

Example 14: Effects of *Spiranthes sinensis* Extract on Cell Viability

The RAW264.7 murine macrophage cell line was purchased from the Bioresource Collection and Research Center (BCRC, Taiwan). The cells were incubated at 37° C. in 5% $CO_2$ in Dulbecco's modified Eagle's medium (DMEM; Gibco Inc., NY, USA) supplemented with 100 U/mL penicillin, 100 µg/mL sodium pyruvate and 10% fetal bovine serum (FBS; Gibco Inc.). The cells were also treated with 0.01% DMSO as a vehicle control. The cells were seeded into 12-well plates at a density of $6 \times 10^5$ cells/well in 24 h, then incubated with 0.1% BSA with serum-free medium 3 h, treated with various concentrations (5, 10, 20, 50, and 100 µg/mL) of the *Spiranthes sinensis* extract as prepared in Example 13, and then incubated in the presence of LPS (0.4 or 1 µg/mL) for additional 4 h.

Figure 24:
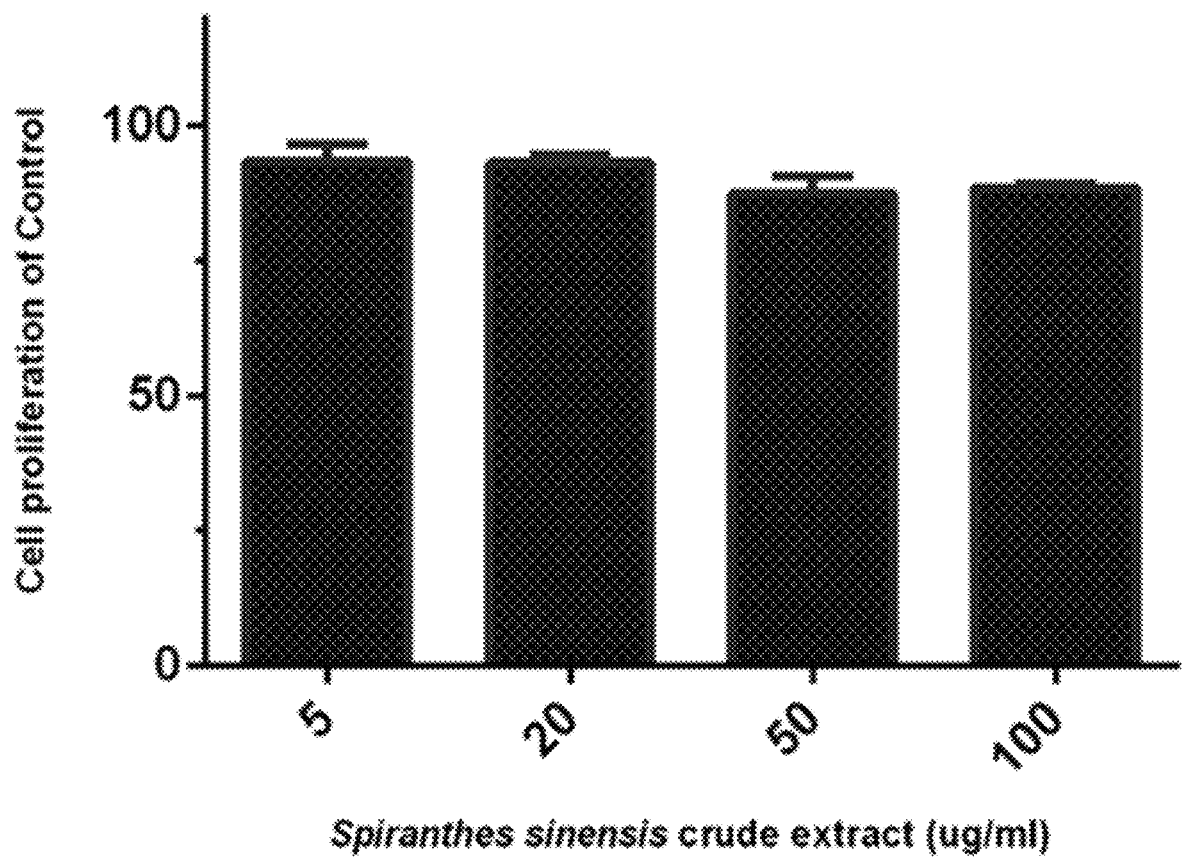
FIG. 24 illustrates the results of cell viability experiments.

In order to examine the bio-compatibility of the *Spiranthes sinensis* extract, an MTT assay (3-(4,5-dimethylthiazol-2-yl)-2,5-diphenyltetrazolium bromide (MTT, Invitrogen), a colorimetric based assay) was performed in this example. Briefly, $8 \times 10^3$ of cells per well were seeded in 96-well plates and were incubated in 5% $CO_2$ at 37° C. overnight. Cells were treated with different concentrations (5, 20, 50, and 100 µg/mL) of *Spiranthes sinensis* extract for 24 h, after incubation 20 µL (5 mg/mL) of MTT solution was added per well and further incubated for 4 h. The media was removed, and formazan was solubilized by adding 100 µL/well of DMSO (Sigma-Aldrich) and OD was measured at 570 nm using a microplate reader (ELISA reader, Thermo Labsystems). Percentage of viable cells was estimated by comparing with untreated control cells. The average absorbance value of the control cells was taken as 100% viability. The results indicate that the *Spiranthes sinensis* extract caused no harm to the cells at the doses given (see FIG. 24).

Example 15: Effects of *Spiranthes sinensis* Extract on MMP2 in Cell Culture In this example, the activity of MMP 2 was determined by gelatin zymography. $2 \times 10^5$ HSCs were seeded into 6-well plates. After 70 to 80% confluence; cells were starved in DMEM containing 0.1% BSA for 6 h, and then treated with different concentrations (5, 20, 50, and 100 µg/mL) of *Spiranthes sinensis* extract for 24 h, respectively. The conditioned medium was collected, centrifuged at 12,000×g at 4° C. for 30 min to remove the cell debris. The supernatant was collected and quantified using Bradford dye (Bio-Rad). 8% SDS-PAGE gels were prepared containing 10% gelatin. Proteins were pre-heated at 55° C. with 2× loaded dye (0.125 M Tris-HCl, pH 6.8, 4% SDS, 0.04% Bromophenol blue, 20% Glycerol). 7.5 µg of protein sample was loaded into the gel and electrophoresis separation was performed at 80V for 2-3 h. After electrophoresis, gel was washed 2 times in 50 mL of 2.5% Triton X-100 per gel, and then incubated in developing buffer (0.05 M Tris-HCl, pH 8.8, 5 mM $CaCl_2$), 0.02% $NaN_3$) at 37° C. for 16 h. Finally, gel was stained in 0.1% Coomassie blue R-250 (Bio-Rad) for 4 h and then destained by fixing buffer (45% methanol, 10% acetic acid). Gels were scanned using Epson scanner and quantified using multi-gauge software (Fujifilm).

Figure 27A:
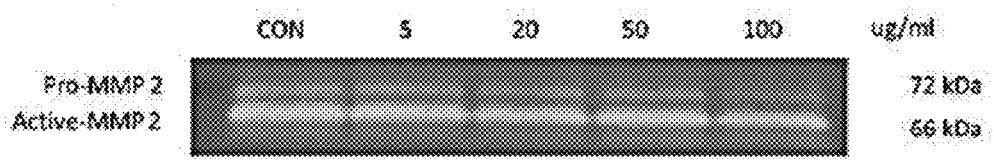
Figure 27B:
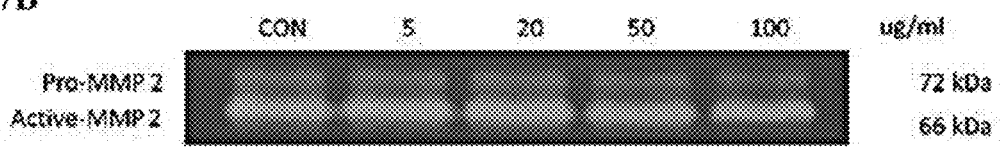
Figure 21C:
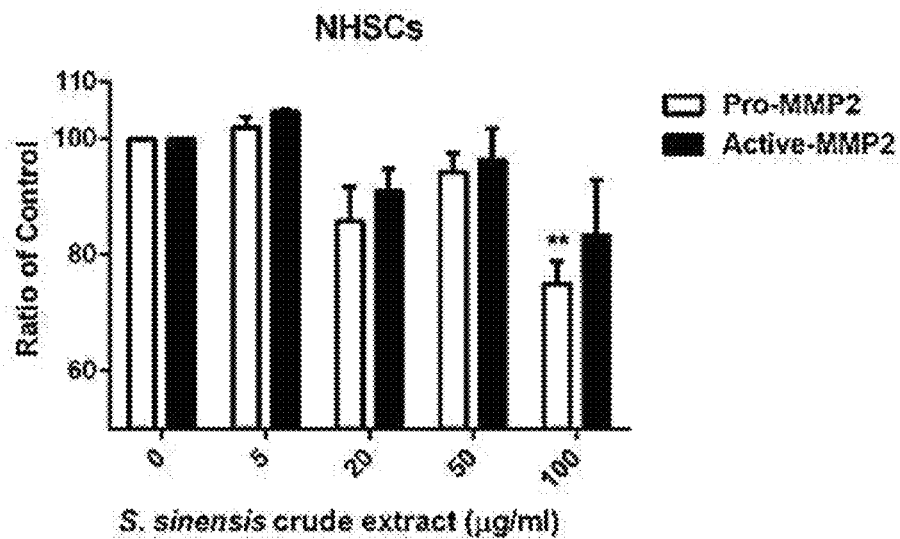
Figure 27D:
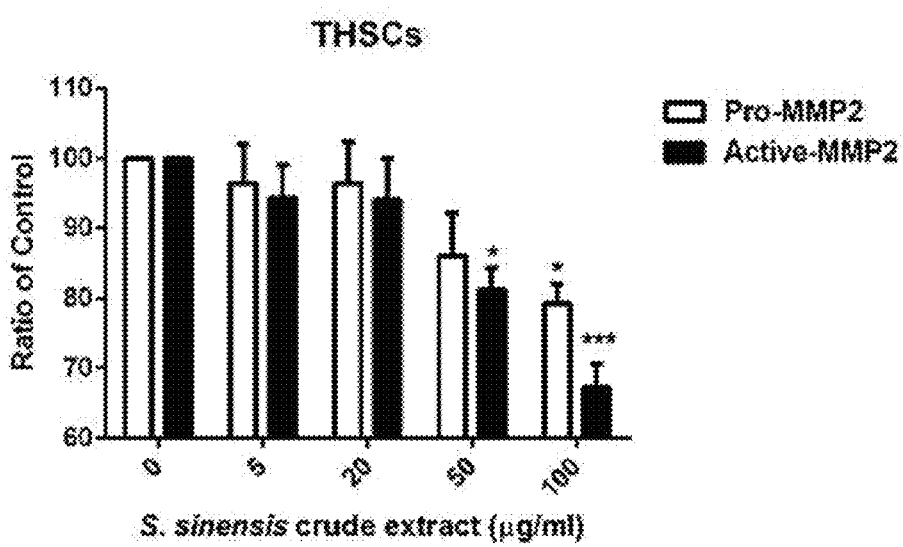

Activity of MMP2 was quantified by densitometer. Results are illustrated in FIG. 27, and show that MMP2 activity was reduced in both NHSCs and THSCs treated with 5, 20, 50, and 100 µg/mL of *Spiranthes sinensis* extract.

What is claimed is:

1. A method of promoting wound healing, the method comprising administering to a subject in need thereof an effective amount of a composition, wherein the composition consists of sinetirucallol and a pharmaceutically acceptable carrier, and wherein the composition is formulated for administration to a subject.

2. The method of claim 1, wherein the composition comprises at least 4.4 µg of sinetirucallol.

3. The method of claim 1, wherein the composition comprises sinetirucallol in an amount between 4.4 µg and 44 µg.

4. The method of claim 1, wherein the composition is administered via intravenous, intraarterial, oral, parenteral, buccal, topical, transdermal, rectal, intramuscular, subcutaneous, intraosseous, transmucosal or intraperitoneal administration.

5. The method of claim 2, wherein the composition is administered via intravenous, intraarterial, oral, parenteral, buccal, topical, transdermal, rectal, intramuscular, subcutaneous, intraosseous, transmucosal or intraperitoneal administration.

6. The method of claim 1, wherein the said carrier is at least one of an insert solid diluent, an insert solid filler, a sterile aqueous solution, an organic solvent, a permeation enhancer, a solubilizer, and an adjuvant.

* * * * *